US011945815B2

(12) United States Patent
Jones et al.

(10) Patent No.: US 11,945,815 B2
(45) Date of Patent: *Apr. 2, 2024

(54) PTPN11 INHIBITORS

(71) Applicant: NAVIRE PHARMA, INC., Palo Alto, CA (US)

(72) Inventors: Philip Jones, Houston, TX (US); Barbara Czako, Bellaire, TX (US); Christopher L Carroll, Houston, TX (US); Pijus Mandal, Sugarland, TX (US); Jason Cross, Pearland, TX (US)

(*) Notice: Subject to any disclaimer, the term of this patent is extended or adjusted under 35 U.S.C. 154(b) by 205 days.

This patent is subject to a terminal disclaimer.

(21) Appl. No.: 17/380,943

(22) Filed: Jul. 20, 2021

(65) Prior Publication Data
US 2022/0041594 A1 Feb. 10, 2022

Related U.S. Application Data

(63) Continuation of application No. 16/536,923, filed on Aug. 9, 2019, now Pat. No. 11,104,675.

(60) Provisional application No. 62/773,921, filed on Nov. 30, 2018, provisional application No. 62/717,588, filed on Aug. 10, 2018.

(51) Int. Cl.
C07D 471/04 (2006.01)
A61P 35/00 (2006.01)
C07D 491/107 (2006.01)

(52) U.S. Cl.
CPC ............ C07D 471/04 (2013.01); A61P 35/00 (2018.01); C07D 491/107 (2013.01)

(58) Field of Classification Search
CPC .................................................. C07D 471/04
See application file for complete search history.

(56) References Cited

U.S. PATENT DOCUMENTS

| 7,897,607 B2 | 3/2011 | Gyorkos |
| 9,522,881 B2 | 12/2016 | Zhang et al. |
| 10,280,171 B2 | 5/2019 | Jones et al. |
| 10,851,110 B2 | 12/2020 | Jones et al. |
| 10,954,243 B2 | 3/2021 | Jones et al. |
| 11,104,675 B2 * | 8/2021 | Jones ................... C07D 491/10 |
| 2005/0203091 A1 | 9/2005 | Arora |
| 2011/0152242 A1 | 6/2011 | Bayliss et al. |
| 2017/0015680 A1 | 1/2017 | Chen et al. |
| 2017/0342078 A1 | 11/2017 | Jones et al. |
| 2019/0270746 A1 | 9/2019 | Jones et al. |
| 2019/0389867 A1 | 12/2019 | Jones et al. |
| 2020/0048249 A1 | 2/2020 | Jones et al. |
| 2021/0317122 A1 | 10/2021 | Jones et al. |

FOREIGN PATENT DOCUMENTS

| CN | 107286150 A | 10/2017 |
| CN | 110143949 A | 8/2019 |
| JP | 2010111624 A | 5/2010 |
| JP | 2011246389 A | 12/2011 |
| WO | WO-2005028480 A2 | 3/2005 |
| WO | WO-2005085248 A1 | 9/2005 |
| WO | WO-2006058074 A1 | 6/2006 |
| WO | WO-2006063820 A1 | 6/2006 |
| WO | WO-2008061109 A2 | 5/2008 |
| WO | WO-2008100985 A2 | 8/2008 |
| WO | WO-2010039789 A1 | 4/2010 |
| WO | WO-2011055911 A1 | 5/2011 |
| WO | WO-2012106343 A2 | 8/2012 |
| WO | WO-2013040527 A1 | 3/2013 |
| WO | WO-2013052263 A1 | 4/2013 |
| WO | WO-2014047662 A2 | 3/2014 |
| WO | WO-2014200682 A1 | 12/2014 |
| WO | WO-2015099481 A1 | 7/2015 |
| WO | WO-2015107493 A1 | 7/2015 |
| WO | WO-2015107494 A1 | 7/2015 |
| WO | WO-2015107495 A1 | 7/2015 |
| WO | WO-2015190718 A1 | 12/2015 |
| WO | WO-2016064102 A1 | 4/2016 |
| WO | WO-2016151501 A1 | 9/2016 |
| WO | WO-2016203404 A1 | 12/2016 |
| WO | WO-2016203405 A1 | 12/2016 |
| WO | WO-2016203406 A1 | 12/2016 |
| WO | WO-2017156397 A1 | 9/2017 |
| WO | WO-2017210134 A1 | 12/2017 |
| WO | WO-2017211303 A1 | 12/2017 |
| WO | WO-2017216706 A1 | 12/2017 |
| WO | WO-2018013597 A1 | 1/2018 |
| WO | WO-2018057884 A1 | 3/2018 |
| WO | WO-2018081091 A1 | 5/2018 |
| WO | WO-2018130928 A1 | 7/2018 |
| WO | WO-2018136264 A1 | 7/2018 |
| WO | WO-2018136265 A1 | 7/2018 |
| WO | WO-2018172984 A1 | 9/2018 |

(Continued)

OTHER PUBLICATIONS

U.S. Appl. No. 62/307,103, Czako et al.
Amarnath et al., The PDL1-PD1 axis converts human TH1 cells into regulatory T cells, Sci Transl Med, Nov. 30, 2011, 3(111):111ra120.
Anderson et al., Structural and evolutionary relationships among protein tyrosine phosphatase domains, Mol Cell Biol, Nov. 2001, 21(21):7117-7136.
Banker et al., Prodrugs, Modern Pharmaceuticals, 1997, 3rd Edition, p. 596, 451.
Barr et al., Large-scale structural analysis of the classical human protein tyrosine phosphatome, Cell, Jan. 23, 2009, 136(2):352-363.

(Continued)

*Primary Examiner* — Paul V Ward
(74) *Attorney, Agent, or Firm* — Mintz, Levin, Cohn, Ferris Glovsky & Popeo, P.C.

(57) ABSTRACT

The present invention relates to compounds which are useful as inhibitors of PTPN11 for the treatment or prevention of cancer and other PTP-mediated diseases. Disclosed herein are new compounds and compounds based on pyrazolopyrazines and their application as pharmaceuticals for the treatment of disease.

16 Claims, 2 Drawing Sheets

(56) References Cited

FOREIGN PATENT DOCUMENTS

| WO | WO-2018218133 A1 | 11/2018 |
|---|---|---|
| WO | WO-2019051084 A1 | 3/2019 |
| WO | WO-2019051469 A1 | 3/2019 |
| WO | WO-2019067843 A1 | 4/2019 |
| WO | WO-2019075265 A1 | 4/2019 |
| WO | WO-2019118909 A1 | 6/2019 |
| WO | WO-2019152454 A1 | 8/2019 |
| WO | WO-2019158019 A1 | 8/2019 |
| WO | WO-2019165073 A1 | 8/2019 |
| WO | WO-2019167000 A1 | 9/2019 |
| WO | WO-2019182960 A1 | 9/2019 |
| WO | WO-2019183364 A1 | 9/2019 |
| WO | WO-2019183367 A1 | 9/2019 |
| WO | WO-2019199792 A1 | 10/2019 |
| WO | WO-2019213318 A1 | 11/2019 |
| WO | WO-2019233810 A1 | 12/2019 |
| WO | WO-2020022323 A1 | 1/2020 |
| WO | WO-2020033784 A1 | 2/2020 |
| WO | WO-2020033828 A1 | 2/2020 |
| WO | WO-2020109509 A1 | 6/2020 |
| WO | WO-2020109511 A1 | 6/2020 |
| WO | WO-2020110056 A1 | 6/2020 |
| WO | WO-2020112700 A1 | 6/2020 |
| WO | WO-2020113209 A1 | 6/2020 |
| WO | WO-2020113213 A2 | 6/2020 |

OTHER PUBLICATIONS

Chan et al., The tyrosine phosphatase Shp2 (PTPN11) in cancer, Cancer Metastasis Rev, Jun. 2008, 27(2):179-192.
Chen et al., Allosteric inhibition of SHP2 phosphatase inhibits cancers driven by receptor tyrosine kinases, Nature, Jul. 7, 2016, Vo. 535, pp. 148-152.
Darian et al., Structural mechanism associated with domain opening in gain-of-function mutations in SHP2 phosphatase, Proteins, May 2011, e-published Mar. 1, 2011, 79(5):1573-1588.
Grossmann et al., The tyrosine phosphatase Shp2 in development and cancer, Adv Cancer Res, 2010, 106:53-89.
Huang et al., Structure, function, and pathogenesis of SHP2 in developmental disorders and tumorigenesis, Curr Cancer Drug Targets, 2014, 14(6):567-588.
International Search Report for International Application No. PCT/US2017/021784, dated Jul. 7, 2017, 4 pages.
International Search Report for International Application No. PCT/US2017/034806, dated Sep. 6, 2017, 2 pages.
International Search Report for International Application No. PCT/US2017/030277, dated Jul. 26, 2019, 3 pages.
International Search Report for International Application No. PCT/US2019/045903 dated Oct. 28, 2019, 5 pages.
Li et al., PD-1/SHP-2 inhibits Tc1/Th1 phenotypic responses and the activation of T cells in the tumor microenvironment, Cancer Res, Feb. 1, 2015, e-published Dec. 5, 2014, 75(3):508-518.
McMahon et al., VEGF Receptor Signaling in Tumor Angiogenesis, The Oncologist, 2000, 5(suppl 1):3-10.
Mohi et al., The role of Shp2 (PTPN11) in cancer, Curr Opin Genet Dev, Feb. 2007, e-published Jan. 16, 2007, 17(1):23-30.
Okazaki et al., PD-1 immunoreceptor inhibits B cell receptor-mediated signaling by recruiting src homology 2-domain-containing tyrosine phosphatase 2 to phosphotyrosine, PNAS USA, Nov. 20, 2001, e-published Nov. 6, 2001, 98(24):13866-13871.
Pinedo et al., Translational Research: The Role of VEGF in Tumor Angiogenesis, the Oncologist, 2000, 5(suppl 1):1-2.
Prahallad et al., PTPN11 Is a Central Node in Intrinsic and Acquired Resistance to Targeted Cancer Drugs, Cell Rep, Sep. 29, 2015, e-published Sep. 10, 2015, 12(12):1978-1985.
Pubchem CID 57384833: Create Date: Jul. 23, 2012; Date accessed: Jun. 19, 2017; p. 3.
Qiu et al., Structural insights into Noonan/LEOPARD syndrome-related mutants of protein-tyrosine phosphatase SHP2 (PTPN11), BMC Struct Biol, Mar. 14, 2014, 14:10.
Revesz et al., Novel p38a MAP kinase inhibiting scaffolds with oral activity Bioorganic & Medicinal Chemistry Letters, 2006, 16(2), 262-266.
Tajan et al., SHP2 sails from physiology to pathology, Eur J Med Genet, Oct. 2015, e-published May 28, 2012, 58(10):509-525.
Vippagunta et al., Crystalline solids, Advance Drug Delivery Reviews, 2001, vol. 49, pp. 3-26.
Wolff, Some Considerations for Prodrug Design, Burger's Medicinal Chemistry And Drug Discovery, 1997, pp. 975-977.
Yokosuka et al., Programmed cell death 1 forms negative costimulatory microclusters that directly inhibit T cell receptor signaling by recruiting phosphatase SHP2, J Exp Med, Jun. 4, 2012, e-published May 28, 2012, 209(6):1201-1217.
Yu et al., Structural and mechanistic insights into LEOPARD syndrome-associated SHP2 mutations, J Biol Chem, Apr. 12, 2013, e-published Mar. 1, 2013, 288(15):10472-10482.
Wong et al., Targeting wild-type KRAS-amplified gastroesophageal cancer through combined MEK and SHP2 inhibition, Nature Medicine, 2018, vol. vol. 24, pp. 968-977.
Written Opinion for International Application No. PCT/US2017/021784, dated Jul. 7, 2017, 6 pages.
Written Opinion for International Application No. PCT/US2017/034806, dated Sep. 6, 2017, 5 pages.
Written Opinion for International Application No. PCT/US2019/030277, dated Jul. 26, 2019, 5 pages.
Written Opinion for International Application No. PCT/US2019/045903, dated Oct. 28, 2019, 6 pages.
Ciapetti et al., Chapter 15—Molecular Variations Based on Isosteric Replacements, The Practice of Medicinal Chemistry, Jan. 1, 2008, 3rd Edition, pp. 290-342.
European Patent Office, Extended European Search Report for European Application No. 19796849.8, dated Nov. 2, 2021, 9 pages.

\* cited by examiner

PTPN11 INHIBITORS

CROSS-REFERENCES TO RELATED APPLICATIONS

This application is a continuation of U.S. patent application Ser. No. 16/536,923, filed Aug. 9, 2019, which claims benefit of priority to U.S. Provisional Application No. 62/717,588, filed Aug. 10, 2018 and U.S. Provisional Application No. 62/773,921, filed Nov. 30, 2018, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Disclosed herein are new compounds and compounds based on pyrimidinones and their application as pharmaceuticals for the treatment of disease. Methods of inhibition of PTPN11 (SHP2) activity in a human or animal subject are also provided for the treatment diseases such as cancer, including leukemia and melanoma, and cancers of the breast, lung, and colon.

Tyrosyl phosphorylation regulates human cellular processes from cell differentiation to growth and apoptosis, and others. Tyrosyl phosphorylation is regulated by protein-tyrosine kinases (PTK) and protein-tyrosine phosphatases (PTP). The breakdown of regulation governed by PTK and PTP activity is thought to lead to cancer. PTK inhibitors have been developed as potential cancer therapeutic agents. Recent studies disclose a role for PTPs in cellular regulation as well. (A J Barr et al. *Cell* 2009, 136, 352-363. J N Andersen et al *Mol. Cell. Biol.* 2001, 21, 7117-7136).

Protein-tyrosine phosphatase non-receptor type 11 (PTPN11, also known as Src Homology-2 phosphatase (SHP2)) is a non-receptor protein tyrosine phosphatase encoded by the PTPN11 gene. This PTP contains two tandem Src homology-2 (SH2) domains, which function as phospho-tyrosine binding domains, a catalytic domain, and a C-terminal tail. In the basal state the protein typically exists in an inactive, self-inhibited conformation with the N-terminal SH2 domain blocking the active site. When stimulated by signal transduction mediated by cytokines and growth factor binding of phosphorylated proteins to the SH2 domains the auto-inhibition is relieved, this makes the active site available for dephosphorylation of PTPN11 substrates (MG Mohl, BG Neel, *Curr. Opin. Genetics Dev.* 2007, 17, 23-30. KS Grossmann, *Adv. Cancer Res.* 2010, 106, 53-89. W. Q. Huang et. al. *Curr. Cancer Drug Targets* 2014, 14, 567-588. C. Gordon et. al. *Cancer Metastasis Rev.* 2008, 27, 179-192).

Germ-line and somatic mutations in PTPN11 have been reported in several human diseases resulting in gain-of-function in the catalytic activity, including Noonan Syndrome and Leopard Syndrome; as well as multiple cancers such as juvenile myelomonocytic leukemia, neuroblastoma, myelodysplastic syndrome, B cell acute lymphoblastic leukemia/lymphoma, melanoma, acute myeloid leukemia and cancers of the breast, lung and colon (MG Mohl, BG Neel, *Curr. Opin. Genetics Dev.* 2007, 17, 23-30). Recent studies have demonstrated that single PTPN11 mutations are able to induce Noonan syndrome, JMML-like myeloproliferative disease and acute leukemia in mice. These mutations disrupt the auto-inhibition between the N—SH2 domains and the catalytic site allowing constitutive access of substrates to the catalytic site of the enzyme (E. Darian et al, *Proteins,* 2011, 79, 1573-1588. Z—H Yu et al, *JBC,* 2013, 288, 10472, W Qiu et al *BMC Struct. Biol.* 2014, 14, 10).

PTPN11 is widely expressed in most tissues and plays a regulatory role in various cell signaling events that are important for a diversity of cell functions that includes proliferation, differentiation, cell cycle maintenance, EMT transition, mitogenic activation, metabolic control, transcription regulation, and cell migration, through multiple signaling pathways including the Ras-MAPK, the JAK-STAT or the PI3K-AKT pathways (Tajan, M. et. al. *Eur. J. Medical Genetics,* 2015, 58, 509-525. Prahallad, A. et. al. *Cell Reports,* 2015, 12, 1978-1985).

Additionally there is growing evidence that PTPN11/SHP2 is implicated in immune evasion during tumorigenesis, and hence a SHP2 inhibitor could stimulate the immune response in cancer patients (*Cancer Res.* 2015 Feb. 1; 75(3):508-18. T Yokosuka T, *J Exp Med.* 2012, 209(6), 1201. S Amarnath *Sci Transl Med.* 2011, 3, 111ra120. T Okazaki, *PNAS* 2001, 98:24, 13866-71).

Novel compounds and pharmaceutical compositions, certain of which have been found to inhibit PTPN11 (SHP2) have been discovered, together with methods of synthesizing and using the compounds including methods for the treatment of PTP-mediated diseases in a patient by administering the compounds.

BRIEF SUMMARY OF THE INVENTION

In certain embodiments of the present invention, compounds are represented by Formula I:

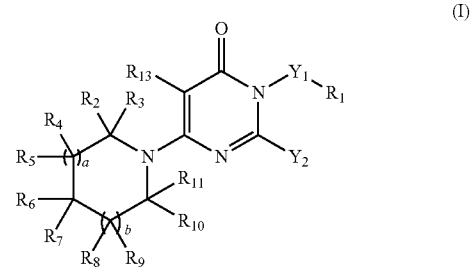

(I)

or a salt or tautomer thereof, wherein the subscripts a and b, $Y_1$, $Y_2$, and $R_1$, $R_2$, $R_3$, $R_4$, $R_5$, $R_6$, $R_7$, $R_8$, $R_9$, $R_{10}$, $R_{11}$, and $R_{13}$ are as provided herein.

In certain embodiments, the present invention provides a pharmaceutical composition including a compound having Formula I, together with a pharmaceutically acceptable carrier.

In certain embodiments, the present invention provides methods of inhibition of PTPN11 (SHP2) activity in a human or animal subject for the treatment diseases such as cancer, including leukemia and melanoma, and cancers of the breast, lung, and colon.

DETAILED DESCRIPTION OF THE INVENTION

I. General

Figure 1:
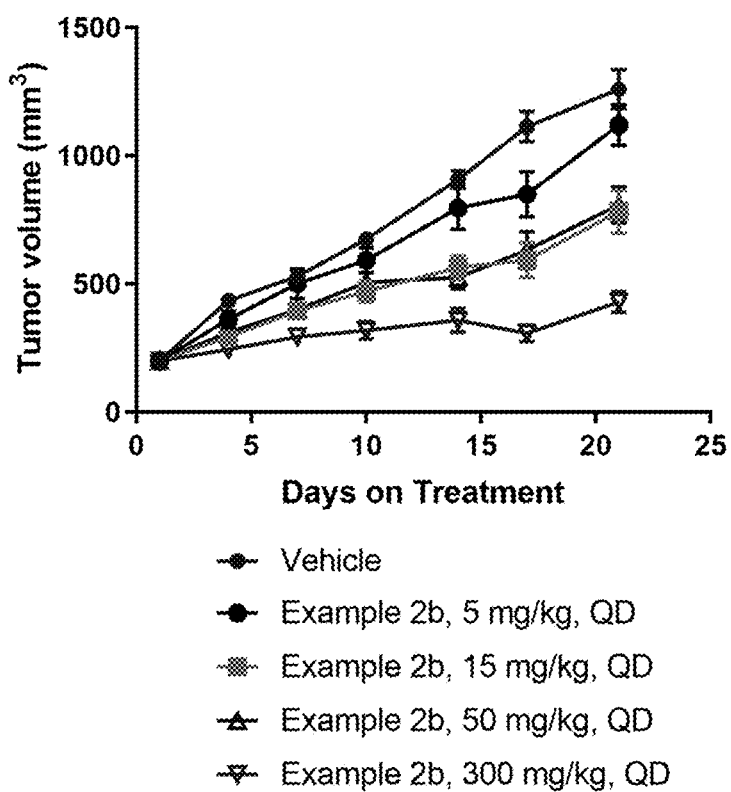
FIG. 1 shows a dose-dependent tumor growth inhibition by 6-((3S,4S)-4-amino-3-methyl-2-oxa-8-azaspiro[4.5]decan-8-yl)-3-($R_a$)-(2,3-dichlorophenyl)-2-methylpyrimidin-4(3H)-one (Example 2b) in the KYSE520 xenograft model.

Certain compounds of Formula I disclosed herein may possess useful PTPN11 inhibiting activity, and may be used in the treatment or prophylaxis of a disease or condition in which PTPN11 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting PTPN11. Other embodiments provide methods for treating a PTPN11-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PTPN11. In particular, the PTPN11-mediated disease is cancer.

II. Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkynyl" refers to either a straight chain or branched hydrocarbon having at least 2 carbon atoms and at least one triple bond and having the number of carbon atom indicated (i.e., $C_{2-6}$ means to two to six carbons). Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The terms "amido" and "carbamoyl," as used herein, alone or in combination, refer to an amino group as described below attached to the parent molecular moiety through a carbonyl group, or vice versa. The "amido" group as used herein incudes a "C-amido" and "N-amido" groups.

The term "C-amido" as used herein, alone or in combination, refers to a —C(O)N(RR') group with R and R' as defined herein or as defined by the specifically enumerated "R" groups designated. In some embodiments, the "amido" group includes —C(O)NH$_2$, C$_{1-4}$alkylamido, and di(C$_{1-4}$alkyl)amido. The term "C$_{1-4}$alkylamido", as used herein, refers to —C(O)NH(C$_{1-4}$alkyl), wherein C$_{1-4}$alkyl is as defined herein. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which is optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term aryloxy as used herein, alone or in combination, refers to an aryl group attached to the parent molecular moiety through an oxy.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. The term "cycloalkenyl" refers to a cycloalkyl group having one or two double bonds. In certain embodiments, said cycloalkyl (or cycloalkenyl) will comprise from 5 to 7 carbon atoms. Examples of such groups include cyclopropyl, cyclobutyl, cyclopentyl, cyclohexyl, cycloheptyl, cyclobutenyl, cyclopentenyl, cyclohexenyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro, or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms selected from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently selected from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups are optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "iminohydroxy," as used herein, alone or in combination, refers to —N(OH) and =N—O—.

The term "lower amino," as used herein, alone or in combination, refers to —NRR', wherein R and R' are independently selected from hydrogen and lower alkyl, either of which is optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "ring," or equivalently, "cycle," as used herein, in reference to a chemical structure or portion thereof, means a group in which every atom is a member of a common cyclic structure. A ring can be saturated or unsaturated, including aromatic, unless otherwise provided, and may have between 3 and 9 members. If the ring is a heterocycle, it may contain between 1 and 4 heteroatoms or heteroatom-comprising groups selected from B, N, O, S, C(O), S(O)$_m$. Unless specifically prohibited, a ring is optionally substituted.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The term "tautomer", as use herein, alone or in combination, refers to one of two or more isomers that rapidly interconvert. Generally, this interconversion is sufficiently fast so that an individual tautomer is not isolated in the absence of another tautomer. The ratio of the amount of tautomers can be dependent on solvent composition, ionic strength, and pH, as well as other solution parameters. The ratio of the amount of tautomers can be different in a particular solution and in the microenvironment of a biomolecular binding site in said solution. Examples of tautomers that are well known in the art include keto/enol, enamine/imine, and lactam/lactim tautomers. Examples of tautomers that are well known in the art also include 2-hydroxypyridine/2(1H)-pyridone and 2-aminopyridine/2(1H)-iminopyridone tautomers.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower haloalkyl, lower haloalkenyl, lower haloalkynyl, lower perhaloalkyl, lower perhaloalkoxy, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

Conformational isomers exist in the compounds disclosed herein. When $R_1$ is aryl or heteroaryl in the formula:

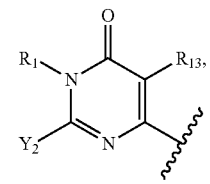

the aryl or heteroaryl group can orient in different conformations in relation to the pyrimidinone moiety, as represented by:

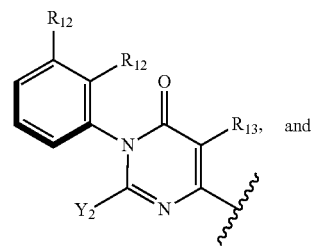

($S_a$ form)

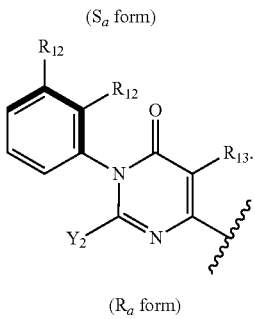

($R_a$ form)

These forms are designated by the symbols "$S_a$" or "$R_a$", depending on the conformation of the aryl or heteroaryl group in relation to the pyrimidinone moeity. Examples of "$S_a$" and "$R_a$" forms can be found in Examples 1-20.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PTPN11 inhibitor" is used herein to refer to a compound that exhibits an $IC_{50}$ with respect to PTPN11 activity of no more than about 100 µM and more typically not more than about 50 µM, as measured in the PTPN11 assay described generally herein. "$IC_{50}$" is that concentration of inhibitor which reduces the activity of an enzyme (e.g., PTPN11) to half-maximal level. Certain compounds disclosed herein have been discovered to exhibit inhibition against PTPN11. In certain embodiments, compounds will exhibit an $IC_{50}$ with respect to PTPN11 of no more than about 50 µM; in further embodiments, compounds will exhibit an $IC_{50}$ with respect to PTPN11 of no more than about 10 µM; in yet further embodiments, compounds will exhibit an $IC_{50}$ with respect to PTPN11 of not more than about 1 µM; in yet further embodiments, compounds will exhibit an $IC_{50}$ with respect to PTPN11 of not more than about 200 nM, as measured in the PTPN11 assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

III. Compounds

In one aspect, the present invention provides a compound represented by Formula I:

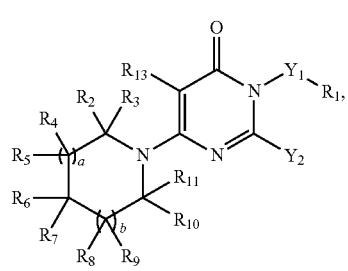

(I)

or a salt, ester, or prodrug thereof, wherein:

subscript a is 0 or 1;
subscript b is 0 or 1;
$Y_1$ is a direct bond or $CR_{17}R_{18}$;
$Y_2$ is selected from the group consisting of $C_{1-4}$alkyl, amino, $C_{1-4}$alkylC(O)O—, $C_{1-4}$alkylamino and $C_{1-4}$aminoalkyl;
$R_1$ is selected from the group consisting of $C_{6-10}$aryl, $C_{3-8}$cycloalkyl, $C_{3-8}$cycloalkenyl, and a 5-10 membered heteroaryl group having 1 to 4 heteroatoms or groups as ring vertices independently selected from N, C(O), O, and S; said aryl or heteroaryl of $R_1$ is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{14}$, $NR_{15}C(O)OR_{14}$, $NR_{14}C(O)NR_{15}R_{16}$, $NR_{15}S(O)R_{14}$, $NR_{15}S(O)_2R_{14}$, $C(O)NR_{15}R_{16}$, $S(O)NR_{15}R_{16}$, $S(O)_2NR_{15}R_{16}$, $C(O)R_4$, $C(O)OR_{14}$, $OR_{14}$, $SR_{14}$, $S(O)R_{14}$, and $S(O)_2R_{14}$;

$R_2$, $R_3$, $R_{10}$, and $R_{11}$ are each independently selected from the group consisting of hydrogen, $C_{1-4}$alkyl, and $C_{3-8}$cycloalkyl;

$R_4$, $R_5$, $R_8$, and $R_9$ are each independently selected from the group consisting of hydrogen, cyano, $C_{1-4}$alkyl, $C_{1-4}$alkoxy, amino, hydroxy, $C_{3-8}$cycloalkyl, halo, and $C_{1-4}$alkylamino;

$R_6$ is selected from the group consisting of amino, $C_{1-4}$aminoalkyl, and $C_{1-4}$alkylamino;

$R_7$ is selected from the group consisting of hydrogen, amido, cyano, halo, and hydroxy, or is selected from the group consisting of $C_{1-4}$alkyl, $C_{1-4}$hydroxyalkyl, $C_{3-6}$cycloalkyl, phenyl, and 5- or 6-membered heteroaryl, any of which is optionally substituted with one to five groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino, and $C_{1-4}$aminoalkyl;

or $R_6$ and $R_7$ together with the carbon atom to which they are both attached form a 3- to 7-membered saturated or unsaturated ring, having 0 to 3 heteroatoms or groups as ring vertices independently selected from N, C(O), O, and $S(O)_m$;

subscript m is 0, 1, or 2;

said saturated or unsaturated ring formed by $R_6$ and $R_7$ is unsubstituted or substituted with 1 to 3 groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl;

any two groups of $R_2$, $R_3$, $R_4$, $R_5$, $R_7$, $R_8$, $R_9$, $R_{10}$ and $R_{11}$ can form a 5 to 6 membered ring, having 0 to 2 heteroatoms as ring vertices selected from N, O and S;

any two groups of $R_2$, $R_4$, $R_6$, $R_8$ and $R_{10}$ can form a direct bond, or a 1 or 2 atom carbon bridge;

$R_{13}$ is selected from the group consisting of hydrogen, halo, cyano, $C_{1-6}$alkyl, $C_{1-6}$haloalkyl, $C_{1-6}$hydroxyalkyl, $C_{1-6}$dihydroxyalkyl, —NH—NHR$_{19}$, —NHR$_{19}$, —OR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}$R$_{20}$, —C(O)NH(CH$_2$)$_q$OH, —C(O)NH(CH$_2$)$_q$R$_{21}$, —C(O)R$_{21}$, —NH$_2$, —OH, —S(O)$_2$NR$_{19}$R$_{20}$, $C_{3-8}$cycloalkyl, aryl, heterocyclyl having 1-5 heteroatoms as ring vertices selected from N, O, S and P, heteroaryl having 1-5 heteroatoms as ring vertices selected from N, O, S and P; wherein the subscript q is an integer of from 0 to 6; and wherein aryl, heteroaryl, heterocyclyl and cycloalkyl are substituted with 0 to 3 groups independently selected from the group consisting of $C_{1-4}$alkyl, —OH, —NH$_2$, —OR$_{21}$, halo, cyano, and oxo;

$R_{14}$, $R_{15}$ and $R_{16}$ are each independently selected from the group consisting of hydrogen, $C_{1-4}$alkyl, $C_{3-8}$cycloalkyl, $C_{6-10}$aryl and a 5-10 membered heteroaryl, each of which is optionally substituted by one or more groups independently selected from the group consisting of amido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl;

$R_{17}$ and $R_{18}$ are each independently selected from the group consisting of hydrogen, $C_{1-4}$alkyl, and $CF_3$;

$R_{19}$ and $R_{20}$ are each independently selected from the group consisting of hydrogen, $C_{1-6}$alkyl, $C_{1-6}$haloalkyl, $C_{1-6}$hydroxyalkyl, $C_{2-6}$alkenyl, $C_{2-4}$alkynyl and $C_{3-6}$cycloalkyl; and each $R_{21}$ is independently selected from the group consisting of hydrogen, —OH, $C_{1-6}$alkyl, $C_{1-6}$haloalkyl, $C_{1-6}$hydroxyalkyl, $C_{2-6}$alkenyl, $C_{2-6}$alkynyl and $C_{3-6}$cycloalkyl.

In some embodiments, the present invention provides a compound represented by Formula I:

$$\text{(I)}$$

or a salt, ester, or prodrug thereof, wherein:
subscript a is 0 or 1;
subscript b is 0 or 1;
$Y_1$ is a direct bond or $CR_{17}R_{18}$;
$Y_2$ is selected from the group consisting of $C_{1-4}$alkyl, amino, $C_{1-4}$alkylC(O)O—, $C_{1-4}$alkylamino and $C_{1-4}$aminoalkyl;
$R_1$ is selected from the group consisting of $C_{6-10}$aryl, $C_{3-8}$cycloalkyl, $C_{3-8}$cycloalkenyl, and a 5-10 membered heteroaryl group having 1 to 4 heteroatoms or groups as ring vertices independently selected from N, C(O), O, and S; said aryl or heteroaryl of $R_1$ is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{14}$, $NR_{15}C(O)OR_{14}$, $NR_{14}C(O)NR_{15}R_{16}$, $NR_{15}S(O)R_{14}$, $NR_{15}S(O)_2R_{14}$, $C(O)NR_{15}R_{16}$, $S(O)NR_{15}R_{16}$, $S(O)_2NR_{15}R_{16}$, $C(O)R_{14}$, $C(O)OR_{14}$, $OR_{14}$, $SR_{14}$, $S(O)R_{14}$, and $S(O)_2R_{14}$;
$R_2$, $R_3$, $R_{10}$, and $R_{11}$ are each independently selected from the group consisting of hydrogen, $C_{1-4}$alkyl, and $C_{3-8}$cycloalkyl;
$R_4$, $R_5$, $R_8$, and $R_9$ are each independently selected from the group consisting of hydrogen, cyano, $C_{1-4}$alkyl, $C_{1-4}$alkoxy, amino, hydroxy, $C_{3-8}$cycloalkyl, halo, and $C_{1-4}$alkylamino;
$R_6$ is selected from the group consisting of amino, $C_{1-4}$aminoalkyl, and $C_{1-4}$alkylamino;
$R_7$ is selected from the group consisting of hydrogen, halo, and hydroxy, or is selected from the group consisting of amido, $C_{1-4}$alkyl, $C_{1-4}$hydroxyalkyl, $C_{3-6}$cycloalkyl, phenyl, and 5- or 6-membered heteroaryl, any of which is optionally substituted with one to five groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino, and $C_{1-4}$aminoalkyl;
or $R_6$ and $R_7$ together with the carbon atom to which they are both attached form a 3- to 7-membered saturated or unsaturated ring, having 0 to 3 heteroatoms or groups as ring vertices independently selected from N, C(O), O, and $S(O)_m$;
subscript m is 0, 1, or 2;
said saturated ring formed by $R_6$ and $R_7$ is unsubstituted or substituted with 1 to 3 groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl;
any two groups of $R_2$, $R_3$, $R_4$, $R_5$, $R_7$, $R_8$, $R_9$, $R_{10}$ and $R_{11}$ can form a 5 to 6 membered ring, having 0 to 2 heteroatoms as ring vertices selected from N, O and S;
any two groups of $R_2$, $R_4$, $R_6$, $R_5$ and $R_{10}$ can form a direct bond, or a 1 or 2 atom carbon bridge;
$R_{13}$ is selected from the group consisting of hydrogen, halo, cyano, $C_{1-6}$alkyl, $C_{1-6}$haloalkyl, $C_{1-6}$hydroxyalkyl, $C_{1-6}$dihydroxyalkyl, —NH—$NHR_{19}$, —$NHR_{19}$, —$OR_{19}$, —$NHC(O)R_{19}$, —$NHC(O)NHR_{19}$, —$NHS(O)_2NHR_{19}$, —$NHS(O)_2R_{19}$, —$C(O)OR_{19}$, —$C(O)NR_{19}R_{20}$, —$C(O)NH(CH_2)_qOH$, —$C(O)NH(CH_2)_qR_{21}$, —$C(O)R_{21}$, —$NH_2$, —OH, —$S(O)_2NR_{19}R_{20}$, $C_{3-8}$cycloalkyl, aryl, heterocyclyl having 1-5 heteroatoms as ring vertices selected from N, O, S and P, heteroaryl having 1-5 heteroatoms as ring vertices selected from N, O, S and P; wherein the subscript q is an integer of from 0 to 6; and wherein aryl, heteroaryl, heterocyclyl and cycloalkyl are substituted with 0 to 3 groups independently selected from the group consisting of $C_{1-4}$alkyl, —OH, —$NH_2$, —$OR_{21}$, halo, cyano, and oxo;
$R_{14}$, $R_{15}$ and $R_{16}$ are each independently selected from the group consisting of hydrogen, $C_{1-4}$alkyl, $C_{3-8}$cycloalkyl, $C_{6-10}$aryl and 5-10 membered heteroaryl, each of which is optionally substituted by one or more groups independently selected from the group consisting of halo, hydroxy, cyano, and $C_{1-4}$alkyl;
$R_{17}$ and $R_{18}$ are each independently selected from the group consisting of hydrogen, $C_{1-4}$alkyl, and $CF_3$;
$R_{19}$ and $R_{20}$ are each independently selected from the group consisting of hydrogen, $C_{1-6}$alkyl, $C_{1-6}$haloalkyl, $C_{1-6}$hydroxyalkyl, $C_{2-6}$alkenyl, $C_{2-4}$alkynyl and $C_{3-6}$cycloalkyl; and
each $R_{21}$ is independently selected from the group consisting of hydrogen, —OH, $C_{1-6}$alkyl, $C_{1-6}$haloalkyl, $C_{1-6}$hydroxyalkyl, $C_{2-6}$alkenyl, $C_{2-6}$alkynyl and $C_{3-6}$cycloalkyl.

In some embodiments of Formula I, $Y_1$ is a direct bond. In some embodiments, $Y_1$ is $CR_{17}R_{18}$. In some embodiments, $R_{17}$ and $R_{18}$ are each independently selected from the group consisting of hydrogen, $C_{1-4}$alkyl, and $CF_3$. In some embodiments, $R_{17}$ and $R_{18}$ are each independently hydrogen or $C_{1-4}$alkyl. In some embodiments, $Y_1$ is —$CH_2$.

In some embodiments of Formula I, $Y_2$ is $C_{1-4}$alkyl. In some embodiments, $Y_2$ is methyl.

In some embodiments, the compound is represented by Formula Ia:

$$\text{(Ia)}$$

wherein the subscripts a and b, $Y_1$, $R_1$, $R_2$, $R_3$, $R_4$, $R_5$, $R_6$, $R_7$, $R_8$, $R_9$, $R_{10}$, $R_{11}$, and $R_{13}$ are as defined and described herein.

In some embodiments, the compound is represented by Formula Ib:

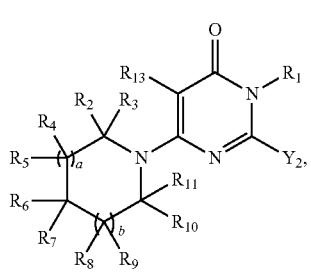

wherein the subscripts a and b, $Y_2$, $R_1$, $R_2$, $R_3$, $R_4$, $R_5$, $R_6$, $R_7$, $R_8$, $R_9$, $R_{10}$, $R_{11}$, and $R_{13}$ are as defined and described herein.

In some embodiments, the compound is represented by Formula Ic:

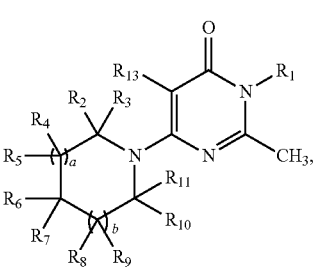

wherein the subscripts a and b, $R_1$, $R_2$, $R_3$, $R_4$, $R_5$, $R_6$, $R_7$, $R_8$, $R_9$, $R_{10}$, $R_{11}$, and $R_{13}$ are as defined and described herein.

In some embodiments of any one of Formulae I, Ia, Ib, and Ic, subscripts a and b are each 1.

In some embodiments of any one of Formulae I, Ia, Ib, and Ic, $R_{13}$ is selected from the group consisting of hydrogen, halo, $C_{1-4}$alkyl, $C_{1-6}$haloalkyl, $C_{1-6}$hydroxyalkyl, $C_{1-4}$dihydroxyalkyl, $C_{3-8}$cycloalkyl, 3- or 6-membered heterocyclyl having 1-3 heteroatoms as ring vertices selected from N, O and S; wherein heterocyclyl and cycloalkyl are substituted with 0 to 3 groups independently selected from the group consisting of $C_{1-4}$alkyl, —OH, —NH$_2$, —OR$_{21}$, halo, cyano and oxo. In some embodiments, $R_{13}$ is selected from the group consisting of hydrogen, halo, $C_{1-4}$alkyl, $C_{1-6}$haloalkyl, $C_{1-6}$hydroxyalkyl, $C_{1-6}$dihydroxyalkyl, and $C_{3-8}$cycloalkyl. In some embodiments, $R_{13}$ is selected from the group consisting of hydrogen, halo, $C_{1-6}$alkyl, and $C_{1-6}$haloalkyl. In some embodiments, $R_{13}$ is selected from the group consisting of hydrogen, halo, $C_{1-4}$alkyl, and $C_{1-4}$haloalkyl. In some embodiments, $R_{13}$ is selected from the group consisting of —CH$_2$OH, CF$_2$OH, and —CHFOH. In some embodiments, $R_{13}$ is selected from the group consisting of hydrogen, Cl, Br, methyl, and CF$_3$. In some embodiments, $R_{13}$ is hydrogen. In some embodiments, $R_{13}$ is Cl. In some embodiments, $R_{13}$ is Br. In some embodiments, $R_{13}$ is methyl. In some embodiments, $R_{13}$ is CF$_3$.

In some embodiments of any one of Formulae I, Ia, Ib, and Ic, $R_1$ is selected from the group consisting of $C_{6-10}$aryl and a 5- to 9-membered heteroaryl group having 1 to 4 heteroatoms groups as ring vertices independently selected from N, C(O), O, and S; and is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, NR$_{15}$C(O)R$_{14}$, NR$_{15}$C(O)OR$_{14}$, NR$_{14}$C(O)NR$_{15}$R$_{16}$, NR$_{15}$S(O)R$_{14}$, NR$_{15}$S(O)$_2$R$_{14}$, C(O)NR$_{15}$R$_{16}$, S(O)NR$_{15}$R$_{16}$, S(O)$_2$NR$_{15}$R$_{16}$, C(O)R$_{14}$, C(O)OR$_{14}$, OR$_{14}$, SR$_{14}$, S(O)R$_{14}$, and S(O)$_2$R$_{14}$.

In some embodiments of any one of Formulae I, Ia, Ib, and Ic, $R_1$ is selected from the group consisting of $C_{6-10}$aryl and a 5- to 9-membered heteroaryl group having 1 to 4 heteroatoms groups as ring vertices independently selected from N, C(O), O, and S; and is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, NR$_{15}$C(O)R$_{14}$, NR$_{15}$C(O)OR$_{14}$, NR$_{14}$C(O)NR$_{15}$R$_{16}$, NR$_{15}$S(O)R$_{14}$, NR$_{15}$S(O)$_2$R$_{14}$, C(O)NR$_{15}$R$_{16}$, S(O)NR$_{15}$R$_{16}$, S(O)$_2$NR$_{15}$R$_{16}$, C(O)R$_{14}$, C(O)OR$_{14}$, OR$_{14}$, SR$_{14}$, S(O)R$_{14}$, and S(O)$_2$R$_{14}$; and R$_{14}$, R$_{18}$ and R$_{16}$ are each independently selected from the group consisting of hydrogen, $C_{1-4}$alkyl, $C_{3-8}$cycloalkyl, $C_{6-10}$aryl and 5-10 membered heteroaryl, each of which is optionally substituted by one or more groups independently selected from the group consisting of amido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

In some embodiments of any one of Formulae I, Ia, Ib, and Ic, $R_1$ is selected from the group consisting of $C_{6-10}$aryl and a 5- to 9-membered heteroaryl group having 1 to 4 heteroatoms groups as ring vertices independently selected from N, C(O), O, and S; and is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, NR$_{15}$C(O)R$_{14}$, NR$_{15}$C(O)OR$_{14}$, NR$_{14}$C(O)NR$_{15}$R$_{16}$, NR$_{15}$S(O)R$_{14}$, NR$_{15}$S(O)$_2$R$_{14}$, C(O)NR$_{15}$R$_{16}$, S(O)NR$_{15}$R$_{16}$, S(O)$_2$NR$_{15}$R$_{16}$, C(O)R$_{14}$, C(O)OR$_{14}$, OR$_{14}$, SR$_{14}$, S(O)R$_{14}$, and S(O)$_2$R$_{14}$; and R$_{14}$, R$_{15}$ and R$_{16}$ are each independently selected from the group consisting of hydrogen, $C_{1-4}$alkyl, $C_{3-8}$cycloalkyl, $C_{6-10}$aryl and 5-10 membered heteroaryl, each of which is optionally substituted by one or more groups independently selected from the group consisting of halo, hydroxy, cyano, and $C_{1-4}$alkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and OR$_{14}$.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and OR$_{14}$; and R$_{14}$ is selected from the group consisting of hydrogen, $C_{1-4}$alkyl, $C_{3-8}$cycloalkyl, $C_{6-10}$aryl and 5-10 membered heteroaryl, each of which is optionally substituted by one or more groups independently selected from the group consisting of amido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; and $R_{14}$ is selected from the group consisting of hydrogen, $C_{1-4}$alkyl, $C_{3-8}$cycloalkyl, $C_{6-10}$aryl and 5-10 membered heteroaryl, each of which is optionally substituted by one or more groups independently selected from the group consisting of halo, hydroxy, cyano, and $C_{1-4}$alkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; and $R_{14}$ is selected from the group consisting of $C_{6-10}$aryl and a 5-10 membered heteroaryl, each of which is optionally substituted by one or more groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; and $R_{14}$ is selected from the group consisting of $C_{6-10}$aryl and a 5-10 membered heteroaryl, each of which is optionally substituted by one or more groups independently selected from the group consisting of halo, hydroxy, cyano, and $C_{1-4}$alkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; and $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; and $R_{14}$ is phenyl or a 5-6 membered heteroaryl having 1 to 4 heteroatoms as ring vertices independently selected from N, O, and S, each of which is optionally substituted by one or more groups independently selected from the group consisting of halo, hydroxy, cyano, and $C_{1-4}$alkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; and $R_{14}$ is phenyl or a 5-6 membered heteroaryl having 1 to 4 heteroatoms as ring vertices independently selected from N, O, and S, each of which is optionally substituted by one or more groups independently selected from the group consisting of $C_{1-4}$alkylamido, halo, hydroxy, cyano, and $C_{1-4}$alkyl.

In some embodiments of any one of Formulae I, Ia, Ib, and Ic, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; and $R_{14}$ is phenyl or a 5-6 membered heteroaryl having 1 to 4 heteroatoms as ring vertices independently selected from N, O, and S, each of which is optionally substituted by one or more groups independently selected from the group consisting of $C_{1-4}$alkylamido and $C_{1-4}$alkyl.

In some embodiments of any one of Formulae I, Ia, Ib, and Ic, $R_1$ is phenyl or a 5- to 6-member heteroaryl group having 1 to 4 heteroatoms or groups as ring vertices independently selected from N, C(O), O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl.

In some embodiments of any one of Formulae I, Ia, Ib, and Ic, $R_2$, $R_3$, $R_{10}$, and Rut are independently hydrogen or $C_{1-4}$alkyl. In certain embodiments, $R_2$, $R_3$, $R_{10}$, and $R_{11}$ are each hydrogen.

In some embodiments of any one of Formulae I, Ia, Ib, and Ic, $R_4$, $R_5$, $R_8$, and $R_9$ are independently selected from the group consisting of hydrogen, $C_{1-4}$alkyl, $C_{1-4}$alkoxy, amino, hydroxy, $C_{3-8}$cycloalkyl, and $C_{1-4}$alkylamino. In certain embodiments, $R_4$, $R_5$, $R_8$, and $R_9$ are independently hydrogen or $C_{1-4}$alkyl. In certain embodiments, $R_4$, $R_5$, $R_8$, and $R_9$ are each hydrogen.

In some embodiments of any one of Formulae I, Ia, Ib, and Ic, $R_1$ is phenyl or a 5- to 6-member heteroaryl group having 1 to 4 heteroatoms or groups as ring vertices independently selected from N, C(O), O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; and $R_4$, $R_5$, $R_8$, and $R_9$ are independently selected from the group consisting of hydrogen, $C_{1-4}$alkyl, $C_{1-4}$alkoxy, amino, hydroxy, $C_{3-6}$cycloalkyl, and $C_{1-4}$alkylamino.

In some embodiments of any one of Formulae I, Ia, Ib, and Ic, $R_2$, $R_3$, $R_4$, $R_5$, $R_8$, $R_9$, $R_{10}$ and $R_{11}$ are each hydrogen.

In some embodiments, the compound is represented by Formula II:

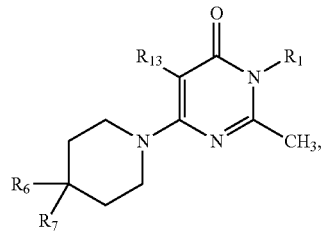

(II)

wherein $R_1$, $R_6$, $R_7$, and $R_{13}$ are as defined and described herein.

In some embodiments of any one of Formulae I, Ia-Ic, and II, $R_6$ is selected from the group consisting of amino, $C_{1-4}$aminoalkyl, and $C_{1-4}$alkylamino; and $R_7$ is selected from the group consisting of hydrogen, amido, cyano, halo, and hydroxy, or is selected from the group consisting of $C_{1-4}$alkyl, $C_{1-4}$hydroxyalkyl, $C_{3-6}$cycloalkyl, phenyl, and 5- or 6-membered heteroaryl, any of which is optionally substituted with one to three substituents selected from the group consisting of amino, halo, hydroxy, cyano, trifluoromethyl, trifluoromethoxy, $C_{1-4}$alkyl, and $C_{1-4}$alkoxy. In some embodiments, $R_6$ is selected from the group consisting of amino, $C_{1-4}$aminoalkyl, and $C_{1-4}$alkylamino; and $R_7$ is selected from the group consisting of hydrogen, amido, halo, and hydroxy, or is selected from the group consisting of $C_{1-4}$alkyl, $C_{1-4}$hydroxyalkyl, $C_{3-6}$cycloalkyl, phenyl, and 5- or 6-membered heteroaryl, any of which is optionally substituted with one or two substituents selected from the group consisting of amino, halo, hydroxy, cyano, trifluoromethyl, trifluoromethoxy, $C_{1-4}$alkyl, and $C_{1-4}$alkoxy.

In some embodiments of any one of Formulae I, Ia-Ic, and II, $R_6$ is selected from the group consisting of amino, $C_{1-4}$aminoalkyl, and methylamino. In some embodiments, $R_6$ is amino or $C_{1-4}$aminoalkyl. In certain embodiments, $R_6$ is amino, aminomethyl, or methylamino. In certain embodiments, $R_6$ is amino or aminomethyl. In certain embodiments, $R_6$ is amino. In certain embodiments, $R_6$ is aminomethyl.

In some embodiments of any one of Formulae I, Ia-Ic, and II, $R_7$ is selected from the group consisting of hydroxy, $C_{1-4}$alkyl, $C_{1-4}$hydroxyalkyl, $C_{3-6}$cycloalkyl, phenyl, and 5- or 6-membered heteroaryl, any of which is optionally substituted with one or two groups selected from the group consisting of amino, halo, hydroxy, cyano, trifluoromethyl, trifluoromethoxy, $C_{1-4}$alkyl, and $C_{1-4}$alkoxy. In some embodiments, $R_7$ is selected from the group consisting of hydroxy, $C_{1-4}$alkyl, $C_{1-4}$hydroxyalkyl, $C_{3-6}$cycloalkyl, phenyl, and 5- or 6-membered heteroaryl. In some embodiments, $R_7$ is hydroxy, $C_{1-4}$alkyl, or $C_{1-4}$hydroxyalkyl. In certain embodiments, $R_7$ is $C_{1-4}$alkyl. In certain embodiments, $R_7$ is methyl. In certain embodiments, $R_7$ is ethyl.

In some embodiments of any one of Formulae I, Ia-Ic, and II, $R_6$ is $C_{1-4}$aminoalkyl; and $R_7$ is selected from the group consisting of hydroxy, $C_{1-4}$alkyl, $C_{1-4}$hydroxyalkyl, $C_{3-6}$cycloalkyl, phenyl, and 5- or 6-membered heteroaryl, any of which is optionally substituted with one to three groups independently selected from the group consisting of amino, halo, hydroxy, cyano, trifluoromethyl, trifluoromethoxy, $C_{1-4}$alkyl, and $C_{1-4}$alkoxy.

In some embodiments of any one of Formulae I, Ia-Ic, and II, $R_6$ is aminomethyl; and $R_7$ is selected from the group consisting of hydroxy, $C_{1-4}$alkyl, $C_{1-4}$hydroxyalkyl, $C_{3-6}$cycloalkyl, phenyl, and 5- or 6-membered heteroaryl.

In some embodiments of any one of Formulae I, Ia-Ic, and II, $R_6$ is amino; and $R_7$ is selected from the group consisting of hydroxy, $C_{1-4}$alkyl, $C_{1-4}$hydroxyalkyl, $C_{3-6}$cycloalkyl, phenyl, and 5- or 6-membered heteroaryl, any of which is optionally substituted with one to three groups independently selected from the group consisting of amino, halo, hydroxy, cyano, trifluoromethyl, trifluoromethoxy, $C_{1-4}$alkyl, and $C_{1-4}$alkoxy.

In some embodiments of any one of Formulae I, Ia-Ic, and II, $R_6$ is amino; and $R_7$ is selected from the group consisting of hydroxy, $C_{1-4}$alkyl, $C_{1-4}$hydroxyalkyl, $C_{3-6}$cycloalkyl, phenyl, and 5- or 6-membered heteroaryl.

In some embodiments of any one of Formulae I, Ia-Ic, and II, $R_6$ is amino; and $R_7$ is $C_{1-4}$hydroxyalkyl. In some embodiments, $R_6$ is amino; and $R_7$ is hydroxymethyl. In some embodiments, $R_6$ is amino; and $R_7$ is $C_{1-4}$alkyl. In certain embodiments, $R_6$ is amino; and $R_7$ is methyl. In some embodiments, $R_6$ is amino; and $R_7$ is ethyl. In some embodiments, $R_6$ is aminomethyl; and $R_7$ is $C_{1-4}$alkyl. In certain embodiments, $R_6$ is aminomethyl; and $R_7$ is methyl. In some embodiments, $R_6$ is aminomethyl; and $R_7$ is ethyl.

In any of the above embodiments, the amido of $R_7$ may specifically be —C(O)NH$_2$.

In some embodiments of any one of Formulae I, Ia-Ic, and II, $R_6$ and $R_7$ together with the carbon atom to which they are both attached form a 3- to 7-membered saturated or unsaturated ring having 1 to 3 heteroatoms or groups as ring vertices independently selected from N, C(O), O, and S(O)$_m$, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_6$ and $R_7$ together with the carbon atom to which they are both attached form a 4- to 6-membered saturated or unsaturated ring having 1 to 3 heteroatoms or groups as ring vertices independently selected from N, C(O), and O, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_6$ and $R_7$ together with the carbon atom to which they are both attached form a 3- to 7-membered saturated ring having 1 to 3 heteroatoms or groups as ring vertices independently selected from N, C(O), O, and S(O)$_m$, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_6$ and $R_7$ together with the carbon atom to which they are both attached form a 4- to 6-membered saturated ring having 1 to 3 heteroatoms or groups as ring vertices independently selected from N, C(O), and O, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_6$ and $R_7$ together with the carbon atom to which they are both attached form a 4- to 6-membered saturated ring having 1 to 3 heteroatoms or groups as ring vertices independently selected from N and O, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_6$ and $R_7$ together with the carbon atom to which they are both attached form a 3- to 7-membered cycloalkyl ring that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_6$ and $R_7$ together with the carbon atom to which they are both attached form a 4- to 6-membered cycloalkyl ring that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl; $R_6$ is selected from the group consisting of amino, $C_{1-4}$aminoalkyl, and $C_{1-4}$alkylamino; and $R_7$ is selected from the group consisting of hydrogen, halo, and hydroxy, or is selected from the group consisting of amido, $C_{1-4}$alkyl, $C_{1-4}$hydroxyalkyl, $C_{3-6}$cycloalkyl, phenyl, and 5- or 6-membered heteroaryl, any of which is optionally substituted with one or two substituents selected from the group consisting of amino, halo, hydroxy, cyano, trifluoromethyl, trifluoromethoxy, $C_{1-4}$alkyl, and $C_{1-4}$alkoxy.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl; $R_6$ is amino or aminomethyl; and $R_7$ is selected from the group consisting of hydroxy, $C_{1-4}$alkyl, and $C_{1-4}$hydroxyalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl; and $R_6$ and $R_7$ together with the carbon atom to which they are both attached form a 3- to 7-membered saturated or unsaturated ring having 1 to 3 heteroatoms or groups as ring vertices independently selected from N, C(O), O, and $S(O)_m$, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl; and $R_6$ and $R_7$ together with the carbon atom to which they are both attached form a 4- to 6-membered saturated or unsaturated ring having 1 to 3 heteroatoms or groups as ring vertices independently selected from N, C(O), and O, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$; $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl; and $R_6$ and $R_7$ together with the carbon atom to which they are both attached form a 3- to 7-membered cycloalkyl ring that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; $R_6$ is selected from the group consisting of amino, $C_{1-4}$aminoalkyl, and $C_{1-4}$alkylamino; and $R_7$ is selected from the group consisting of hydrogen, halo, and hydroxy, or is selected from the group consisting of amido, $C_{1-4}$alkyl, $C_{1-4}$hydroxyalkyl, $C_{3-6}$cycloalkyl, phenyl, and 5- or 6-membered heteroaryl, any of which is optionally substituted with one or two substituents selected from the group consisting of amino, halo, hydroxy, cyano, trifluoromethyl, trifluoromethoxy, $C_{1-4}$alkyl, and $C_{1-4}$alkoxy.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; $R_6$ is amino or aminomethyl; and $R_7$ is selected from the group consisting of hydroxy, $C_{1-4}$alkyl, and $C_{1-4}$hydroxyalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; and $R_6$ and $R_7$ together with the carbon atom to which they are both attached form a 3- to 7-membered saturated or unsaturated ring having 1 to 3 heteroatoms or groups as ring vertices independently selected from N, C(O), O, and S(O)$_m$, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; and $R_6$ and $R_7$ together with the carbon atom to which they are both attached form a 4- to 6-membered saturated or unsaturated ring having 1 to 3 heteroatoms or groups as ring vertices independently selected from N, C(O), and O, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; and $R_6$ and $R_7$ together with the carbon atom to which they are both attached form a 3- to 7-membered cycloalkyl ring that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

In some embodiments of any one of Formulae I, Ia-Ic, and II, $R_1$ is selected from the group consisting of phenyl, pyridyl, pyrimidinyl, pyrazolyl, pyrazinyl, pyridazinyl, and 1,2,4-triazinyl; and is optionally substituted with 1, 2, or 3 $R_{12}$, wherein each $R_{12}$ is as defined and described herein, In some embodiments, $R_1$ is selected from the group consisting of phenyl, pyridyl, pyrimidinyl, pyrazinyl, pyridazinyl, and 1,2,4-triazinyl; and is optionally substituted with 1, 2, or 3 $R_{12}$, wherein each $R_{12}$ is as defined and described herein. In some embodiments, $R_1$ is phenyl or pyridyl; and is optionally substituted with 1, 2, or 3 $R_{12}$, wherein each $R_{12}$ is as defined and described herein.

In some embodiments of any one of Formulae I, Ia-Ic, and II, $R_1$ is selected from the group consisting of phenyl, pyridyl, pyrimidinyl, pyrazinyl, pyridazinyl, and 1,2,4-triazinyl; and is optionally substituted with 1, 2, or 3 $R_{12}$ independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$.

In some embodiments of any one of Formulae I, Ia-Ic, and II, $R_1$ is selected from the group consisting of phenyl, pyridyl, pyrimidinyl, pyrazinyl, pyridazinyl, and 1,2,4-triazinyl; and is optionally substituted with 1, 2, or 3 $R_{12}$ independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl.

In some embodiments of any one of Formulae I, Ia-Ic, and II, $R_1$ is phenyl or pyridyl, each of which is optionally substituted with 1, 2, or 3 $R_{12}$ independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$.

In some embodiments of any one of Formulae I, Ia-Ic, and II, $R_1$ is phenyl or pyridyl, each of which is optionally substituted with 1, 2, or 3 $R_{12}$ independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl.

In some embodiments of any one of Formulae I, Ia-Ic, and II, $R_1$ is phenyl and is optionally substituted with 1-3 $R_{12}$, each of which is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$. In some embodiments, $R_1$ is phenyl and is optionally substituted with 1-3 $R_{12}$, each of which is independently selected from the group consisting of halo, hydroxy, amino, methylamino, dimethylamino, cyano, $C_{1-4}$alkyl, $C_{1-4}$haloalkyl, and $C_{1-4}$alkoxy. In some embodiments, $R_1$ is phenyl and is optionally substituted with 1-3 $R_{12}$, each of which is independently selected from the group consisting of halo, hydroxy, $C_{1-4}$alkyl, and $C_{1-4}$alkoxy.

In some embodiments of any one of Formulae I, Ia-Ic, and II, $R_1$ is pyridyl and is optionally substituted with 1-3 $R_{12}$, each of which is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$. In some embodiments, $R_1$ is pyridyl and is optionally substituted with 1-3 $R_{12}$, each of which is independently selected from the group consisting of halo, hydroxy, amino, methylamino, dimethylamino, cyano, $C_{1-4}$alkyl, $C_{1-4}$haloalkyl, and $C_{1-4}$alkoxy. In some embodiments, $R_1$ is pyridyl and is optionally substituted with 1-3 $R_{12}$, each of which is independently selected from the group consisting of halo, hydroxy, $C_{1-4}$alkyl, and $C_{1-4}$alkoxy.

In some embodiments of any one of Formulae I, Ia-Ic, and II, $R_1$ is selected from the group consisting of:

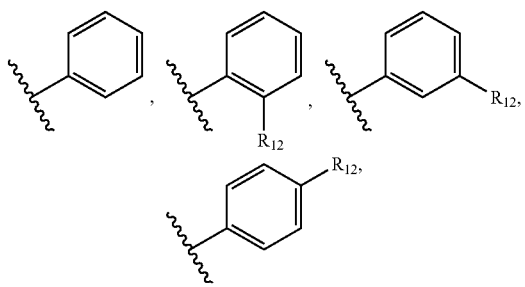

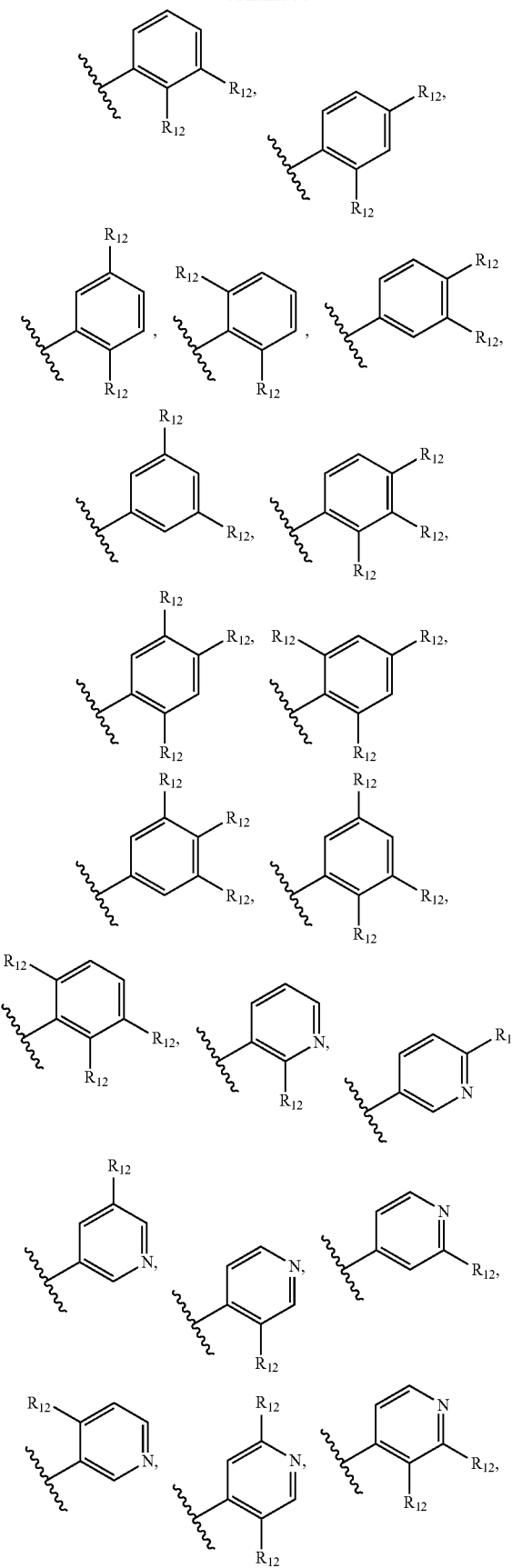
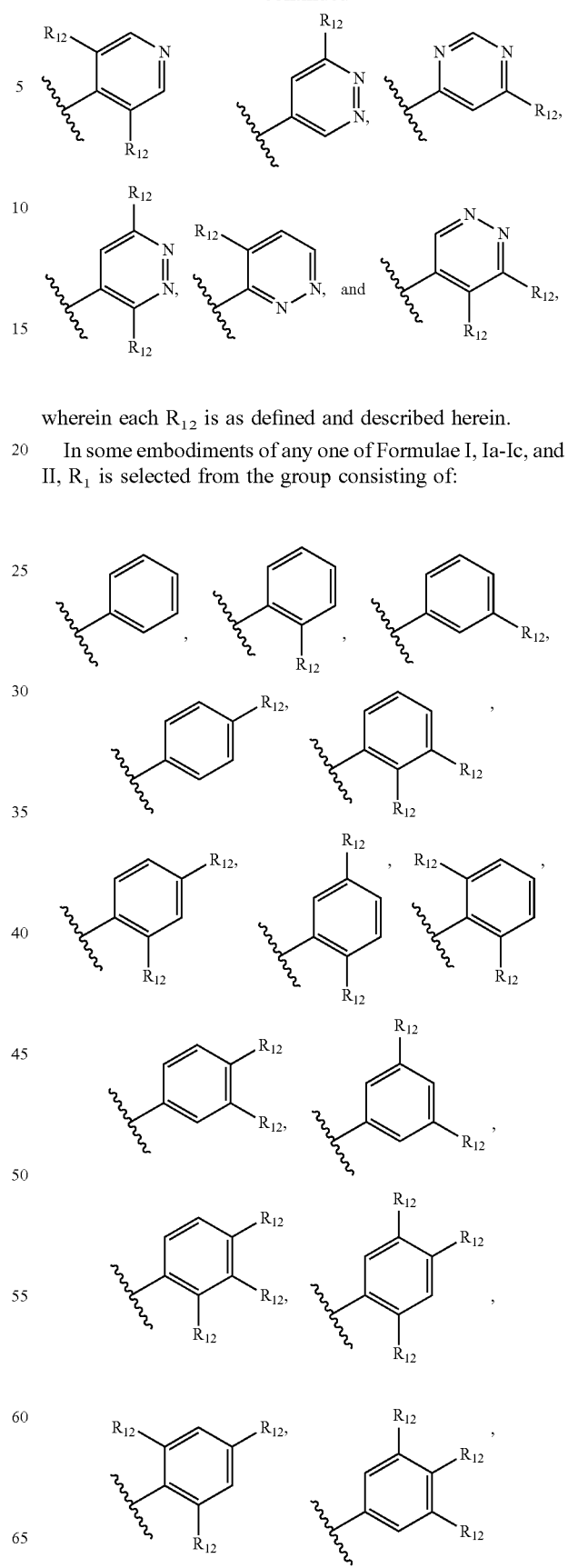
wherein each $R_{12}$ is as defined and described herein.
In some embodiments of any one of Formulae I, Ia-Ic, and II, $R_1$ is selected from the group consisting of:

-continued

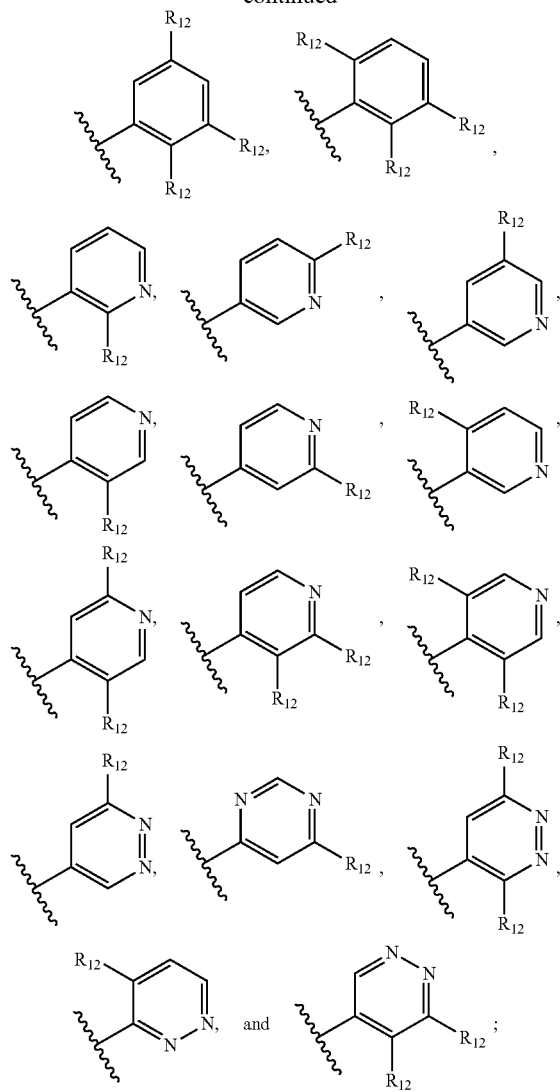

and each $R_{12}$ is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$, wherein $R_{14}$ is as defined and described herein.

In some embodiments of any one of Formulae I, Ia-Ic, and II, $R_1$ is selected from the group consisting of:

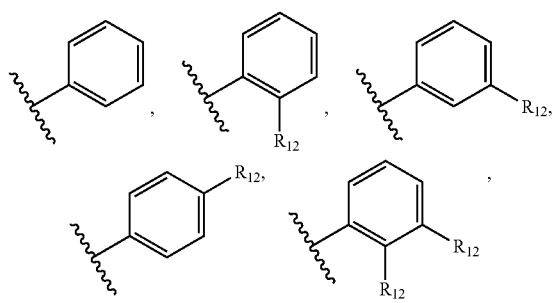

-continued

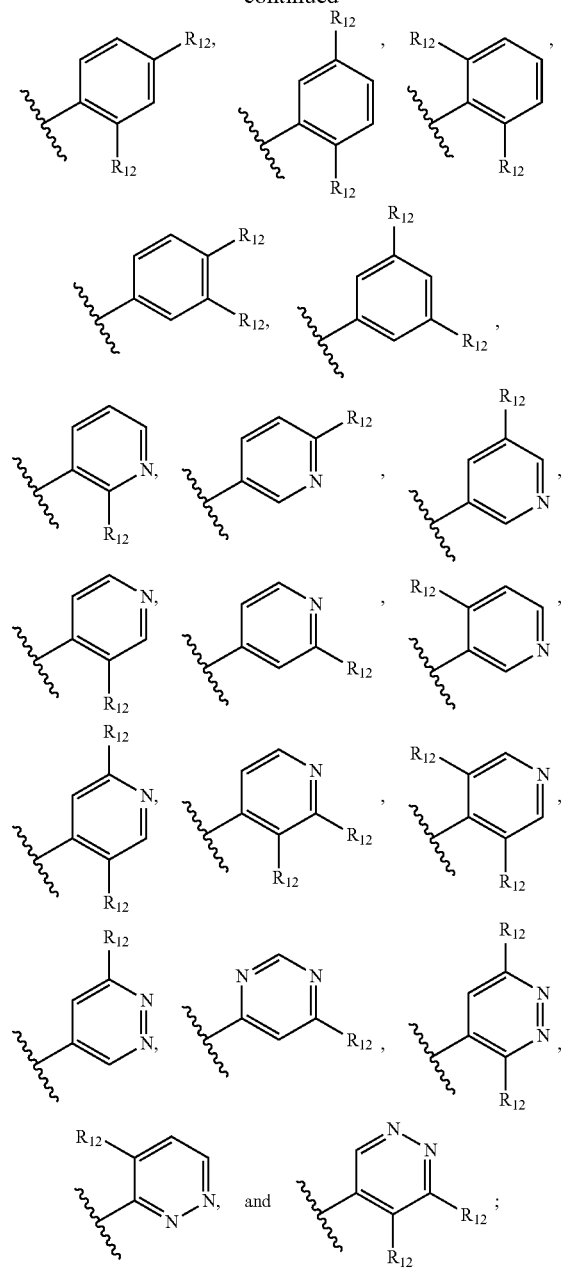

and each $R_{12}$ is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl.

In some embodiments of any one of Formulae I, Ia-Ic, and II, $R_1$ is selected from the group consisting of:

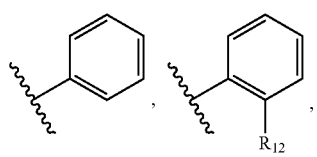

-continued

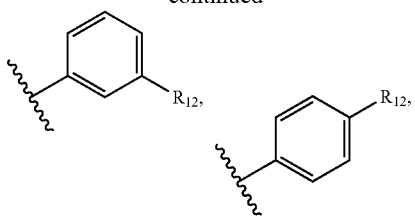
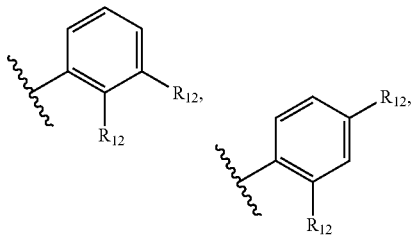
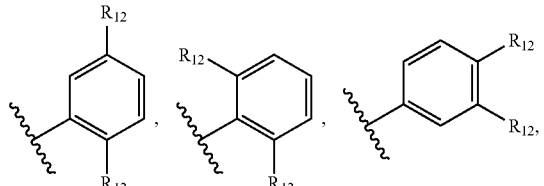
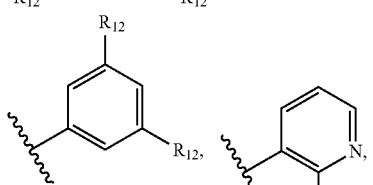
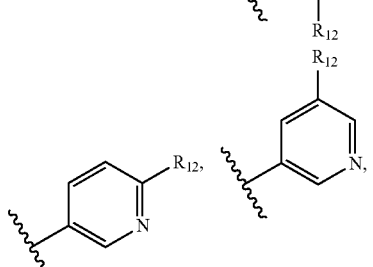
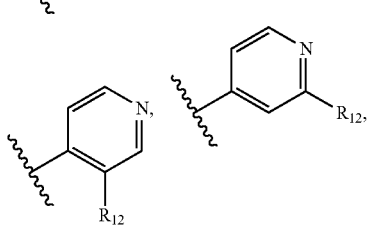
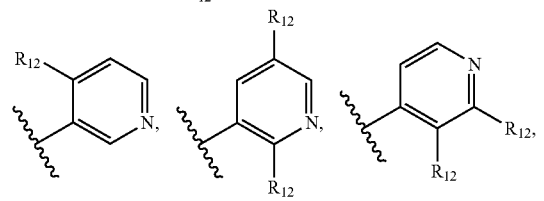
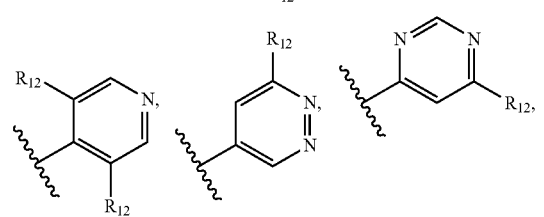

-continued

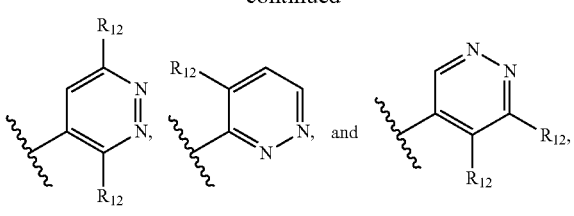

and each $R_{12}$ is independently selected from the group consisting of halo, hydroxy, amino, methylamino, dimethylamino, cyano, $C_{1-4}$alkyl, $C_{1-4}$haloalkyl, and $C_{1-4}$alkoxy.

In some embodiments of any one of Formulae I, Ia-Ic, and II, $R_1$ is selected from the group consisting of:

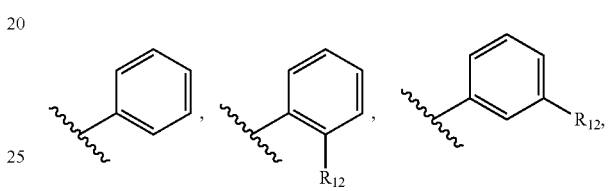
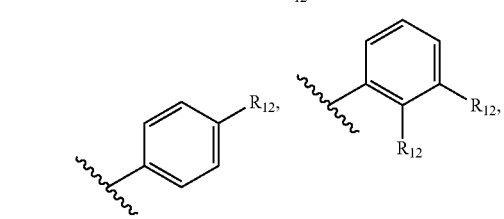
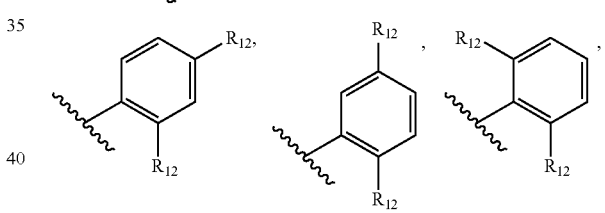
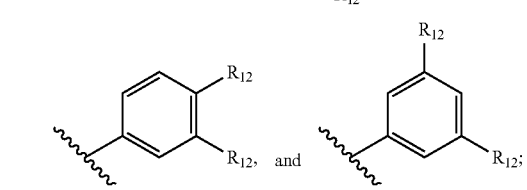

and each $R_{12}$ is independently selected from the group consisting of halo, hydroxy, amino, methylamino, dimethylamino, cyano, $C_{1-4}$alkyl, $C_{1-4}$haloalkyl, and $C_{1-4}$alkoxy.

In some embodiments of any one of Formulae I, Ia-Ic, and II, $R_1$ is selected from the group consisting of:

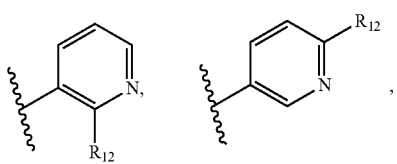

33

-continued

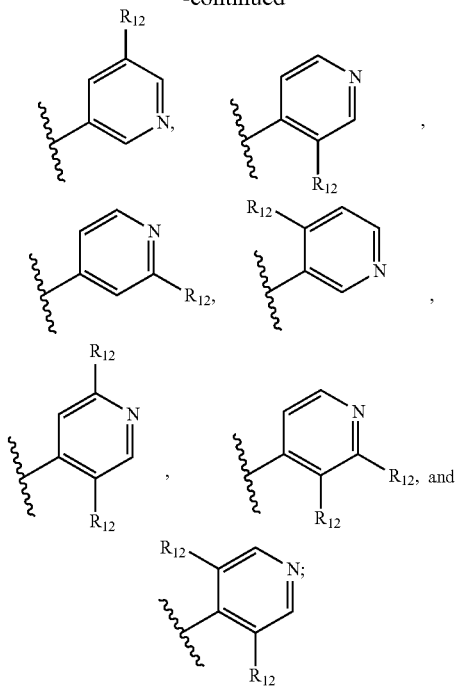

and each $R_{12}$ is independently selected from the group consisting of halo, hydroxy, amino, methylamino, dimethylamino, cyano, $C_{1-4}$alkyl, $C_{1-4}$haloalkyl, and $C_{1-4}$alkoxy.

In some embodiments of any one of Formulae I, Ia-Ic, and II, each $R_{12}$ is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$. In some embodiments, each $R_{12}$ is independently selected from the group consisting of halo, $C_{1-4}$alkyl, $C_{1-4}$alkoxy, $C_{1-4}$haloalkyl, and $OR_{14}$. In some embodiments, each $R_{12}$ is independently selected from the group consisting of halo, hydroxy, amino, methylamino, dimethylamino, cyano, $C_{1-4}$alkyl, $C_{1-4}$haloalkyl, and $C_{1-4}$alkoxy. In some embodiments, each $R_{12}$ is independently selected from the group consisting of halo, $C_{1-4}$alkyl, $C_{1-4}$alkoxy, and $C_{1-4}$haloalkyl. In some embodiments, each $R_{12}$ is independently selected from the group consisting of F, Cl, Br, $CH_3$, $OCH_3$, and $CF_3$.

In some embodiments of any one of Formulae I, Ia-Ic, and II, each $R_{12}$ is independently selected from the group consisting of F, Cl, Br, $CH_3$, $OCH_3$, $CF_3$,

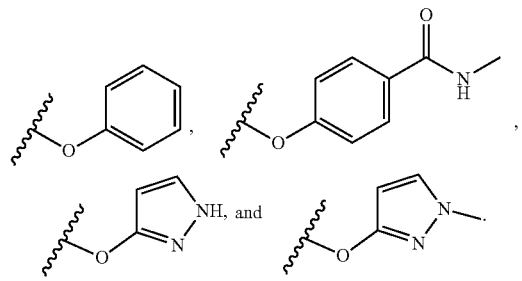

34

In some embodiments of any one of Formulae I, Ia-Ic, and II, $R_1$ is selected from the group consisting of:

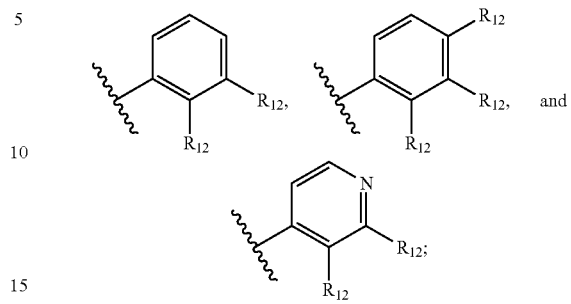

and each $R_{12}$ is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$, wherein $R_{14}$ is as defined and described herein.

In some embodiments of any one of Formulae I, Ia-Ic, and II, $R_1$ is represented by:

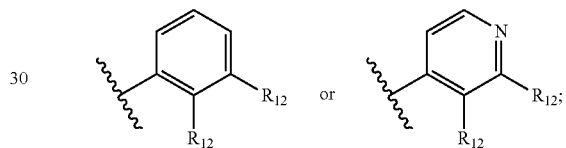

and each $R_{12}$ is independently selected from the group consisting of halo, $C_{1-4}$alkyl, $C_{1-4}$alkoxy, and $C_{1-4}$haloalkyl. In some embodiments, each $R_{12}$ is independently selected from the group consisting of F, Cl, Br, $CH_3$, $OCH_3$, and $CF_3$. In some embodiments, each $R_{12}$ is Cl.

In some embodiments of any one of Formulae I, Ia-Ic, and II, $R_1$ is represented by:

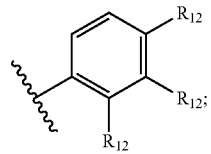

and each $R_{12}$ is independently selected from the group consisting of halo, $C_{1-4}$alkyl, $C_{1-4}$alkoxy, and $C_{1-4}$haloalkyl. In some embodiments, each $R_{12}$ is independently selected from the group consisting of F, Cl, Br, $CH_3$, $OCH_3$, and $CF_3$. In some embodiments, each $R_{12}$ is independently Cl or Br.

In some embodiments of any one of Formulae I, Ia-Ic, and II, $R_{14}$ is independently selected from the group consisting of $C_{6-10}$aryl and a 5-10 membered heteroaryl, each of which is optionally substituted by one or more groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl. In some embodiments, $R_{14}$ is independently selected from the group consisting of $C_{6-10}$aryl and a 5-10 membered heteroaryl, each of which is optionally substituted by one or two groups independently selected from the group consisting of $C_{1-4}$alkylamido, halo, hydroxy, cyano, and $C_{1-4}$alkyl. In some embodiments, $R_{14}$ is independently selected from the group consisting of $C_{6-10}$aryl and a 5-10 membered heteroaryl, each of which is optionally substituted by one or two groups independently selected from the group consisting of halo, hydroxy, cyano, and $C_{1-4}$alkyl.

In some embodiments of any one of Formulae I, Ia-Ic, and II, $R_{14}$ is independently phenyl or a 5-6 membered heteroaryl having 1 to 4 heteroatoms as ring vertices independently selected from N, O, and S, each of which is optionally substituted by one or more groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl. In some embodiments, $R_{14}$ is independently phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, halo, hydroxy, cyano, and $C_{1-4}$alkyl. In some embodiments, $R_{14}$ is independently phenyl or a 5-6 membered heteroaryl having 1 to 4 heteroatoms as ring vertices independently selected from N, O, and S, each of which is optionally substituted by one or two groups independently selected from the group consisting of halo, hydroxy, cyano, and $C_{1-4}$alkyl.

In some embodiments of any one of Formulae I, Ia-Ic, and II, $R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl. In some embodiments, $R_{14}$ is phenyl, optionally substituted by one or two groups independently selected from the group consisting of $C_{1-4}$alkylamido, halo, hydroxy, cyano, and $C_{1-4}$alkyl. In some embodiments, $R_{14}$ is phenyl, substituted with $C_{1-4}$alkylamido. In some embodiments, $R_{14}$ is phenyl substituted with —C(O)NHMe. In some embodiments, $R_{14}$ is phenyl. In some embodiments, $R_{14}$ is pyrazolyl, optionally substituted by one or two groups independently selected from the group consisting of $C_{1-4}$alkylamido, halo, hydroxy, cyano, and $C_{1-4}$alkyl. In some embodiments, $R_{14}$ is pyrazolyl substituted with $C_{1-4}$alkyl. In some embodiments, $R_{14}$ is pyrazolyl substituted with methyl. In some embodiments, $R_{14}$ is N-methylpyrazolyl. In some embodiments, $R_{14}$ is pyrazolyl.

In some embodiments of any one of Formulae I, Ia-Ic, and II, $R_1$ is represented by:

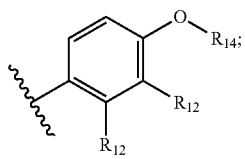

each $R_{12}$ is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; and $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, halo, hydroxy, cyano, and $C_{1-4}$alkyl.

In some embodiments of any one of Formulae I, Ia-Ic, and II, $R_1$ is represented by:

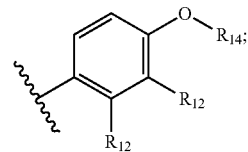

each $R_{12}$ is independently selected from the group consisting of halo, $C_{1-4}$alkyl, $C_{1-4}$alkoxy, $C_{1-4}$haloalkyl, and $OR_{14}$; and $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, halo, hydroxy, cyano, and $C_{1-4}$alkyl.

In some embodiments of any one of Formulae I, Ia-Ic, and II, $R_1$ is represented by:

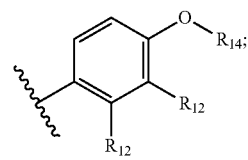

each $R_{12}$ is independently selected from the group consisting of halo, $C_{1-4}$alkyl, $C_{1-4}$alkoxy, $C_{1-4}$haloalkyl, and $OR_{14}$; and $R_{14}$ is selected from the group consisting of phenyl or pyrazolyl, each of which is optionally substituted by one or two groups independently selected from the group consisting of $C_{1-4}$alkylamido, halo, hydroxy, cyano, and $C_{1-4}$alkyl.

In some embodiments of any one of Formulae I, Ia-Ic, and II, $R_1$ is represented by:

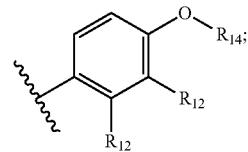

each $R_{12}$ is independently selected from the group consisting of halo, $C_{1-4}$alkyl, $C_{1-4}$alkoxy, $C_{1-4}$haloalkyl, and $OR_{14}$; and $R_{14}$ is selected from the group consisting of phenyl, phenyl substituted with $C_{1-4}$alkylamido, pyrazolyl, and pyrazolyl substituted with $C_{1-4}$alkyl. In some embodiments, each $R_{12}$ is independently selected from the group consisting of F, Cl, Br, $CH_3$, $OCH_3$, and $CF_3$; and $R_{14}$ is selected from the group consisting of phenyl, MeNHC(O)-phenyl, pyrazolyl, and N-methylpyrazolyl. In some embodiments, each $R_{12}$ is Cl; and $R_{14}$ is selected from the group consisting of phenyl, MeNHC(O)-phenyl, pyrazolyl, and N-methylpyrazolyl.

In certain embodiments, the compound is represented by Formula II:

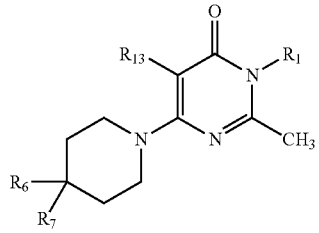

(II)

or a salt, ester or prodrug thereof, wherein:
- $R_1$ is phenyl or pyridyl, each of which is substituted with 0 to 3 $R_{12}$;
- each $R_{12}$ is independently selected from the group consisting of halo, hydroxy, $C_{1-4}$alkyl, $C_{1-4}$alkoxy, $C_{1-4}$haloalkyl, and $OR_{14}$;
- $R_6$ is selected from the group consisting of amino, $C_{1-4}$aminoalkyl, and $C_{1-4}$alkylamino;
- $R_7$ is selected from the group consisting of hydrogen, cyano, amido, halo, and hydroxy, or is selected from the group consisting of $C_{1-4}$alkyl, $C_{1-4}$hydroxyalkyl, $C_{3-6}$cycloalkyl, phenyl, and 5- or 6-membered heteroaryl, any of which is optionally substituted with one to three substituents independently selected from the group consisting of amino, halo, hydroxy, cyano, trifluoromethyl, trifluoromethoxy, $C_{1-4}$alkyl, and $C_{1-4}$alkoxy;
- $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl; and
- $R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl.

In certain embodiments, the compound is represented by Formula III:

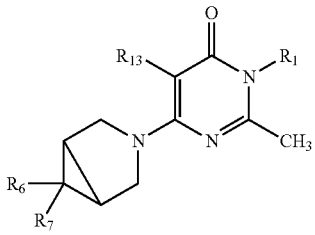

(III)

or a salt, ester or prodrug thereof, wherein:
- $R_1$ is phenyl or pyridyl, each of which is substituted with 0 to 3 $R_{12}$;
- each $R_{12}$ is independently selected from the group consisting of halo, hydroxy, $C_{1-4}$alkyl, $C_{1-4}$alkoxy, $C_{1-4}$haloalkyl, and $OR_{14}$;
- $R_6$ is selected from the group consisting of amino, $C_{1-4}$aminoalkyl, and $C_{1-4}$alkylamino;
- $R_7$ is selected from the group consisting of hydrogen, cyano, amido, halo, and hydroxy, or is selected from the group consisting of $C_{1-4}$alkyl, $C_{1-4}$hydroxyalkyl, $C_{3-6}$cycloalkyl, phenyl, and 5- or 6-membered heteroaryl, any of which is optionally substituted with one to three substituents independently selected from the group consisting of amino, halo, hydroxy, cyano, trifluoromethyl, trifluoromethoxy, $C_{1-4}$alkyl, and $C_{1-4}$alkoxy;
- $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl; and
- $R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl.

In certain embodiments, the compound is represented by Formula IV:

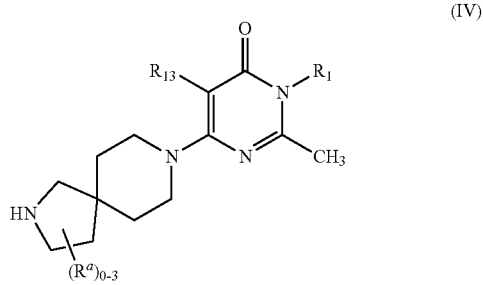

(IV)

or a salt, ester or prodrug thereof, wherein:
- $R_1$ is phenyl or pyridyl, each of which is substituted with 0 to 3 $R_{12}$;
- each $R_{12}$ is independently selected from the group consisting of halo, hydroxy, $C_{1-4}$alkyl, $C_{1-4}$alkoxy, $C_{1-4}$haloalkyl, and $OR_{14}$;
- $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;
- $R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and
- each $R^a$ is independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

In certain embodiments, the compound is represented by Formula V:

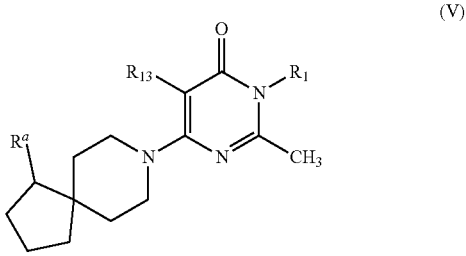

(V)

or a salt, ester or prodrug thereof, wherein:
- $R_1$ is phenyl or pyridyl, each of which is substituted with 0 to 3 $R_{12}$;
- each $R_{12}$ is independently selected from the group consisting of halo, hydroxy, $C_{1-4}$alkyl, $C_{1-4}$alkoxy, $C_{1-4}$haloalkyl, and $OR_{14}$; and $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;

$R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and $R^a$ is selected from the group consisting of amino, halo, hydroxy, cyano, trifluoromethyl, trifluoromethoxy, $C_{1-4}$alkyl, and $C_{1-4}$alkoxy.

In certain embodiments, the compound is represented by Formula VI:

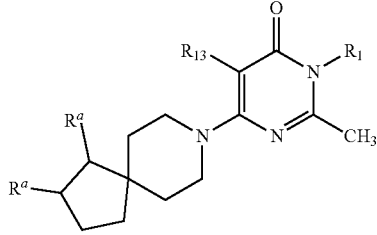

(VI)

or a salt, ester or prodrug thereof, wherein:

$R_1$ is phenyl or pyridyl, each of which is substituted with 0 to 3 $R_{12}$;

each $R_{12}$ is independently selected from the group consisting of halo, hydroxy, $C_{1-4}$alkyl, $C_{1-4}$alkoxy, $C_{1-4}$haloalkyl, and $OR_{14}$; and $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;

$R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and each $R^a$ is independently selected from the group consisting of amino, halo, hydroxy, cyano, trifluoromethyl, trifluoromethoxy, $C_{1-4}$alkyl, and $C_{1-4}$alkoxy.

In certain embodiments, the compound is represented by Formula VII:

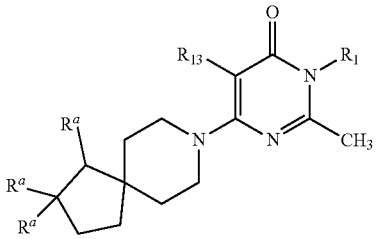

(VII)

or a salt, ester or prodrug thereof, wherein:

$R_1$ is phenyl or pyridyl, each of which is substituted with 0 to 3 $R_{12}$;

each $R_{12}$ is independently selected from the group consisting of halo, hydroxy, $C_{1-4}$alkyl, $C_{1-4}$alkoxy, $C_{1-4}$haloalkyl, and $OR_{14}$; and $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;

$R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and each $R^a$ is independently selected from the group consisting of amino, halo, hydroxy, cyano, trifluoromethyl, trifluoromethoxy, $C_{1-4}$alkyl, and $C_{1-4}$alkoxy.

In certain embodiments, the compound is represented by Formula VIII:

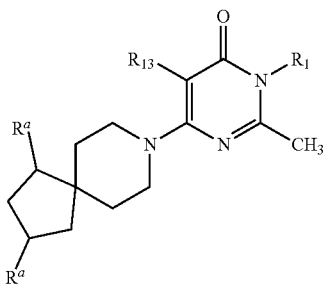

(VIII)

or a salt, ester or prodrug thereof, wherein:

$R_1$ is phenyl or pyridyl, each of which is substituted with 0 to 3 $R_{12}$;

each $R_{12}$ is independently selected from the group consisting of halo, hydroxy, $C_{1-4}$alkyl, $C_{1-4}$alkoxy, $C_{1-4}$haloalkyl, and $OR_{14}$; and $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;

$R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and each $R^a$ is independently selected from the group consisting of amino, halo, hydroxy, cyano, trifluoromethyl, trifluoromethoxy, $C_{1-4}$alkyl, and $C_{1-4}$alkoxy.

In certain embodiments, the compound is represented by Formula IX:

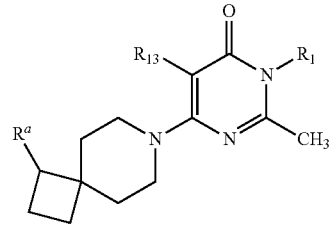

(IX)

or a salt, ester or prodrug thereof, wherein:

$R_1$ is phenyl or pyridyl, each of which is substituted with 0 to 3 $R_{12}$;

each $R_{12}$ is independently selected from the group consisting of halo, hydroxy, $C_{1-4}$alkyl, $C_{1-4}$alkoxy, $C_{1-4}$haloalkyl, and $OR_{14}$; and $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;

$R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and $R^a$ is selected from the group consisting of amino, halo, hydroxy, cyano, trifluoromethyl, trifluoromethoxy, $C_{1-4}$alkyl, and $C_{1-4}$alkoxy.

In certain embodiments, the compound is represented by Formula X:

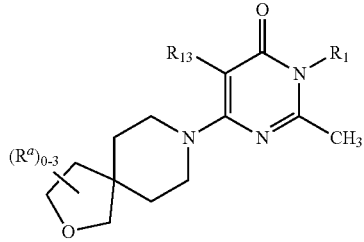

(X)

or a salt, ester or prodrug thereof, wherein:

$R_1$ is phenyl or pyridyl, each of which is substituted with 0 to 3 $R_{12}$;

each $R_{12}$ is independently selected from the group consisting of halo, hydroxy, $C_{1-4}$alkyl, $C_{1-4}$alkoxy, $C_{1-4}$haloalkyl, and $OR_{14}$; and $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;

$R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and each $R^a$ is independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

In certain embodiments, the compound is represented by Formula XI:

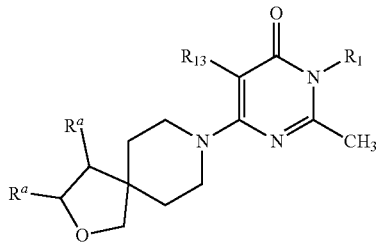

(XI)

or a salt, ester or prodrug thereof, wherein:

$R_1$ is phenyl or pyridyl, each of which is substituted with 0 to 3 $R_{12}$;

each $R_{12}$ is independently selected from the group consisting of halo, hydroxy, $C_{1-4}$alkyl, $C_{1-4}$alkoxy, $C_{1-4}$haloalkyl, and $OR_{14}$; and $R_{13}$ is selected from the group consisting of hydrogen, halo, cyano, $C_{1-4}$alkyl, $C_{1-6}$haloalkyl, $C_{1-6}$hydroxyalkyl, $C_{1-6}$dihydroxyalkyl, and $C_{3-8}$cycloalkyl;

$R_{14}$ is phenyl or pyrazolyl, each of which is optionally substituted by one or two groups independently selected from the group consisting of $C_{1-4}$alkylamido, halo, hydroxy, cyano, and $C_{1-4}$alkyl; and each $R^a$ is independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

In some embodiment of any one of Formulae II-XI, $R_1$, $R_6$, $R_7$, $R_{12}$, $R_{13}$, and $R_{14}$ may have the meanings set forth in any one or more of the selected embodiments noted above.

In some embodiments of any one of Formulae II-XI, $R_{13}$ is selected from the group consisting of hydrogen, halo, $C_{1-6}$alkyl, $C_{1-6}$haloalkyl, $C_{1-6}$hydroxyalkyl, $C_{1-6}$dihydroxyalkyl, and $C_{3-8}$cycloalkyl. In some embodiments, $R_{13}$ is selected from the group consisting of hydrogen, halo, $C_{1-6}$alkyl, and $C_{1-6}$haloalkyl. In some embodiments, $R_{13}$ is selected from the group consisting of hydrogen, halo, $C_{1-4}$alkyl, and $C_{1-4}$haloalkyl. In some embodiments, $R_{13}$ is selected from the group consisting of hydrogen, Cl, Br, methyl, and $CF_3$. In some embodiments, $R_{13}$ is hydrogen. In some embodiments, $R_{13}$ is Cl. In some embodiments, $R_{13}$ is Br. In some embodiments, $R_{13}$ is methyl. In some embodiments, $R_{13}$ is $CF_3$.

In some embodiments of any one of Formulae II-XI, $R_1$ is phenyl or pyridyl, each of which is substituted with 1 to 3 $R_{12}$. In some embodiments, $R_1$ is phenyl or pyridyl, each of which is substituted with 2 or 3 $R_{12}$. In some embodiments, $R_1$ is phenyl substituted with 2 or 3 $R_{12}$. In some embodiments, $R_1$ is phenyl substituted with 2 $R_{12}$. In some embodiments, $R_1$ is phenyl substituted with 3 $R_{12}$. In some embodiments, $R_1$ is pyridyl substituted with 2 $R_{12}$.

In some embodiments of any one of Formulae II-XI, each $R_{12}$ is independently selected from the group consisting of halo, $C_{1-4}$alkyl, $C_{1-4}$alkoxy, $C_{1-4}$haloalkyl, and $OR_{14}$. In some embodiments, each $R_{12}$ is independently selected from the group consisting of halo, hydroxy, amino, methylamino, dimethylamino, cyano, $C_{1-4}$alkyl, $C_{1-4}$haloalkyl, and $C_{1-4}$alkoxy. In some embodiments, each $R_{12}$ is independently selected from the group consisting of halo, $C_{1-4}$alkyl, $C_{1-4}$alkoxy, and $C_{1-4}$haloalkyl. In some embodiments, each $R_{12}$ is independently selected from the group consisting of F, Cl, Br, $CH_3$, $OCH_3$, and $CF_3$.

In some embodiments of any one of Formulae II-XI, each $R_{12}$ is independently selected from the group consisting of F, Cl, Br, $CH_3$, $OCH_3$, $CF_3$,

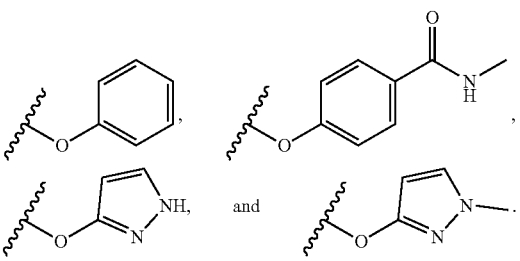

In some embodiments of any one of Formulae II-XI, $R_1$ is phenyl substituted with 2 $R_{12}$; and each $R_{12}$ is independently selected from the group consisting of F, Cl, Br, $CH_3$, $OCH_3$, and $CF_3$. In some embodiments, $R_1$ is phenyl substituted with 2 $R_{12}$; and each $R_{12}$ is Cl.

In some embodiments of any one of Formulae II-XI, $R_1$ is phenyl substituted with 3 $R_{12}$; and each $R_{12}$ is independently selected from the group consisting of F, Cl, Br, $CH_3$, $OCH_3$, $CF_3$,

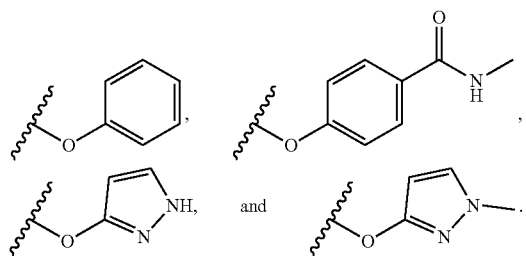

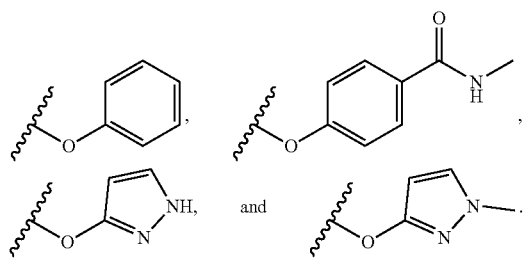

In some embodiments of any one of Formulae II-XI, $R_1$ is phenyl substituted with 3 $R_{12}$; the first and second $R_{12}$ are each Cl; and the third $R_{12}$ is Br. In some embodiments, $R_1$ is phenyl substituted with 3 $R_{12}$; the first and second $R_{12}$ are each Cl; and the third $R_{12}$ is selected from the group consisting of:

In some embodiments of any one of Formulae II-XI, In some embodiments, $R_{14}$ is phenyl, optionally substituted by one or two groups independently selected from the group consisting of $C_{1-4}$alkylamido, halo, hydroxy, cyano, and $C_{1-4}$alkyl. In some embodiments, $R_{14}$ is phenyl, substituted with $C_{1-4}$alkylamido. In some embodiments, $R_{14}$ is phenyl substituted with —C(O)NHMe. In some embodiments, $R_{14}$ is phenyl. In some embodiments, $R_{14}$ is pyrazolyl, optionally substituted by one or two groups independently selected from the group consisting of $C_{1-4}$alkylamido, halo, hydroxy, cyano, and $C_{1-4}$alkyl. In some embodiments, $R_{14}$ is pyrazolyl substituted with $C_{1-4}$alkyl. In some embodiments, $R_{14}$ is pyrazolyl substituted with methyl. In some embodiments, $R_{14}$ is N-methylpyrazolyl. In some embodiments, $R_{14}$ is pyrazolyl.

In some embodiments of Formula II or III, $R_6$ is amino or $C_{1-4}$aminoalkyl. In certain embodiments, $R_6$ is amino or aminomethyl. In certain embodiments, $R_6$ is amino. In certain embodiments, $R_6$ is aminomethyl.

In some embodiments of Formula II or III, $R_7$ is hydroxy, $C_{1-4}$alkyl, or $C_{1-4}$hydroxyalkyl. In certain embodiments, $R_7$ is $C_{1-4}$alkyl. In certain embodiments, $R_7$ is methyl. In certain embodiments, $R_7$ is ethyl.

In some embodiments of Formula II or III, $R_6$ is amino; and $R_7$ is $C_{1-4}$alkyl. In certain embodiments, $R_6$ is amino; and $R_7$ is methyl. In some embodiments, $R_6$ is amino; and $R_7$ is ethyl. In some embodiments, $R_6$ is aminomethyl; and $R_7$ is $C_{1-4}$alkyl. In certain embodiments, $R_6$ is aminomethyl; and $R_7$ is methyl.

In some embodiments of any one of Formulae IV-XI, each $R^a$ is independently selected from the group consisting of amino, halo, hydroxy, cyano, $C_{1-4}$alkyl, $C_{1-4}$alkoxy, and $C_{1-4}$haloalkyl. In some embodiments, each $R^a$ is independently amino or $C_{1-4}$alkyl. In some embodiments, each $R^a$ is independently amino or methyl.

In some embodiments, the compound is represented by the formula selected from the group consisting of:

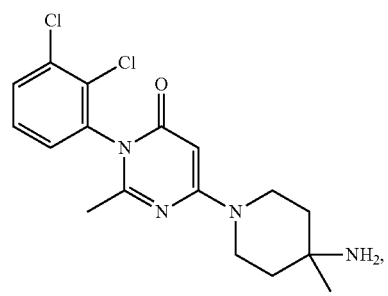

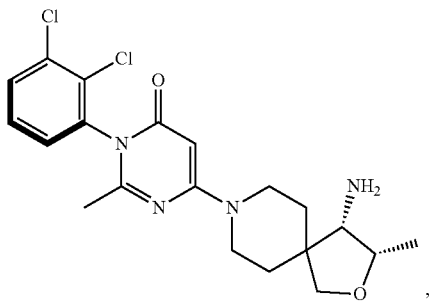

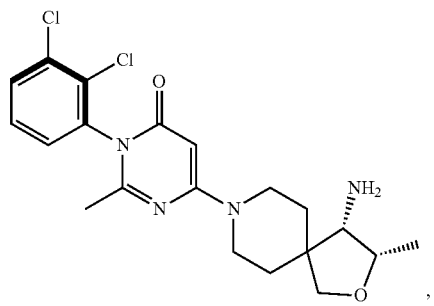

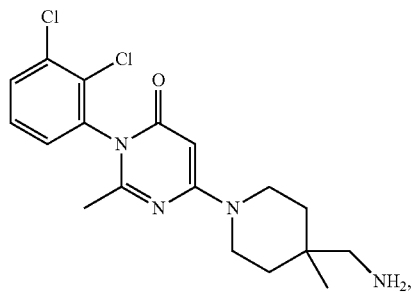

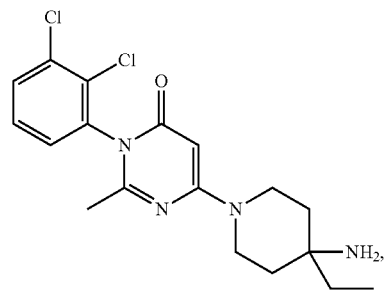

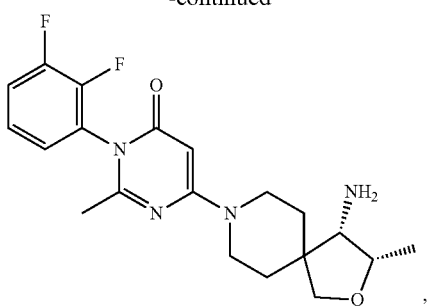
,
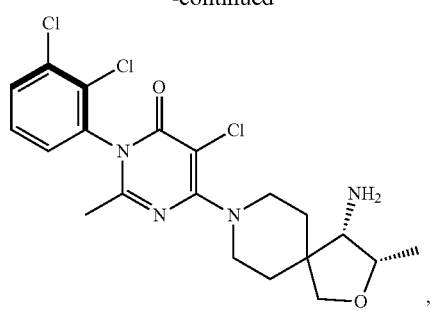
,
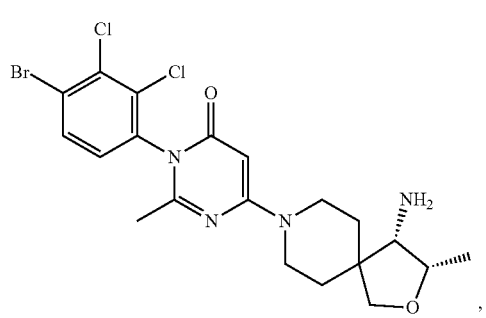
,
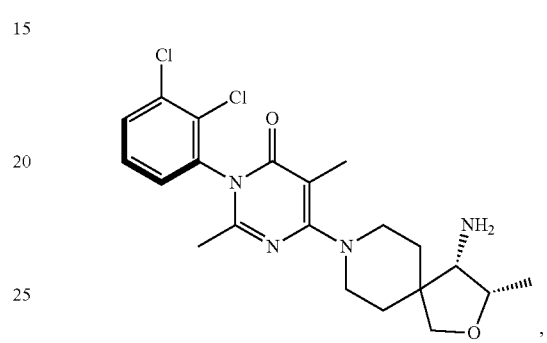
,
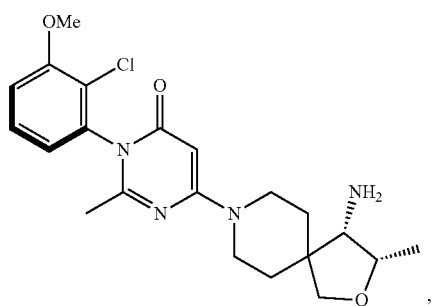
,
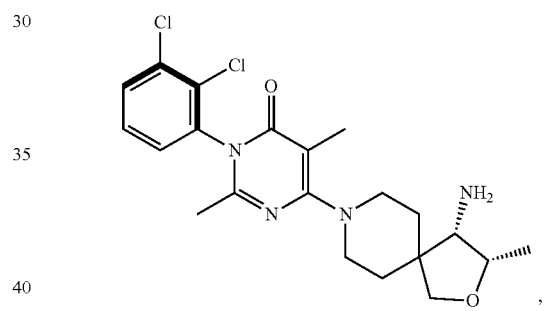
,
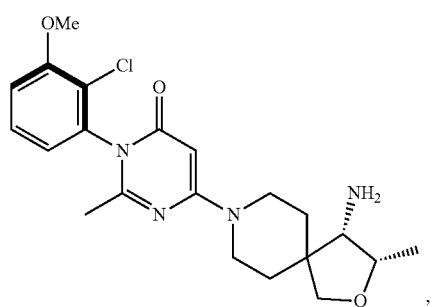
,
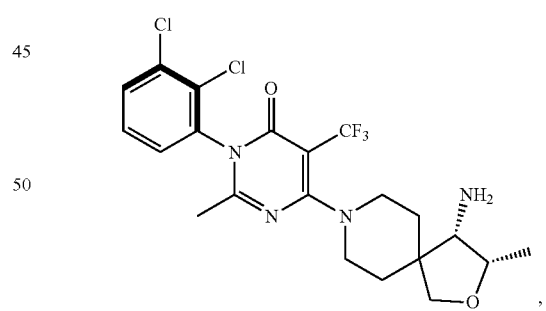
,
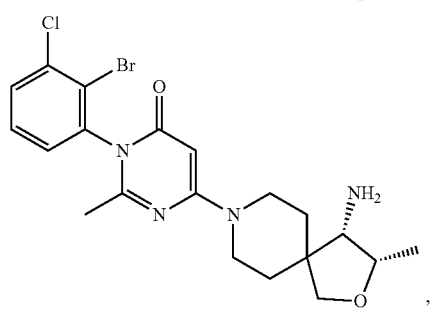
,
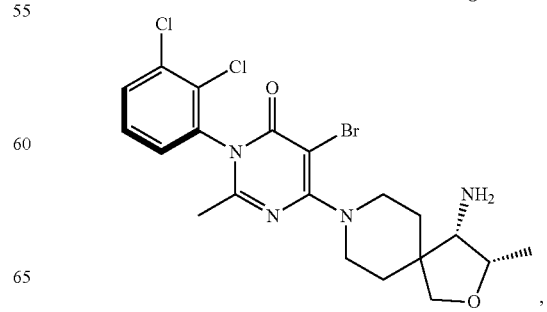
, 47
-continued
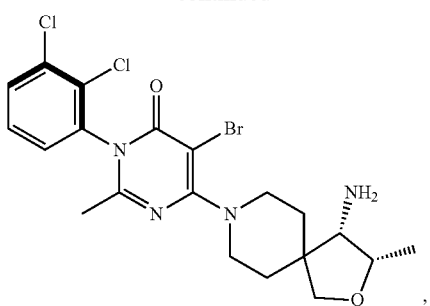
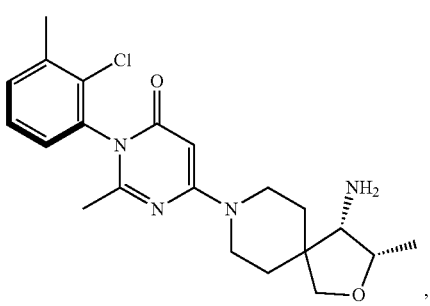
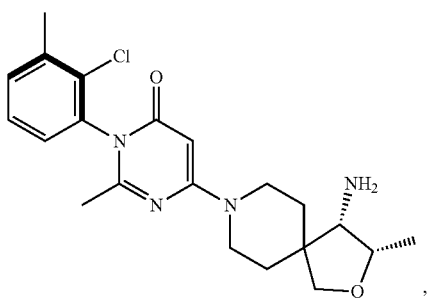
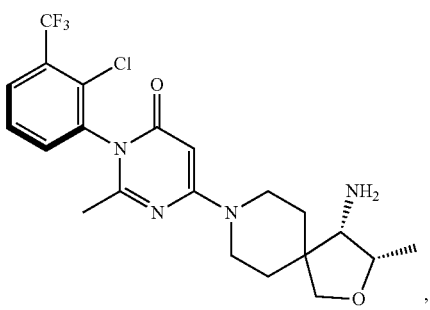
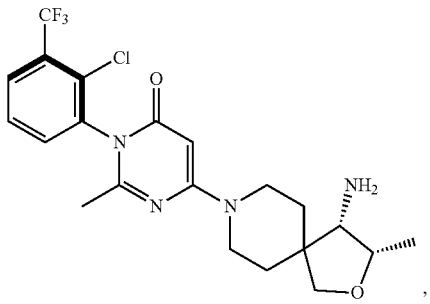
48
-continued
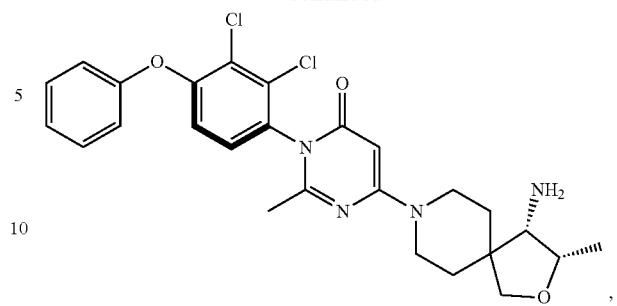
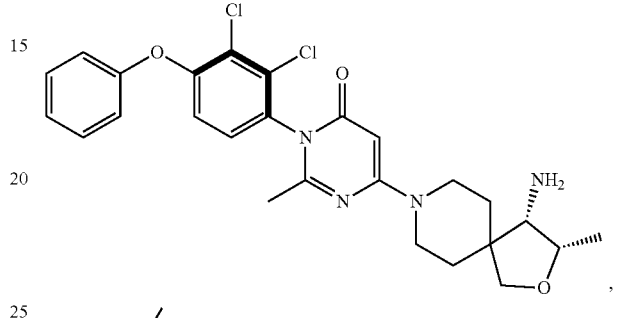
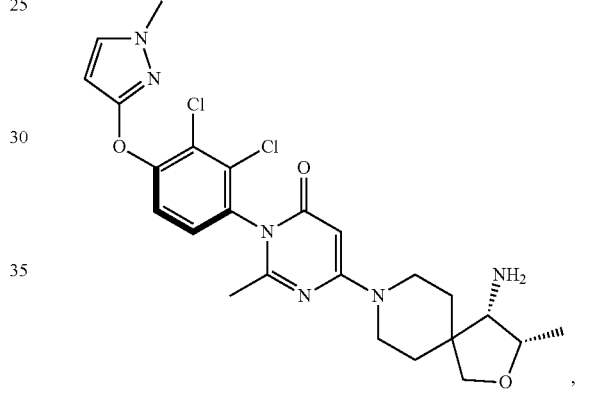
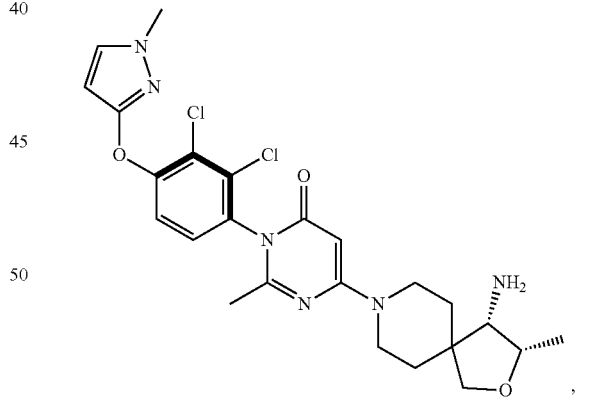
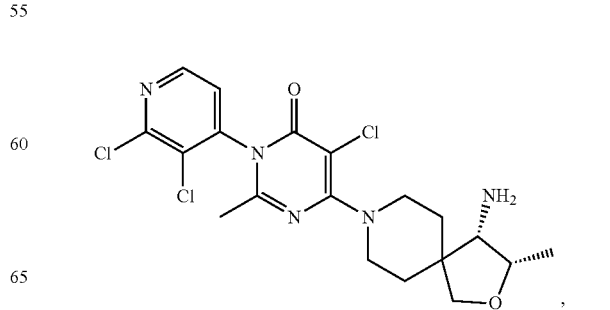

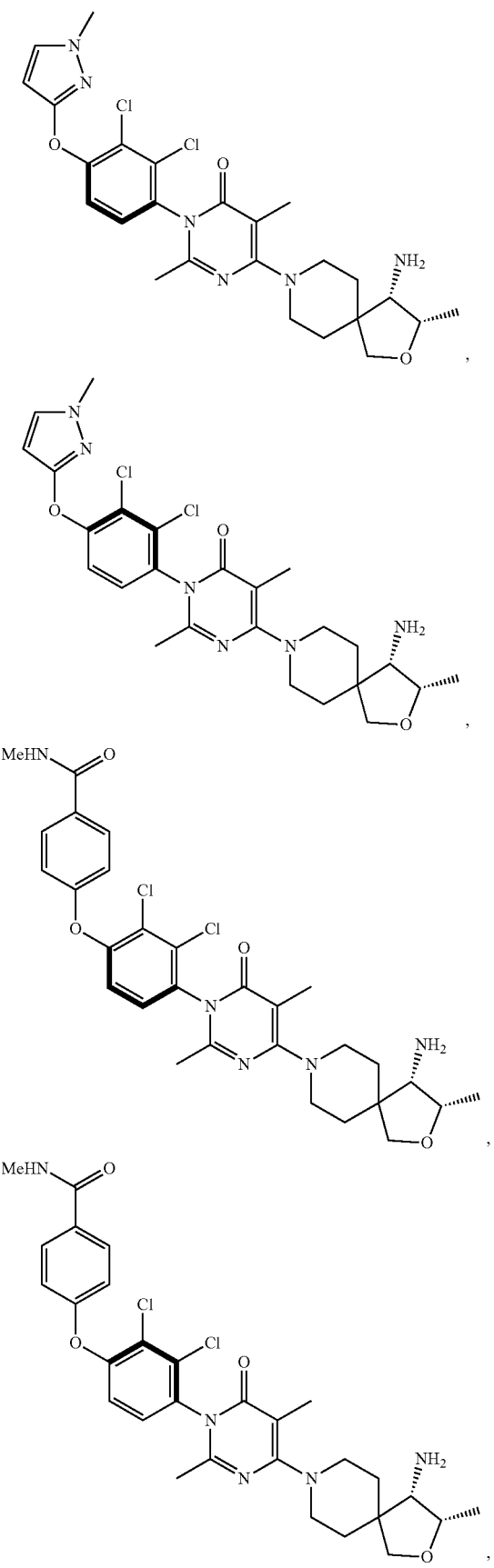

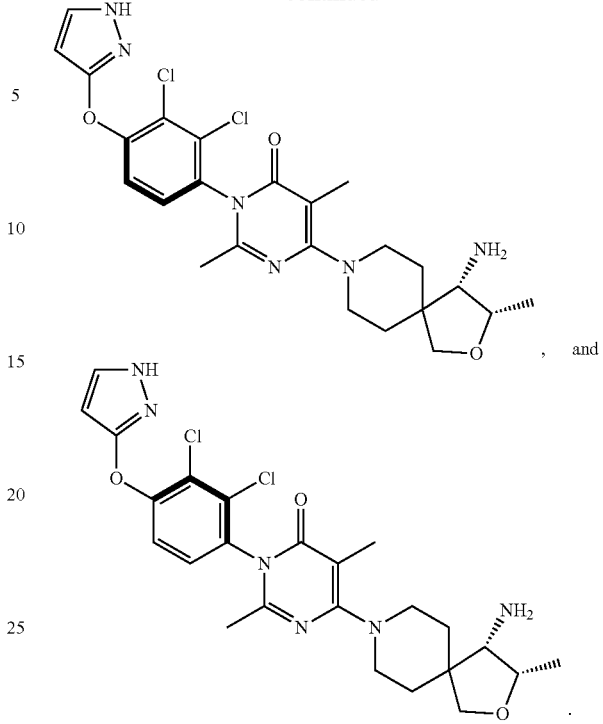

, and

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound selected from the Examples disclosed herein.

IV. Composition

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the pharmaceutical composition is formulated for intravenous administration.

In certain embodiments, the pharmaceutical composition is formulated for subcutaneous administration.

In certain embodiments, the oral pharmaceutical composition is selected from a tablet and a capsule.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration selected. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

V. Methods

The present invention also relates to a method of inhibiting at least one PTPN11 function comprising the step of contacting PTPN11 with a compound as described herein. The cell phenotype, cell proliferation, activity of PTPN11, change in biochemical output produced by active PTPN11, expression of PTPN11, or binding of PTPN11 with a natural binding partner may be monitored. Such methods may be modes of treatment of disease, biological assays, cellular assays, biochemical assays, or the like.

Also provided herein is a method of treatment of a PTPN11-mediated disease comprising the administration of a therapeutically effective amount of a compound as disclosed herein, or a salt or tautomer thereof, to a patient in need thereof.

In certain embodiments, the disease is cancer.
In certain embodiments, the cancer is selected from breast cancer, colon cancer, leukemia, or melanoma.

Also provided herein is a method of treatment of a PTP-mediated disease comprising the administration of a therapeutically effective amount of a compound as disclosed herein, or a salt or tautomer thereof, to a patient in need thereof.

In certain embodiments, the disease is selected from Noonan Syndrome and Leopard Syndrome.
In certain embodiments, the disease is cancer.
In certain embodiments, the cancer is selected from breast cancer, colon cancer, leukemia, or melanoma.

Also provided herein is a compound as disclosed herein for use as a medicament.

Also provided herein is a compound as disclosed herein for use as a medicament for the treatment of a PTPN11-mediated disease.

Also provided herein is a compound as disclosed herein for use as a medicament for the treatment of a PTP-mediated disease.

Also provided is the use of a compound as disclosed herein as a medicament.

Also provided is the use of a compound as disclosed herein as a medicament for the treatment of a PTPN11-mediated disease.

Also provided is a compound as disclosed herein for use in the manufacture of a medicament for the treatment of a PTPN11-mediated disease.

Also provided is the use of a compound as disclosed herein for the treatment of a PTPN11-mediated disease.

Also provided is the use of a compound as disclosed herein for the treatment of a PTP-mediated disease.

Also provided herein is a method of inhibition of PTPN11 comprising contacting PTPN11 with a compound as disclosed herein, or a salt or tautomer thereof.

Also provided herein is a method of inhibition of PTP comprising contacting PTP with a compound as disclosed herein, or a salt or tautomer thereof.

Also provided herein is a method for achieving an effect in a patient comprising the administration of a therapeutically effective amount of a compound as disclosed herein, or a salt or tautomer thereof, to a patient, wherein the effect is cognition enhancement.

In certain embodiments, the PTPN11-mediated disease is selected from Noonan Syndrome and Leopard Syndrome.
In certain embodiments, the PTPN11-mediated disease is cancer.
In certain embodiments, the PTPN11-mediated disease is selected from breast cancer, colon cancer, leukemia, or melanoma.

Also provided is a method of modulation of a PTPN11-mediated function in a subject comprising the administration of a therapeutically effective amount of a compound as disclosed herein.

Administration and Combination Therapy

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, tautomer, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a PTPN11 (SHP2) inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); vinca alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti-CTLA-4 antibody ipilimumab (YERVOY); and those that target LAG3 (lymphocyte activation gene 3 protein), KIR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);

(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;

(7) aromatase inhibitors, including but not limited to aminoglutethimide, anastrozole (ARIMIDEX), letrozole (FEMARA), vorozole (RIVIZOR), exemestane (AROMASIN);

(8) angiogenesis inhibitors, including but not limited to genistein, sunitinib (SUTENT) and bevacizumab (AVASTIN);

(9) anti-steroids and anti-androgens such as aminoglutethimide (CYTADREN), bicalutamide (CASODEX), cyproterone, flutamide (EULEXIN), nilutamide (NILANDRON);

(10) tyrosine kinase inhibitors, including but not limited to imatinib (GLEEVEC), erlotinib (TARCEVA), lapatininb (TYKERB), sorafenib (NEXAVAR), and axitinib (INLYTA);

(11) mTOR inhibitors such as everolimus, temsirolimus (TORISEL), and sirolimus;

(12) monoclonal antibodies such as trastuzumab (HERCEPTIN) and rituximab (RITUXAN);

(13) other agents, such as amsacrine; Bacillus Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PTPN11-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of PTPN11-mediated disorders.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

The compounds, compositions, and methods disclosed herein are useful for the treatment of disease. In certain embodiments, the disease is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL), Chronic Myelogenous Leukemia (CML), Acute Myelogenous Leukemia (AML)) and lymphomas including lymphocytic, granulocytic and monocytic. Additional types of cancers which may be treated using the compounds and methods of the invention include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

VI. Methods of Preparation

The chirality of the molecule is described by specifying its configuration using the Cahn-Ingold-Prelog convention, using the descriptors R and S for central chirality and $R_a$ and $S_a$ for axial chirality. PAC, 1996, 68, 2193, Basic terminology of stereochemistry (IUPAC Recommendations 1996), doi:10.1351/pac199668122193; Preferred IUPAC Names Chapter 9, September, 2004. Cahn, C. K. Ingold and V. Prelog, *Angew. Chem. Internal. Ed. Eng.* 5, 385-415, 511 (1966); V. Prelog and G. Helmchen, *Angew. Chem. Internal. Ed. Eng.* 21, 567-583 (1982).

Synthesis Schemes

The following schemes can be used to practice the present invention.

General Synthetic Methods for Preparing Compounds

The following scheme can be used as general guidance to prepare compounds of the present invention.

List of Abbreviations: $Pd_2dba_3$—Tris(dibenzylideneacetone)dipalladium; Xantphos—4,5-Bis(diphenylphosphino)-9,9-dimethylxanthene; HCl=hydrogen chloride; TFA=trifluoroacetic acid; $POCl_3$— Phosphorus (V) oxychloride; $Tf_2O$—Trifluoromethanesulfonic anhydride; DIEA—Diisopropyl ethylamine; DCM=dichloromethane; BOP—(benzotriazol-1-yloxytris(dimethylamino)phosphonium hexafluorophosphate); DBU—1,8-Diazabicyclo[5.4.0]undec-7-ene; NBS—N-Bromosuccinimide; and NCS—N-Chlorosuccinimide.

Scheme I

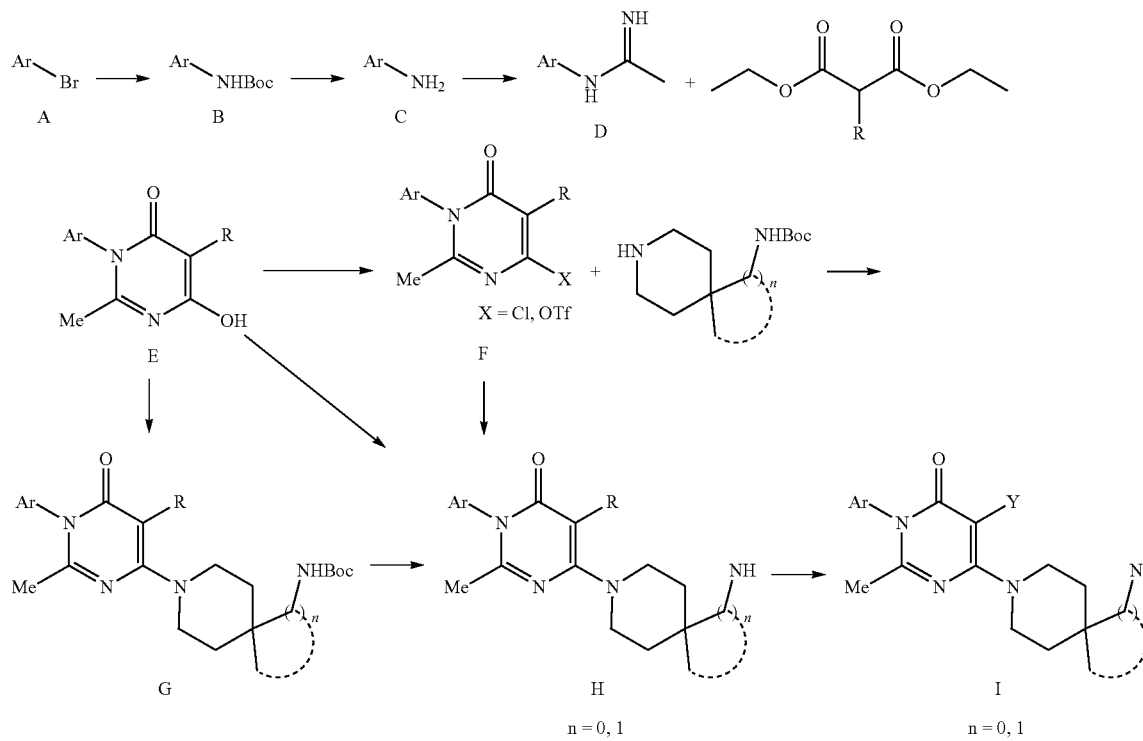

Aryl halide A can be transformed into the corresponding protected amine B using a "Pd" catalyst and ligand such as $Pd_2dba_3$ and Xantphos. Amine B can be deprotected to afford C and the corresponding acetimidamide D can be formed by treatment of amine C with acetonitrile and an acid such as HCl. Aryl substituted-6-hydroxy-2-methylpyrimidin-4(3H)-one E is formed by reacting D with the desired malonate to afford E. E can be transformed to the corresponding halide by treatment with reagent eg $POCl_3$ or triflate by $Tf_2O$ and DIEA in DCM. Subsequent SNAr reaction can provide protected amine G that can be transformed to the unprotected amine H. F can directly transformed to H in an SNAr reaction. Direct conversion of E to H can be performed by applying reagents such as BOP and DBU. H can be further functionalized to the corresponding bromide, chloride or $CF_3$ derivative (I) by applying reagent such as NBS, NCS or bis((((trifluoromethyl)sulfinyl)oxy) zinc in the presence of tert-butyl hydroperoxide.

Fluoronitrobenzene derivative J can be transferred to corresponding ether K using an alcohol or phenol and a base such as sodium hydride under SNAr reaction conditions. The nitro derivative can be reduced to the amine L using a reducing agent such as $SnCl_2.2H_2O$. Compound L subsequently can be transformed to the desired pyrimidinone derivative M as described in Scheme I.

It will be appreciated that other synthetic routes may be available for practice of the present invention.

The invention is further illustrated by the following examples, which may be synthesized and isolated as free bases or as salts, for example TFA or HCl salts.

VII. Examples

List of Abbreviations mg—milligram; mL—milliliter; ul=microliter; M=molar; mmol—millimol; h=hour; min.=minute; Rt—Room Temperature; $N_2$=nitrogen; HCl=hydrogen chloride;

H₂O=water; MS=mass spectrometry; ES+=electrospray positive ionization; $^1$H-NMR=proton nuclear magnetic resonance; MHz=megahertz; DMSO-$d_6$=dimethyl sulfoxide deuterated-6; H=hydrogen; rt=room temperature; °C.=degrees Celsius; $Br_2$=bromine; NaOH=sodium hydroxide; $NaHSO_3$=sodium bisulfite; $K_2CO_3$=potassium carbonate; NMP=N-Methyl-2-pyrrolidone: BOP—(benzotriazol-1-yloxytris(dimethylamino)phosphonium hexafluorophosphate); DBU—1,8-Diazabicyclo[5.4.0]undec-7-ene; DIEA—Diisopropyl ethylamine; MW=microwave; KF=potassium fluoride; $Pd(dppf)Cl_2$=[1,1'-bis(diphenylphosphino)ferrocene]palladium(II) dichloride; $Pd_2dba_3$—Tris(dibenzylideneacetone)dipalladium; $POCl_3$—Phosphorus (V) oxychloride; PE=petroleum ether; EA=ethyl acetate; $CDCl_3$=deuterated chloroform; MeOH=methanol; $D_2O$=deuterated water; HPLC=high pressure liquid chromatography; DMSO=dimethyl sulfoxide; MeCN (or ACN)=acetonitrile; NIS=N-iodosuccinimide; DMF=dimethylformamide; $K_3PO_4$=potassium phosphate, tribasic; $Et_2O$—Diethyl ether; EtOAc—Ethyl acetate; EtOH—Ethanol; NaOMe—Sodium methoxide; NaOEt—Sodium ethoxide; NCS—N-Chlorosuccinimide; TBDMS=TBS=tert-butyldimethylsilyl; TFA=trifluoroacetic acid; DCM=dichloromethane; Xantphos—4,5-Bis(diphenylphosphino)-9,9-dimethylxanthene.

Example 1

6-(4-Amino-4-methylpiperidin-1-yl)-3-(2,3-dichlorophenyl)-2-methylpyrimidin-4(3H)-one TFA Salt

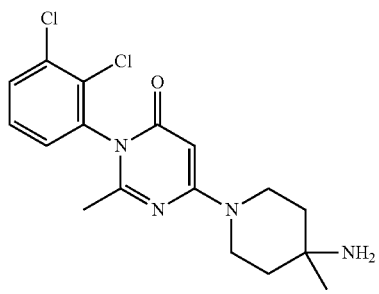 [SMILES: Cc1nc(N2CCC(C)(N)CC2)cc(=O)n1-c1cccc(Cl)c1Cl]

Step 1: N-(2,3-Dichlorophenyl)acetimidamide

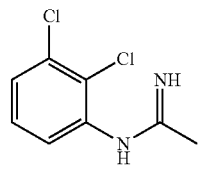

Method A

To a mixture of 2,3-dichloroaniline (1.6 g, 10 mmol) and MeCN (615 mg, 15.0 mmol) in 1,2-dichloroethane (10 mL) was added $AlCl_3$ (1.46 g, 1.10 mmol) at 0° C. The reaction mixture was stirred for 10 min then it was heated to 100° C. for 18 h in a sealed tube. The reaction was cooled to rt, ice-water (30 mL) was added, and the aqueous phase was extracted with DCM (50 mL×2). Subsequently, 2M NaOH was added to adjust the pH to 10 and the aqueous phase was extracted with DCM (50 mL×3). The combined organic layers were dried over $MgSO_4$ and concentrated under reduced pressure to afford the title compound as a beige oil (950 mg, 47%). MS (ES+) $C_8H_8Cl_2N_2$ requires: 202, found: 203[M+H]$^+$. The product was used in the next step without further purification.

Method B

In a high pressure reaction vessel MeCN (123 mL) was bubbled with HCl gas for 15 seconds at 0° C. to give a saturated solution. 2,3-Dichloroaniline (7.30 ml, 61.7 mmol) was added and a white solid precipitate formed. The vessel was sealed and the mixture was heated at 120° C. for 16 h. The reaction mixture was cooled to rt and the white precipitate was collected by vacuum filtration. The solid was rinsed with $Et_2O$ (20 mL×3) and dried under vacuum to afford the title compound (14.5 g, 98% yield) as a white solid. MS (ES$^+$) $C_8H_8Cl_2N_2$ requires: 202, found: 203 [M+H]$^+$.

Step 2: 3-(2,3-Dichlorophenyl)-6-hydroxy-2-methylpyrimidin-4(3H)-one

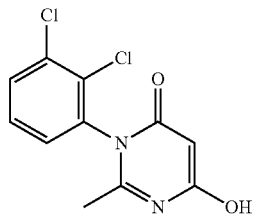 [SMILES: Cc1nc(O)cc(=O)n1-c1cccc(Cl)c1Cl]

Method A

To a solution of N-(2,3-dichlorophenyl)acetimidamide (950 mg, 4.68 mmol) in 2-methoxyethan-1-ol (10 mL) was added diethyl malonate (2.99 g, 18.7 mmol) and NaOMe in MeOH (4M, 4.7 mL, 18 mmol). The mixture was heated at 120° C. for 16 h. The reaction mixture was cooled to rt, it was poured onto water (50 mL) and it was extracted with $Et_2O$ (50 mL). The aqueous layer was acidified to pH~2 with HCl (6M, aq.) and the solid precipitate was collected by filtration to afford the title compound (1 g, 77%) as a white solid. MS (ES+) $C_{11}H_8Cl_2N_2O_2$ requires: 270, found: 271 [M+H]$^+$.

Method B

To a suspension of N-(2,3-dichlorophenyl)acetimidamide (30 g, 125 mmol) in EtOH (125 mL) were added diethyl malonate (38.2 mL, 250 mmol) and NaOEt (20% in EtOH) (140 mL, 376 mmol) and the resulting mixture was stirred in a sealed tube at 120° C. for 18 h. The reaction mixture was allowed to cool to room temperature and the volatiles were removed under reduced pressure. Water (30 mL) was added to the residue, the mixture was cooled to 0° C. and the mixture was acidified to pH~2 with HCl (6M, aq). The mixture was allowed to warm to rt and stirred for 1 h. The solid was collected by vacuum filtration, it was rinsed with $Et_2O$ (20 mL×2) and dried under reduced pressure to afford the title compound (26.3 g, 77%) as a tan solid (mixture of enantiomers). MS (ES$^+$) $C_{11}H_8Cl_2N_2O_2$ requires: 270, found: 271 [M+H]$^+$.

The compound of Step 2 can exist as a mixture of 3-($S_a$)-(2,3-Dichlorophenyl)-6-hydroxy-2-methylpyrimidin-4(3H)-one and 3-(R)-(2,3-dichlorophenyl)-6-hydroxy-2-methylpyrimidin-4(3H)-one Step 3: 6-Chloro-3-(2,3-dichlorophenyl)-2-methylpyrimidin-4(3H)-one

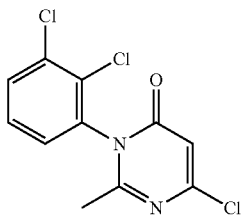 [SMILES: Cc1nc(Cl)cc(=O)n1-c1cccc(Cl)c1Cl]

A mixture of 1-(2,3-dichlorophenyl)-2-methylpyrimidine-4,6(1H,5H)-dione (250 mg, 0.92 mmol) in POCl$_3$ (5 mL) was heated at 100° C. for 4 hrs. The reaction mixture was cooled to rt, it was concentrated under reduced pressure and it was slowly added to ice-water. The mixture was extracted with EtOAc (15 mL×3). The organic layer was dried and concentrated under reduced pressure. The residue was purified by flash column chromatography (EtOAc in PE, 20 to 50%) to afford the title compound as a beige solid (100 mg, 37.5%) (mixture of enantiomers). MS (ES+) $C_{11}H_7Cl_3N_2O$ requires: 288, found: 289[M+H]$^+$.

The compound of Step 3 can exist as a mixture of 6-Chloro-3-($S_a$)-(2,3-dichlorophenyl)-2-methylpyrimidin-4(3H)-one and 6-chloro-3-(R)-(2,3-dichlorophenyl)-2-methylpyrimidin-4(3H)-one.

Step 4: Tert-butyl (1-(1-(2,3-dichlorophenyl)-2-methyl-6-oxo-1,6-dihydropyrimidin-4-yl)-4-methylpiperidin-4-yl)carbamate

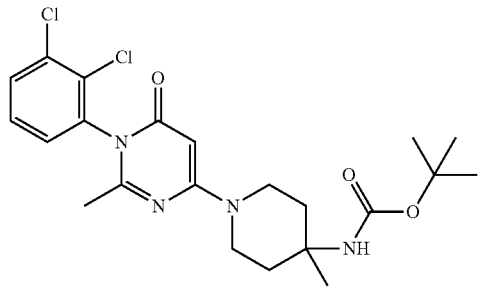 [SMILES: Cc1nc(N2CCC(C)(NC(=O)OC(C)(C)C)CC2)cc(=O)n1-c1cccc(Cl)c1Cl]

A mixture of 6-chloro-3-(2,3-dichlorophenyl)-2-methylpyrimidin-4(3H)-one (100 mg, 0.35 mmol), tert-butyl (4-methylpiperidin-4-yl)carbamate (89 mg, 0.42 mmol) and DIEA (134 mg, 1.04 mmol) in DMF (3 mL) was stirred at 100° C. for 3 h. The reaction mixture was diluted with water, it was extracted with EtOAc (15 mL×3). The organic layer was washed with brine, dried over MgSO$_4$ and concentrated under reduced pressure to afford the title compound. MS (ES+) $C_{22}H_{28}Cl_2N_4O_3$ requires: 466, found: 467[M+H]$^+$. The product was used in the next step without further purification.

The compound of Step 4 can exist as a mixture of Tert-butyl (1-(1-($S_a$)-(2,3-dichlorophenyl)-2-methyl-6-oxo-1,6-dihydropyrimidin-4-yl)-4-methylpiperidin-4-yl)carbamate and tert-butyl (1-(1-($R_a$)-(2,3-dichlorophenyl)-2-methyl-6-oxo-1,6-dihydropyrimidin-4-yl)-4-methylpiperidin-4-yl)carbamate.

Step 5: 6-(4-amino-4-methylpiperidin-1-yl)-3-(2,3-dichlorophenyl)-2-methylpyrimidin-4(3H)-one TFA salt To a solution of tert-butyl (1-(1-(2,3-dichlorophenyl)-2-methyl-6-oxo-1,6-dihydropyrimidin-4-yl)-4-methylpiperidin-4-yl)carbamate (0.35 mmol, crude) in DCM (3 mL) was added TFA (1 mL). The resulting solution was stirred at room temperature for 2 h and concentrated under reduced pressure. The residue was purified by prep-HPLC (Mobile phase: A=0.01% TFA/H2O, B=MeCN; Gradient: B=60%-95% in 18 min; Column: Venusil CBP C18 (L) C18, 10 um, 21.2 mm×250 mm, Cat. NO.: VX902520-L) to afford the title compound as a white solid (110 mg, 86%); MS (ES+) $C_{17}H_{20}Cl_2N_4O$ requires: 366, found: 367 [M+H]$^+$; 1H NMR (500 MHz, DMSO) δ 8.03 (s, 3H), 7.80 (dd, J=7.8, 1.7 Hz, 1H), 7.61-7.46 (m, 2H), 5.47 (s, 1H), 4.08-3.82 (m, 2H), 3.34-3.29 (m, 2H), 2.00 (s, 3H), 1.71 (t, J=5.5 Hz, 4H), 1.37 (s, 3H).

The compound of Example 1 can exist as a mixture of 6-(4-amino-4-methylpiperidin-1-yl)-3-($S_a$)-(2,3-dichlorophenyl)-2-methylpyrimidin-4(3H)-one TFA salt and 6-(4-amino-4-methylpiperidin-1-yl)-3-($R_a$)-(2,3-dichlorophenyl)-2-methylpyrimidin-4(3H)-one TFA salt.

Example 2a and 2b 6-((3S,4S)-4-Amino-3-methyl-2-oxa-8-azaspiro[4.5]decan-8-yl)-3-($S_a$)-(2,3-dichlorophenyl)-2-methylpyrimidin-4(3H)-one (Example 2a)

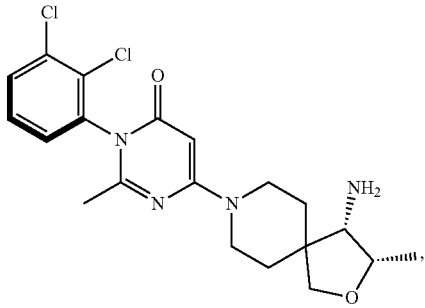

6-((3S,4S)-4-amino-3-methyl-2-oxa-8-azaspiro[4.5]decan-8-yl)-3-(R$_a$)-(2,3-dichlorophenyl)-2-methylpyrimidin-4(3H)-one (Example 2b)

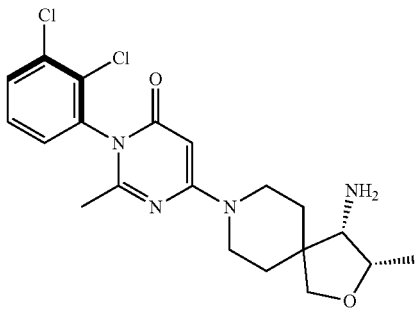

To a suspension of 3-(2,3-dichlorophenyl)-6-hydroxy-2-methylpyrimidin-4(3H)-one (Example 1, Step 2, 3.50 g, 12.9 mmol) and (3S,4S)-3-methyl-2-oxa-8-azaspiro[4.5]decan-4-amine dihydrochloride (3.45 g, 14.2 mmol) in MeCN (43 ml) were added DBU (6.23 mL, 41.3 mmol) and BOP (6.85 g, 15.5 mmol) and the resulting mixture was stirred at rt for 24 h. The mixture was concentrated under reduced pressure. The residue was purified via silica gel chromatography (2-15% MeOH with 2% NH$_4$OH in DCM) to afford the title compounds as a mixture of diastereomers (4.2 g, 77% yield) as an off-white solid. The mixture of diastereomers were separated by Chiral SFC (Mobile phase: CO$_2$/methanol (0.25% isopropylamine)=60/40; Flow rate: 80 g/min; 5 min; Column temperature: 25° C.; Back pressure: 100 bar; Column: ES Industries ChromegaChiral CCS, 2.0×25.0 cm) to afford the title compounds, Example 2a (19.7 g, 48%) as a white solid and Example 2b (11.6 g, 28%) as a white solid.

Example 2a 6-((3S,4S)-4-Amino-3-methyl-2-oxa-8-azaspiro[4.5]decan-8-yl)-3-(S$_a$)-(2,3-dichlorophenyl)-2-methylpyrimidin-4(3H)-one: MS (ES$^+$) C$_{20}$NH$_{24}$Cl$_2$N$_4$O$_2$ requires: 422, found: 423 [M+H]$^+$; $^1$H NMR (600 MHz, CDCl$_3$) δ 7.57 (dd, J=8.1, 1.5 Hz, 1H), 7.35 (t, J=8.0 Hz, 1H), 7.21 (dd, J=7.9, 1.5 Hz, 1H), 5.45 (s, 1H), 4.21-4.16 (m, 1H), 3.86 (br s, 2H), 3.79 (d, J=8.7 Hz, 1H), 3.68 (d, J=8.7 Hz, 1H), 3.40 (ddd, J=13.1, 9.1, 3.8 Hz, 1H), 3.31 (ddd, J=13.3, 9.4, 3.2 Hz, 1H), 2.98 (d, J=4.5 Hz, 1H), 2.06 (s, 3H), 1.84 (ddd, J=13.4, 9.4, 3.9 Hz, 1H), 1.75-1.60 (m, 3H), 1.23 (d, J=6.4 Hz, 3H).

Example 2b 6-((3S,4S)-4-Amino-3-methyl-2-oxa-8-azaspiro[4.5]decan-8-yl)-3-(R$_a$)-(2,3-dichlorophenyl)-2-methylpyrimidin-4(3H)-one: MS (ES$^+$) C$_2$NH$_{24}$Cl$_2$N$_4$O$_2$ requires: 422, found: 423 [M+H]$^+$; $^1$H NMR (600 MHz, CDCl$_3$) δ 7.57 (dd, J=8.2, 1.5 Hz, 1H), 7.36 (t, J=8.0 Hz, 1H), 7.21 (dd, J=7.9, 1.5 Hz, 1H), 5.46 (s, 1H), 4.22-4.14 (m, 1H), 3.95-3.82 (m, 2H), 3.80 (d, J=8.7 Hz, 1H), 3.68 (d, J=8.7 Hz, 1H), 3.45-3.36 (m, 1H), 3.29 (ddd, J=13.3, 9.5, 3.3 Hz, 1H), 2.99 (d, J=4.6 Hz, 1H), 2.07 (s, 3H), 1.84 (ddd, J=13.4, 9.4, 3.9 Hz, 1H), 1.77-1.70 (m, 1H), 1.70-1.61 (m, 2H), 1.24 (d, J=6.4 Hz, 3H).

The following Examples were synthesized with synthetic methods that were similar to that used for Example 1 and 2, and can generally be made by methods disclosed herein. The Examples may be made as free bases or as TFA salts.

TABLE 1

Examples 3-8

| Ex # | Structure and IUPAC Name | Calc. Mass | Mass [M + H]$^+$ |
|---|---|---|---|
| 3 | 6-[4-(aminomethyl)-4-methylpiperidin-1-yl]-3-(2,3-dichlorophenyl)-2-methyl-3,4-dihydropyrimidin-4-one | 380 | 381 |

TABLE 1-continued
Examples 3-8
| Ex # | Structure and IUPAC Name | Calc. Mass | Mass [M + H]+ |
|---|---|---|---|
| 4 | 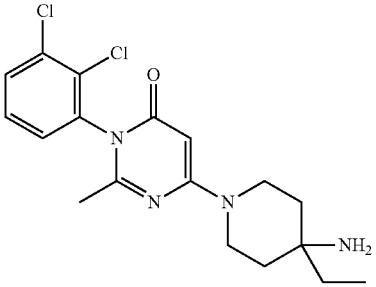 [SMILES: CCC1(N)CCN(c2cc(=O)n(-c3cccc(Cl)c3Cl)c(C)n2)CC1]<br>6-(4-amino-4-ethylpiperidin-1-yl)-3-(2,3-dichlorophenyl)-2-methyl-3,4-dihydropyrimidin-4-one | 380 | 381 |
| 5 | 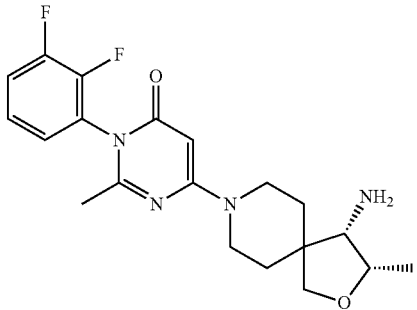 [SMILES: Cc1nc(N2CCC3(CC2)CO[C@@H](C)[C@H]3N)cc(=O)n1-c1cccc(F)c1F]<br>6-[(3S,4S)-4-amino-3-methyl-2-oxa-8-azaspiro[4.5]decan-8-yl]-3-(2,3-difluorophenyl)-2-methyl-3,4-dihydropyrimidin-4-one | 390 | 391 |
| 6 | 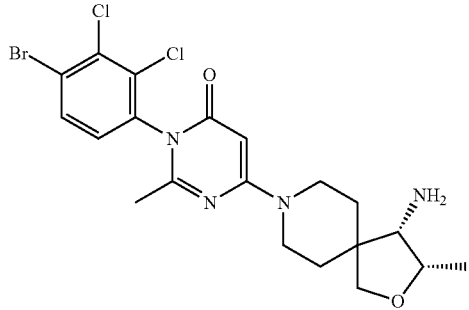 [SMILES: Cc1nc(N2CCC3(CC2)CO[C@@H](C)[C@H]3N)cc(=O)n1-c1ccc(Br)c(Cl)c1Cl]<br>6-((3S,4S)-4-amino-3-methyl-2-oxa-8-azaspiro[4.5]decan-8-yl)-3-(4-bromo-2,3-dichlorophenyl)-2-methylpyrimidin-4(3H)-one | 500/502 | 501/503 |

TABLE 1-continued

Examples 3-8

| Ex # | Structure and IUPAC Name | Calc. Mass | Mass [M + H]+ |
|---|---|---|---|
| 7a | 6-((3S,4S)-4-amino-3-methyl-2-oxa-8-azaspiro[4.5]decan-8-yl)-3-(S_a)-(2-chloro-3-methoxyphenyl)-2-methylpyrimidin-4(3H)-one | 418 | 419 |
| 7b | 6-((3S,4S)-4-amino-3-methyl-2-oxa-8-azaspiro[4.5]decan-8-yl)-3-(R_a)-(2-chloro-3-methoxyphenyl)-2-methylpyrimidin-4(3H)-one | 418 | 419 |
| 8 | 6-((3S,4S)-4-amino-3-methyl-2-oxa-8-azaspiro[4.5]decan-8-yl]-3-(2-bromo-3-chlorophenyl)-2-methylpyrimidin-4(3H)-one | 466 | 467 |

The compound of Example 3 can exist as a mixture of 6-[4-(aminomethyl)-4-methylpiperidin-1-yl]-3-($S_a$)-(2,3-dichlorophenyl)-2-methyl-3,4-dihydropyrimidin-4-one and 6-[4-(aminomethyl)-4-methylpiperidin-1-yl]-3-($R_a$)-(2,3-dichlorophenyl)-2-methyl-3,4-dihydropyrimidin-4-one.

The compound of Example 4 can exist as a mixture of 6-(4-amino-4-ethylpiperidin-1-yl)$_3$-(S)-(2,3-dichlorophenyl)-2-methyl-3,4-dihydropyrimidin-4-one and 6-(4-amino-4-ethylpiperidin-1-yl)-3-($R_a$)-(2,3-dichlorophenyl)-2-methyl-3,4-dihydropyrimidin-4-one.

The compound of Example 5 can exist as a mixture of 6-[(3S,4S)-4-amino-3-methyl-2-oxa-8-azaspiro[4.5]decan-8-yl]-3-($S_a$)-(2,3-difluorophenyl)-2-methyl-3,4-dihydropyrimidin-4-one and 6-[(3S,4S)-4-amino-3-methyl-2-oxa-8-azaspiro[4.5]decan-8-yl]-3-($R_a$)-(2,3-difluorophenyl)-2-methyl-3,4-dihydropyrimidin-4-one.

The compound of Example 6 can exist as a mixture of 6-((3S,4S)-4-amino-3-methyl-2-oxa-8-azaspiro[4.5]decan-8-yl)-3-($S_a$)-(4-bromo-2,3-dichlorophenyl)-2-methylpyrimidin-4(3H)-one and 6-((3S,4S)-4-amino-3-methyl-2-oxa-8-azaspiro[4.5]decan-8-yl)-3-($R_a$)-(4-bromo-2,3-dichlorophenyl)-2-methylpyrimidin-4(3H)-one.

The compound of Example 8 can exist as a mixture of 6-((3S,4S)-4-amino-3-methyl-2-oxa-8-azaspiro[4.5]decan-8-yl)-3-($S_a$)-(2-bromo-3-chlorophenyl)-2-methylpyrimidin-4(3H)-one and 6-((3S,4S)-4-amino-3-methyl-2-oxa-8- azaspiro[4.5]decan-8-yl)-3-($R_a$)-(2-bromo-3-chlorophenyl)-2-methylpyrimidin-4(3H)-one.

Example 9

6-((3S,4S)-4-Amino-3-methyl-2-oxa-8-azaspiro[4.5]decan-8-yl)-5-chloro-3-($R_a$)-(2,3-dichlorophenyl)-2-methylpyrimidin-4(3H)-one

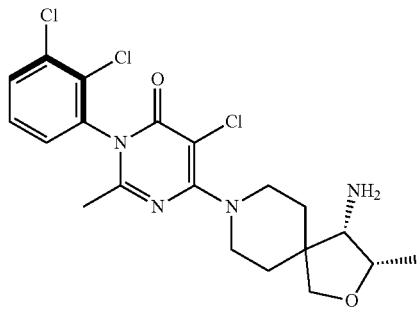

To a solution of 6-((3S,4S)-4-amino-3-methyl-2-oxa-8-azaspiro[4.5]decan-8-yl)-3-($R_a$)-(2,3-dichlorophenyl)-2-methylpyrimidin-4(3H)-one (Example 2b; 2.5 g, 5.9 mmol) in DCM (30 mL) was added NCS (946 mg, 7.09 mmol) and the resulting mixture was stirred at rt for 10 min. The mixture was concentrated under reduced pressure. The residue was purified via silica gel chromatography (2-15% MeOH with 2% NH$_4$OH in DCM) to afford the title compound (2.1 g, 78% yield) as a white solid. MS (ES$^+$) $C_{20}H_{23}Cl_3N_4O_2$ requires: 456, found: 457 [M+H]$^+$; $^1$H NMR (600 MHz, DMSO-d$_6$) δ 7.83 (dd, J=8.1, 1.6 Hz, 1H), 7.62 (dd, J=8.0, 1.6 Hz, 1H), 7.57 (t, J=8.0 Hz, 1H), 4.09-4.01 (m, 1H), 3.96-3.87 (m, 2H), 3.67 (d, J=8.4 Hz, 1H), 3.53-3.46 (m, 2H), 3.40 (ddd, J=12.9, 9.3, 3.1 Hz, 1H), 2.91 (d, J=5.1 Hz, 1H), 2.00 (s, 3H), 1.81 (ddd, J=13.2, 9.3, 3.6 Hz, 1H), 1.71-1.65 (m, 1H), 1.59-1.54 (m, 1H), 1.54-1.48 (m, 1H), 1.08 (d, J=6.4 Hz, 3H).

Example 10a and 10b 6-((3S,4S)-4-Amino-3-methyl-2-oxa-8-azaspiro[4.5]decan-8-yl)-3-($S_a$)-(2,3-dichlorophenyl)-2,5-dimethylpyrimidin-4(3H)-one (Example 10a)

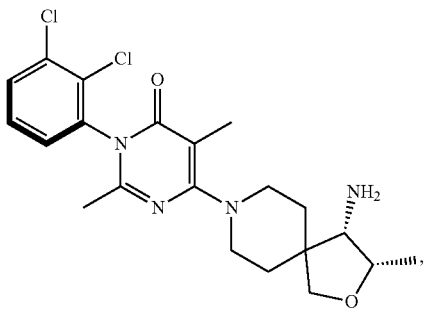

6-((3S,4S)-4-amino-3-methyl-2-oxa-8-azaspiro[4.5]decan-8-yl)-3-($R_a$)-(2,3-dichlorophenyl)-2,5-dimethylpyrimidin-4(3H)-one (Example 10b)

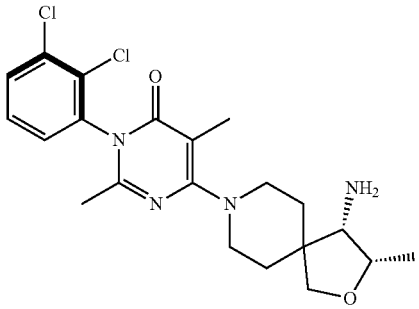

Method A

Step 1: 3-(2,3-Dichlorophenyl)-6-hydroxy-2,5-dimethylpyrimidin-4(3H)-one

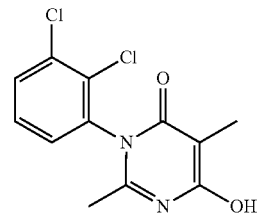 [SMILES: Cc1c(O)nc(C)n(-c2cccc(Cl)c2Cl)c1=O]

To a suspension of N-(2,3-dichlorophenyl)acetimidamide hydrochloride (Example 1, step 1) (44 g, 184 mmol) in EtOH (184 mL) were added diethyl 2-methylmalonate (62.6 ml, 367 mmol) and EtONa (206 ml, 551 mmol) and the resulting mixture was stirred in a sealed tube at 120° C. for 18 h. The reaction mixture was allowed to cool to room temperature and the volatiles were removed under reduced pressure. Water (200 mL) was added, the mixture was cooled to 0° C., and HCl (6 M) was added to adjust the pH to 2. The reaction was allowed to warm to rt and was stirred for 1 h. The reaction mixture was filtered through glass fiber paper, the solid was rinsed with Et$_2$O, collected, and dried under reduced pressure to afford the title compound (44.6 g, 156 mmol, 85% yield) as a pale yellow solid. MS (ES$^+$) $C_{12}H_{10}Cl_2N_2O_2$ requires: 284, found: 285 [M+H]$^+$.

The compound of Step 1 can exist as a mixture of 3-($S_a$)-(2,3-dichlorophenyl)-6-hydroxy-2,5-dimethylpyrimidin-4(3H)-one and 3-(R)-(2,3-dichlorophenyl)-6-hydroxy-2,5-dimethylpyrimidin-4(3H)-one.

Step 2: 6-((3S,4S)-4-Amino-3-methyl-2-oxa-8-azaspiro[4.5]decan-8-yl)-3-($S_a$)-(2,3-dichlorophenyl)-2,5-dimethylpyrimidin-4(3H)-one (Example 10a) and 6-((3S,4S)-4-amino-3-methyl-2-oxa-8-azaspiro[4.5]decan-8-yl)-3-($R_a$)-(2,3-dichlorophenyl)-2,5-dimethylpyrimidin-4(3H)-one (Example 10b)

To a suspension of 3-(2,3-dichlorophenyl)-6-hydroxy-2,5-dimethylpyrimidin-4(3H)-one (30 g, 105 mmol) and (3S,4S)-3-methyl-2-oxa-8-azaspiro[4.5]decan-4-amine dihydrochloride (28.1 g, 116 mmol) in acetonitrile (351 mL) were added DBU (50.8 mL, 337 mmol) and BOP (51.2 g, 116 mmol) and the resulting mixture was stirred at rt for 24 h. (3S,4S)-3-Methyl-2-oxa-8-azaspiro[4.5]decan-4-amine dihydrochloride (12.8 g, 52.5 mmol) and DBU (15.8 mL, 105 mmol) were added and the mixture was stirred at rt for an additional 24 h. The reaction mixture was concentrated under reduced pressure. The residue was partitioned between DCM (200 mL) and water (200 mL), the layers were separated and the aqueous layer was extracted with DCM (200 mL×3). The combined organic layers were dried over $Na_2SO_4$, filtered and concentrated under reduced pressure. The residue was purified via silica gel chromatography (2-15% MeOH with 2% $NH_4OH$ in DCM) to afford the title compounds as a mixture of diastereomers as an off-white solid. The mixture of diastereomers were separated by Chiral SFC (Mobile phase: $CO_2$/methanol (0.25% isopropylamine)=60/40; Flow rate: 80 g/min; 5 min; Column temperature: 25° C.; Back pressure: 100 bar; Column: Chiral Technologies Chiralpak AD-H, 2.1×25.0 cm) to afford the title compounds Example 10a (19.51 g, 42%, 98% ee) as a white solid (a single diastereomer) and Example 10b (19.25 g, 42%, >99% ee) as a white solid (a single diastereomer).

Example 10a 6-((3S,4S)-4-Amino-3-methyl-2-oxa-8-azaspiro[4.5]decan-8-yl)-3-($S_a$)-(2,3-dichlorophenyl)-2,5-dimethylpyrimidin-4(3H)-one: MS ($ES^+$) $C_{21}H_{26}Cl_2N_4O_2$ requires: 436, found: 437 $[M+H]^+$; $^1H$ NMR (600 MHz, DMSO-$d_6$) δ 7.83-7.77 (m, 1H), 7.57-7.50 (m, 2H), 4.09-4.02 (m, 1H), 3.66 (d, J=8.4 Hz, 1H), 3.58-3.51 (m, 2H), 3.49 (d, J=8.4 Hz, 1H), 3.21 (ddd, J=12.9, 9.3, 3.2 Hz, 1H), 3.13 (ddd, J=12.9, 9.4, 3.0 Hz, 1H), 2.89 (d, J=5.1 Hz, 1H), 1.97 (s, 3H), 1.89 (s, 3H), 1.78 (ddd, J=13.3, 9.5, 3.6 Hz, 1H), 1.66 (ddd, J=13.1, 9.1, 3.7 Hz, 1H), 1.57-1.52 (m, 1H), 1.52-1.47 (m, 1H), 1.08 (d, J=6.4 Hz, 3H).

Example 10b 6-((3S,4S)-4-Amino-3-methyl-2-oxa-8-azaspiro[4.5]decan-8-yl)-3-($R_a$)-(2,3-dichlorophenyl)-2,5-dimethylpyrimidin-4(3H)-one: MS ($ES^+$) $C_{21}H_{26}Cl_2N_4O_2$ requires: 436, found: 437 $[M+H]^+$; $^1H$ NMR (600 MHz, DMSO-$d_6$) δ 7.83-7.77 (t, J=4.8 Hz, 1H), 7.57-7.50 (d, J=4.8 Hz, 2H), 4.09-4.02 (m, 1H), 3.65 (d, J=8.4 Hz, 1H), 3.58-3.51 (m, 2H), 3.49 (d, J=8.4 Hz, 1H), 3.22 (ddd, J=13, 9.5, 2.5 Hz, 1H), 3.12 (ddd, J=13.0, 9.5, 2.5 Hz, 1H), 2.89 (d, J=5.1 Hz, 1H), 1.97 (s, 3H), 1.89 (s, 3H), 1.78 (ddd, J=13.2, 9.5, 3.7 Hz, 1H), 1.66 (ddd, J=13.2, 9.5, 3.7 Hz, 1H), 1.58-1.46 (m, 2H), 1.28 (bs, 2H), 1.08 (d, J=6.4 Hz, 3H).
Method B Step 1: 1-($R_a$)-(2,3-Dichlorophenyl)-2,5-dimethyl-6-oxo-1,6-dihydropyrimidin-4-yl trifluoromethanesulfonate

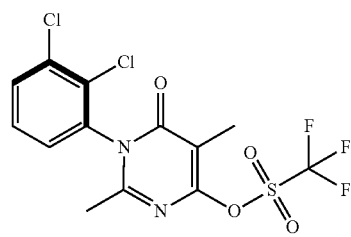

To a mixture of 3-($S_a$)-(2,3-dichlorophenyl)-6-hydroxy-2,5-dimethylpyrimidin-4(3H)-one and 3-($R_a$)-(2,3-dichlorophenyl)-6-hydroxy-2,5-dimethylpyrimidin-4(3H)-one (Example 10, Method A, Step 1) (100 g, 351 mmol) and DIPEA (183 mL, 1.05 mol) in DCM (1.00 L) was added $Tf_2O$ (116 mL g, 701 mmol, 116 mL) drop-wise at −25° C. The resulting mixture was stirred at −25° C.~−20° C. for 1 h and at 20° C. for 18 h. Two batches of the reaction mixture were combined. To the reaction mixture was added water (1 L), the resulting mixture was extracted with $CH_2Cl_2$ (1 L×2). The combined organic layers were washed with 1M HCl (1 L, aq), dried over $Na_2SO_4$, filtered and concentrated under reduced pressure. The residue was purified by column chromatography (EtOAc in PE, 20%) to afford a mixture of diastereomers (144 g, 336 mmol, 47.8% yield) as a brown solid. The mixture of diastereomers was separated by SFC (column: DAICEL CHIRALPAK AD (250 mm*50 mm, 10 um); mobile phase: [Neu-IPA]; B %: 15%-15%, 2.9 min, 1100 min) to afford the title compound (56.4 g, 18%, ee=99.5%) as a brown solid. MS ($ES^+$) $C_{13}H_9Cl_2F_3N_2O_4S$ requires: 416, found: 417 $[M+H]^+$.

Step 2: 6-((3S,4S)-4-Amino-3-methyl-2-oxa-8-azaspiro[4.5]decan-8-yl)-3-($R_a$)-(2,3-dichlorophenyl)-2,5-dimethylpyrimidin-4(3H)-one (Example 10b)

To a solution of (3S,4S)-3-methyl-2-oxa-8-azaspiro[4.5]decan-4-amine (23.3 g, 95.6 mmol, 1.05 eq, 2HCl) in DMF (50.0 mL) was added DIPEA (47.1 g, 364 mmol, 63.5 mL) and a solution of 1-($R_a$)-(2,3-dichlorophenyl)-2,5-dimethyl-6-oxo-1,6-dihydropyrimidin-4-yl trifluoromethanesulfonate (38.0 g 91.1 mmol, 1.00 eq) in DMF (200 mL) at 0° C. The resulting mixture was stirred at 15° C. for 18 h and (3S,4S)-3-methyl-2-oxa-8-azaspiro[4.5]decan-4-amine (1.11 g, 4.55 mmol, 2HCl) was added. The resulting mixture was stirred at 25° C. for 15 h. The reaction mixture was concentrated under reduced pressure. $K_2CO_3$ (15%, 500 mL, aq.) was added and the aqueous phase was extracted with DCM (200 mL×3). The combined organic layers were washed with brine (400 mL), dried over $Na_2SO_4$, filtered and concentrated under reduced pressure. The residue was purified by column chromatography (SiO2, MeOH in DCM, 5 to 20%) followed by reversed-phase column chromatography (0.1% $NH_3·H_2O$, MeCN:H2O (65:35). The residue was dissolved in hot MeOH (250 mL), to the resulting solution was added activated carbon (2.70 g) and the mixture was stirred at 60° C. for 15 min. The mixture was filtered and concentrated under reduced pressure to afford the title compound Example 10b (26.5 g, 66.5%) as off-white solid.

Example 11

6-((3S,4S)-4-Amino-3-methyl-2-oxa-8-azaspiro[4.5]decan-8-yl)-3-($R_a$)-(2,3-dichlorophenyl)-2-methyl-5-(trifluoromethyl)pyrimidin-4(3H)-one TFA salt

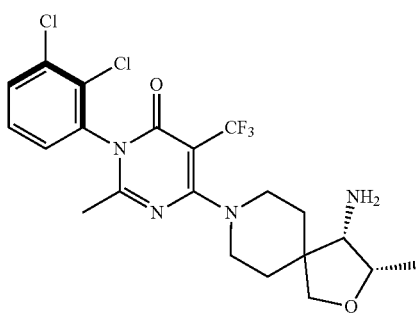

A suspension of 6-((3S,4S)-4-amino-3-methyl-2-oxa-8-azaspiro[4.5]decan-8-yl)-5-chloro-3-(R)-(2,3-dichlorophenyl)-2-methylpyrimidin-4(3H)-one (Example 9) (35 mg, 0.083 mmol), TFA (9.6 μL, 0.12 mmol) and bis(((trifluoromethyl)sulfinyl)oxy)zinc (55 mg, 0.16 mmol) in DCE (591 μL) was sonicated to give a uniform suspension then cooled to ° C. and tert-butyl hydroperoxide (34 μL, 0.25 mmol) was added dropwise. The resulting mixture was warmed to rt and stirred for 2 h. Water (1 mL) was added, the layers were separated and the aqueous layer was extracted with DCM (1 mL×3). The combined organic layers were dried over Na$_2$SO$_4$, filtered and concentrated under reduced pressure. The residue was purified by mass-triggered preparative HPLC (Mobile phase: A=0.1% TFA/H$_2$O, B=0.1% TFA/MeCN; Gradient: B=20-50%; 20 min; Column: XBridge C18, 5 μm, 19 mm×150 mm) to afford the title compound (15 mg, 30% yield) as a white solid (single diastereomer): MS (ES+) C$_{21}$H$_{23}$Cl$_2$F$_3$N$_4$O$_2$ requires: 490, found: 491 [M+H]+; $^1$H NMR (600 MHz, DMSO-d$_6$) δ 7.90 (s, 3H), 7.84 (dd, J=7.9, 1.8 Hz, 1H), 7.63-7.56 (m, 2H), 4.24-4.17 (m, 1H), 3.96 (d, J=14.0 Hz, 1H), 3.91-3.83 (m, 2H), 3.72 (d, J=9.0 Hz, 1H), 3.50-3.44 (m, overlap H$_2$O, 1H), 3.32-3.16 (m, overlap H$_2$O, 2H), 2.03 (s, 3H), 1.78 (d, J=13.8 Hz, 3H), 1.61 (d, J=13.2 Hz, 1H), 1.21 (d, J=6.5 Hz, 3H).

Example 12a and 12b 6-((3S,4S)-4-Amino-3-methyl-2-oxa-8-azaspiro[4.5]decan-8-yl)-5-bromo-3-(S$_a$)-(2,3-dichlorophenyl)-2-methylpyrimidin-4(3H)-one (Example 12a)

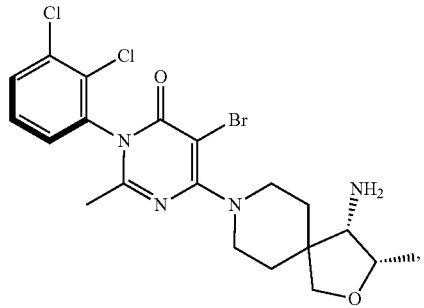

6-((3S,4S)-4-amino-3-methyl-2-oxa-8-azaspiro[4.5]decan-8-yl)-5-bromo-3-(R$_a$)-(2,3-dichlorophenyl)-2-methylpyrimidin-4(3H)-one (Example 12b)

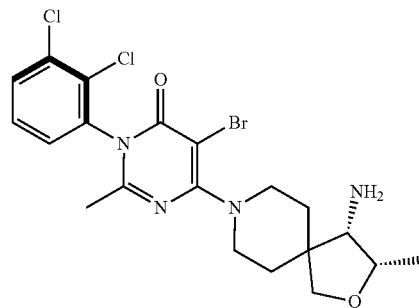

Step 1: 5-Bromo-(2,3-dichlorophenyl)-6-hydroxy-2-methylpyrimidin-4(3H)-one

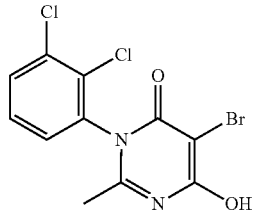 [SMILES: Cc1nc(O)c(Br)c(=O)n1-c1cccc(Cl)c1Cl]

To a solution of 3-(2,3-dichlorophenyl)-6-hydroxy-2-methylpyrimidin-4(3H)-one (Example 1, step 2) (540 mg, 2 mmol) in DCM (8 mL) was added a solution of NBS (356 mg, 2 mmol) in DCM (2 mL). The reaction mixture was stirred at rt for 2 h. The reaction mixture was filtered to afford the title compound as a white solid (680 mg, 97.1%). MS (ES+) C$_{11}$H$_7$BrCl$_2$N$_2$O$_2$ requires: 350, found: 351[M+H]+.

The compound of Step 1 can exist as a mixture of 5-bromo-(S$_a$)-(2,3-dichlorophenyl)-6-hydroxy-2-methylpyrimidin-4(3H)-one and 5-bromo-(R)-(2,3-dichlorophenyl)-6-hydroxy-2-methylpyrimidin-4(3H)-one.

Step 2: 6-((3S,4S)-4-Amino-3-methyl-2-oxa-8-azaspiro[4.5]decan-8-yl)-5-bromo-3-(R$_a$)-(2,3-dichlorophenyl)-2-methylpyrimidin-4(3H)-one (Example 12a) and 6-((3S,4S)-4-amino-3-methyl-2-oxa-8-azaspiro[4.5]decan-8-yl)-5-bromo-3-(S$_a$)-(2,3-dichlorophenyl)-2-methylpyrimidin-4(3H)-one (Example 12b)

5-Bromo-3-(2,3-dichlorophenyl)-6-hydroxy-2-methylpyrimidin-4(3H)-one (80 mg, 0.23 mmol), (3S,4S)-3-methyl-2-oxa-8-azaspiro[4.5]decan-4-amine (67 mg, 0.27 mmol), BOP (121 mg, 0.27 mmol) and DBU (174 mg, 1.14 mmol) in MeCN (2 mL) was stirred at rt for 2 h. The mixture was concentrated and purified by prep-HPLC (NH$_4$HCO$_3$) to afford a solid. The mixture of diastereomers were separated by Chiral SFC (Mobile phase: CO$_2$/methanol (0.2% MEA)=30/70; Flow rate: 80 g/min; 5 min; Column temperature: 35° C.; Back pressure: 100 bar; Column: AD 20*250 mm, 10 um (Daicel) to afford Example 12a as white solid (18 mg, 16%) and Example 12b as a white solid (15 mg, 13%).

Example 12a 6-((3S,4S)-4-Amino-3-methyl-2-oxa-8-azaspiro[4.5]decan-8-yl)-5-bromo-3-(S$_a$)-(2,3-dichlorophenyl)-2-methylpyrimidin-4(3H)-one: MS (ES+) C$_{20}$H$_{23}$BrCl$_2$N$_4$O$_2$ requires: 500, 502, found: 501, 503 [M+H]+; 1H NMR (500 MHz, DMSO) δ 7.83 (dd, J=8.1, 1.5 Hz, 1H), 7.62 (dd, J=8.0, 1.5 Hz, 1H), 7.56 (t, J=8.0 Hz, 1H), 4.09-4.02 (m, 1H), 3.93-3.82 (m, 2H), 3.66 (d, J=8.5 Hz, 1H), 3.50-3.36 (m, 3H), 2.91 (d, J=5.1 Hz, 1H), 2.00 (s, 3H), 1.86-1.78 (m, 1H), 1.68-1.59 (m, 1H), 1.61-1.47 (m, 2H), 1.08 (d, J=6.4 Hz, 3H).

Example 12b 6-((3S,4S)-4-Amino-3-methyl-2-oxa-8-azaspiro[4.5]decan-8-yl)-5-bromo-3-(R)-(2,3-dichlorophenyl)-2-methylpyrimidin-4(3H)-one: MS (ES+) C$_{20}$H$_{23}$BrCl$_2$N$_4$O$_2$ requires: 500, 502, found: 501, 503 [M+H]+; 1H NMR (500 MHz, DMSO) δ 7.83 (dd, J=8.0, 1.6 Hz, 1H), 7.62 (dd, J=7.9, 1.5 Hz, 1H), 7.56 (t, J=8.0 Hz, 1H), 4.10-4.00 (m, 1H), 3.94-3.82 (m, 2H), 3.66 (d, J=8.4 Hz, 1H), 3.53-3.36 (m, 3H), 2.91 (d, J=5.0 Hz, 1H), 2.00 (s, 3H), 1.81 (ddd, J=13.0, 9.3, 3.4 Hz, 1H), 1.69 (ddd, J=12.9, 9.1, 3.6 Hz, 1H), 1.61-1.46 (m, 2H), 1.08 (d, J=6.4 Hz, 3H).

Example 13a and 13b 6-((3S,4S)-4-Amino-3-methyl-2-oxa-8-azaspiro[4.5]decan-8-yl)-3-($S_a$)-(2-chloro-3-methylphenyl)-2-methylpyrimidin-4(3H)-one TFA salt (Example 13a)

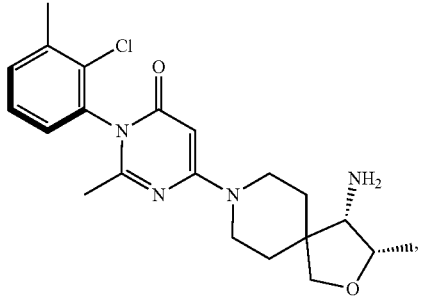

and 6-((3S,4S)-4-amino-3-methyl-2-oxa-8-azaspiro[4.5]decan-8-yl)-3-($R_a$)-(2-chloro-3-methylphenyl)-2-methylpyrimidin-4(3H)-one TFA salt (Example 13b)

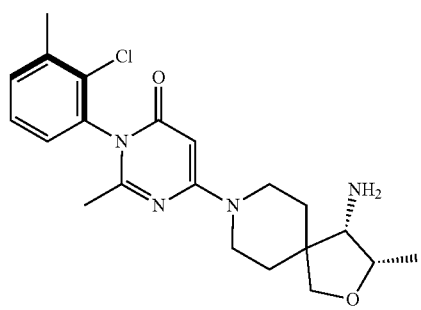

Step 1: Tert-butyl 2-chloro-3-methylphenylcarbamate

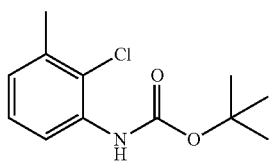 [SMILES: Cc1cccc(NC(=O)OC(C)(C)C)c1Cl]

A mixture of 1-bromo-2-chloro-3-methylbenzene (4.0 g, 19.6 mmol), Pd$_2$dba$_3$ (1014 mg, 0.98 mmol), Xantphos (566 mg, 0.98 mmol), tert-butyl carbamate (3.41 g, 29.4 mmol) and Cs$_2$CO$_3$ (9.58 g, 29.4 mmol) in dioxane (120 mL) was stirred at 110° C. for 2 h and then cooled to rt. Water (150 mL) was added and the mixture was extracted by EtOAc (150 mL×2). The organic layer was dried and concentrated. The residue was purified by flash column chromatography (PE, 100%) to afford the title compound (4.2 g, 89%). MS (ES+) C$_{12}$H$_{16}$ClNO$_2$ requires: 241, found: 187 [M−55+H]$^+$.

Step 2: 2-Chloro-3-methylaniline

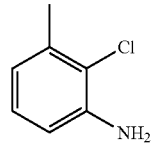

A mixture of tert-butyl 2-chloro-3-methylphenylcarbamate (4.2 g, 17.4 mmol) in 2M HCl (40 mL in MeOH) was stirred at rt for 1 h. The mixture was concentrated, washed with Et$_2$O (40 mL), and dried under vacuum to afford the title compound as a yellow solid (2.3 g, 93%). MS (ES+) C$_7$H$_8$ClN requires: 141, found: 142 [M+H]$^+$.

Step 3: N-(2-Chloro-3-methylphenyl)acetimidamide

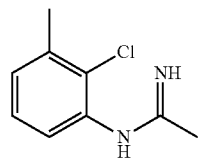

A mixture of 2-chloro-3-methylaniline (1.4 g, 9.93 mmol) in HCl (1N in CH$_3$CN, 15 ml) was heated at 120° C. for 4 h. The reaction mixture was cooled to rt, it was filtered and the filter cake was washed by Et$_2$O (15 mL). The filter cake was dried under vacuum to afford the title compound (1.2 g, 66%). MS (ES+) C$_9$H$_{11}$ClN$_2$ requires: 182, found: 183 [M+H]$^+$.

Step 4: 3-(2-Chloro-3-methylphenyl)-6-hydroxy-2-methylpyrimidin-4(3H)-one

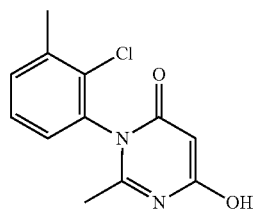 [SMILES: Cc1cccc(-n2c(C)nc(O)cc2=O)c1Cl]

To a solution of N-(2-chloro-3-methylphenyl)acetimidamide (1.2 g, 6.6 mmol) in 2-methoxyethan-1-ol (12 mL) was added diethyl malonate (4.22 g, 26.36 mmol) and CH$_3$ONa/CH$_3$OH (4M, 6.6 mL, 26 mmol). The mixture was heated at 120° C. for 16 h. The mixture was cooled to rt, it was poured into water (50 mL) and the aqueous phase was washed with Et$_2$O (50 mL). The aqueous layer was acidified to pH~2 with 6N HCl and it was extracted with EtOAc (50 mL×3). The organic layer was dried and concentrated. The residue was washed with EtOAc to afford the title compound (300 mg, 18%) as a white solid. MS (ES+) C$_{12}$H$_{11}$ClN$_2$O$_2$ requires: 250, found: 251[M+H]$^+$.

The compound of Step 4 can exist as a mixture of 3-(S$_a$) (2-chloro-3-methylphenyl)-6-hydroxy-2-methylpyrimidin-4 (3H)-one and 3-(R) (2-chloro-3-methylphenyl)-6-hydroxy-2-methylpyrimidin-4(3H)-one.

Step 5: 6-((3S,4S)-4-Amino-3-methyl-2-oxa-8-azaspiro[4.5]decan-8-yl)-3-(S$_a$)-(2-chloro-3-methylphenyl)-2-methylpyrimidin-4(3H)-one TFA salt (Example 13a) and 6-((3S,4S)-4-amino-3-methyl-2-oxa-8-azaspiro[4.5]decan-8-yl)-3-(R$_a$)-(2-chloro-3-methylphenyl)-2-methylpyrimidin-4(3H)-one TFA salt (Example 13b)

To a suspension of 3-(2-chloro-3-methylphenyl)-6-hydroxy-2-methylpyrimidin-4(3H)-one (150 mg, 0.6 mmol) and (3S,4S)-3-methyl-2-oxa-8-azaspiro[4.5]decan-4-amine dihydrochloride (173 mg, 0.72 mmol) in MeCN (3 ml) were added DBU (183 mg, 1.2 mmol) and BOP (318 mg, 0.72 mmol) and the resulting mixture was stirred at rt for 1 h. The mixture was concentrated under reduced pressure. The residue was purified by prep-HPLC (A: water (0.05% TFA), B: ACN), 18-28% B in 10 min, stop at 15 min. Column: Sunfire prep C18 10 μm, OBD 19*250 mm) to afford the title compound TFA salt Example 13a, (40 mg, 25%) and the title compound TFA salt Example 13b (60 mg, 38%).

Example 13a 6-((3S,4S)-4-Amino-3-methyl-2-oxa-8-azaspiro[4.5]decan-8-yl)-3-(S$_a$)-(2-chloro-3-methylphenyl)-2-methylpyrimidin-4(3H)-one TFA salt: MS (ES+) C$_{23}$H$_{28}$ClF$_3$N$_4$O$_4$ requires: 402, found: 403 [M+H]$^+$; 1H NMR (500 MHz, DMSO) δ 7.92 (s, 3H), 7.49-7.48 (m, 1H), 7.41-7.38 (m, 1H), 7.29-7.28 (m, 1H), 5.43 (s, 1H), 4.21-4.19 (m, 2H), 3.87-3.85 (m, 1H), 3.70-3.68 (m, 1H), 3.41-3.39 (m, 2H), 3.05-3.02 (m, 2H), 2.41 (s, 3H), 1.96 (s, 3H), 1.69-1.68 (m, 3H), 1.55-1.53 (m, 1H), 1.21-1.20 (d, J=7 Hz, 3H).

Example 13b 6-((3S,4S)-4-Amino-3-methyl-2-oxa-8-azaspiro[4.5]decan-8-yl)-3-(R$_a$)-(2-chloro-3-methylphenyl)-2-methylpyrimidin-4(3H)-one TFA salt: MS (ES+) C$_{23}$H$_{28}$ClF$_3$N$_4$O$_4$ requires: 402, found: 403 [M+H]$^+$; 1H NMR (500 MHz, DMSO) δ 8.01 (s, 3H), 7.49-7.47 (m, 1H), 7.41-7.38 (m, 1H), 7.29-7.28 (m, 1H), 5.43 (s, 1H), 4.22-4.19 (m, 2H), 3.88-3.86 (m, 2H), 3.69-3.68 (m, 1H), 3.42-3.40 (m, 1H), 3.06-3.00 (m, 2H), 2.41 (s, 3H), 1.96 (s, 3H), 1.71-1.68 (m, 3H), 1.54-1.51 (m, 1H), 1.22-1.21 (d, J=6 Hz, 3H).

Example 14a and 14b 6-((3S,4S)-4-Amino-3-methyl-2-oxa-8-azaspiro[4.5]decan-8-yl)-3-(S$_a$)-(2-chloro-3-(trifluoromethyl)phenyl)-2-methylpyrimidin-4(3H)-one TFA salt (Example 14a)

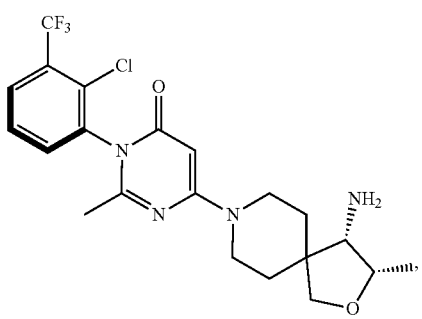

6-((3S,4S)-4-Amino-3-methyl-2-oxa-8-azaspiro[4.5]decan-8-yl)-3-(R$_a$)-(2-chloro-3-(trifluoromethyl)phenyl)-2-methylpyrimidin-4(3H)-one TFA salt (Example 14b)

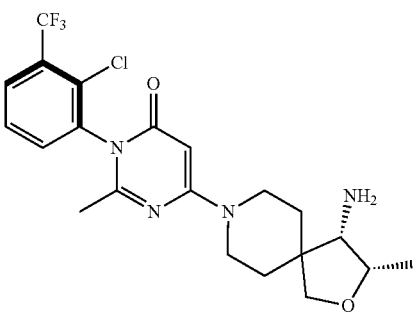

Examples 14a and 14b were synthesized with synthetic methods that were similar to that used for Examples 13a and 13b, and can generally be made by methods disclosed herein. The Examples may be made as free bases or as TFA salts.

Example 14a 6-((3S,4S)-4-Amino-3-methyl-2-oxa-8-azaspiro[4.5]decan-8-yl)-3-(S)-(2-chloro-3-(trifluoromethyl)phenyl)-2-methylpyrimidin-4(3H)-one TFA salt: MS (ES+) C$_{21}$H$_{24}$ClF$_3$N$_4$O$_2$ requires: 456, found: 457 [M+H]$^+$.

Example 14b 6-((3S,4S)-4-Amino-3-methyl-2-oxa-8-azaspiro[4.5]decan-8-yl)-3-(R$_a$)-(2-chloro-3-(trifluoromethyl)phenyl)-2-methylpyrimidin-4(3H)-one TFA salt: MS (ES+) C$_{21}$H$_{24}$ClF$_3$N$_4$O$_2$ requires: 456, found: 457 [M+H]$^+$.

Example 15a and 15b 6-((3S,4S)-4-Amino-3-methyl-2-oxa-8-azaspiro[4.5]decan-8-yl)-3-(S$_a$)-(2,3-dichloro-4-phenoxyphenyl)-2-methylpyrimidin-4(3H)-one (Example 15a)

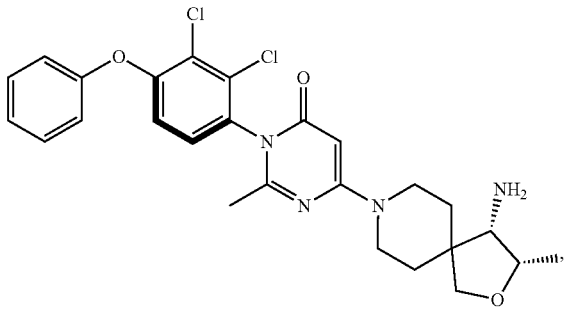

6-((3S,4S)-4-amino-3-methyl-2-oxa-8-azaspiro[4.5]decan-8-yl)-3-(R$_a$)-(2,3-dichloro-4-phenoxyphenyl)-2-methylpyrimidin-4(3H)-one (Example 15b)

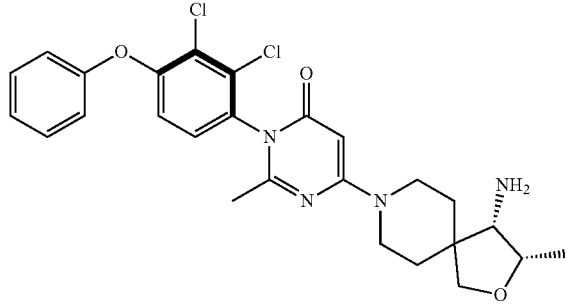

Step 1: 2,3-Dichloro-1-nitro-4-phenoxybenzene

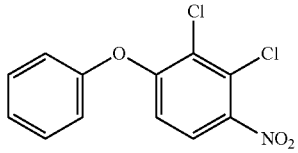 [SMILES: O=[N+]([O-])c1ccc(Oc2ccccc2)c(Cl)c1Cl]

To a solution of phenol (1.1 g, 12 mmol) in dry N,N-dimethylformamide (15 mL) was added NaH (520 mg, 13 mmol, 60%) by small portions at 0° and the resulting mixture was stirred at 0° C. for 10 min. 2,3-Dichloro-1-fluoro-4-nitrobenzene (2.1 g, 10 mmol) was added and the mixture was warmed to rt and stirred overnight. The mixture was purified by silica gel chromatography (EtOAc in PE, 0 to 15%) to afford the title compound (2.0 g, 67%) as a yellow solid. MS (ES+) $C_{12}H_7Cl_2NO_3$ requires 282; found: 283.

Step 2: 2,3-Dichloro-4-phenoxyaniline

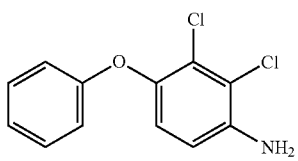 [SMILES: Nc1ccc(Oc2ccccc2)c(Cl)c1Cl]

2,3-Dichloro-1-nitro-4-phenoxybenzene (1.8 g, 6.4 mmol) and SnCl$_2$.2H$_2$O (14.3 g, 64 mmol) in EtOH (20 mL) was stirred at 85° C. for 5 h. The resulting mixture was adjusted to pH>9 with aq. sat. NaHCO$_3$, the solid was filtered and washed with EtOAc (50 mL×3). The organic phase was dried, concentrated under reduced pressure and purified by silica gel chromatography (EtOAc in PE, 0 to 40%) to afford the title compound (1.2 g, 73%) as a tan solid. MS (ES+) $C_{12}H_9Cl_2NO$ requires 252; found: 253.

Step 3: N-(2,3-Dichloro-4-phenoxyphenyl)acetimidamide

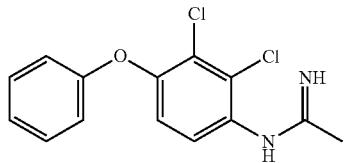 [SMILES: CC(=N)Nc1ccc(Oc2ccccc2)c(Cl)c1Cl]

2,3-Dichloro-4-phenoxyaniline (1.0 g, 3.9 mmol) in HCl/MeCN (1M, 20 mL) was heated in a sealed tube at 120° C. overnight. The mixture was cooled to rt, the solid was filtered and washed with MeCN (5 mL) to afford the title compound (0.9 g, 70%) as a white solid. MS (ES+) $C_{14}H_{12}Cl_2N_2$ requires 293, found: 294.

Step 4: 3-(2,3-dichloro-4-phenoxyphenyl)-6-hydroxy-2-methylpyrimidin-4(3H)-one

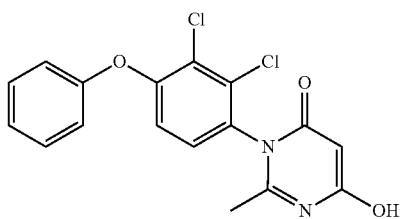 [SMILES: Cc1nc(O)cc(=O)n1-c1ccc(Oc2ccccc2)c(Cl)c1Cl]

The reaction was performed as described for Example 1, Step 2, Method B to provide the title compound (0.5 g, 54%) as a tan solid. MS (ES+) $C_{17}H_{12}Cl_2N_2O_3$ requires 361; found 362.

The compound of Step 4 can exist as a mixture of 3-(S$_a$)-(2,3-dichloro-4-phenoxyphenyl)-6-hydroxy-2-methylpyrimidin-4(3H)-one and 3-(R$_a$)-(2,3-dichloro-4-phenoxyphenyl)-6-hydroxy-2-methylpyrimidin-4(3H)-one.

Step 5: 6-((3S,4S)-4-Amino-3-methyl-2-oxa-8-azaspiro[4.5]decan-8-yl)-3-(S$_a$)-(2,3-dichloro-4-phenoxyphenyl)-2-methylpyrimidin-4(3H)-one (Example 15a) and 6-((3S,4S)-4-amino-3-methyl-2-oxa-8-azaspiro[4.5]decan-8-yl)-3-(R$_a$)-(2,3-dichloro-4-phenoxyphenyl)-2-methylpyrimidin-4(3H)-one (Example 15b)

The reaction was performed as described for Example 2, Step 1. The mixture of diastereomers were separated by Chiral SFC chiral-HPLC (co-solvent: MeOH (0.2% methanol-ammonia), Column: AD-H, 4.6×100 mm) to provide title compounds Example 15a (25 mg, 18%) and 15b (27 mg, 19%).

Example 15a 6-((3S,4S)-4-Amino-3-methyl-2-oxa-8-azaspiro[4.5]decan-8-yl)-3-(S$_a$)-(2,3-dichloro-4-phenoxyphenyl)-2-methylpyrimidin-4(3H)-one: MS (ES+) $C_{26}H_{28}Cl_2N_4O_3$ requires: 514, found: 515 [M+H]$^+$; $^1$H NMR (400 MHz, MeOD) δ 7.44 (m, 2H), 7.37 (dd, J=9, 2 Hz, 1H), 7.24 (t, J=7.5 Hz, 1H), 7.12 (dd, J=9, 1 Hz, 1H), 7.07 (dd, J=9, 2 Hz, 1H), 5.51 (s, 1H), 4.25 (m, 1H), 4.07 (m, 2H), 3.88 (d, J=9 Hz, 1H), 3.74 (m, 1H), 3.73 (d, J=9 Hz, 1H), 3.42 (m, 1H), 3.03 (d, J=5 Hz, 1H), 2.13 (s, 3H), 1.83-1.67 (m, 4H), 1.23 (d, J=6 Hz, 3H).

Example 15b 6-((3S,4S)-4-amino-3-methyl-2-oxa-8-azaspiro[4.5]decan-8-yl)-3-($R_a$)-(2,3-dichloro-4-phenoxyphenyl)-2-methylpyrimidin-4(3H)-one: MS (ES+) $C_{26}H_{28}Cl_2N_4O_3$ requires 514; found: 515 [M+H]$^+$; 1H NMR (500 MHz, MeOD) δ 7.51-7.41 (m, 2H), 7.36 (dd, J=8.8, 2.7 Hz, 1H), 7.24 (t, J=7.4 Hz, 1H), 7.12 (dd, J=8.6, 0.8 Hz, 2H), 7.07 (dd, J=8.8, 1.8 Hz, 1H), 5.51 (d, J=7.5 Hz, 1H), 4.30-4.21 (m, 1H), 4.07 (d, J=4.8 Hz, 1H) 4.07 (m, 1H), 3.89 (d, J=8.7 Hz, 1H), 3.74 (d, J=8.7 Hz, 1H), 3.42 (t, J=10.0 Hz, 1H), 3.03 (d, J=5.0 Hz, 1H), 2.14 (d, J=3.9 Hz, 3H), 1.89-1.61 (m, 4H), 1.23 (dd, J=11.7, 6.4 Hz, 3H).

Example 16a and 16b 6-((3S,4S)-4-Amino-3-methyl-2-oxa-8-azaspiro[4.5]decan-8-yl)-3-($S_a$)-(2,3-dichloro-4-((1-methyl-1H-pyrazol-3-yl)oxy)phenyl)-2-methylpyrimidin-4(3H)-one TFA salt (Example 16a)

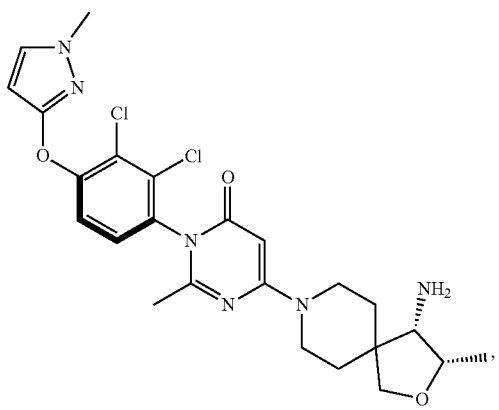

and 6-((3S,4S)-4-Amino-3-methyl-2-oxa-8-azaspiro[4.5]decan-8-yl)-3-($R_a$)-(2,3-dichloro-4-((1-methyl-1H-pyrazol-3-yl)oxy)phenyl)-2-methylpyrimidin-4(3H)-one TFA salt (Example 16b)

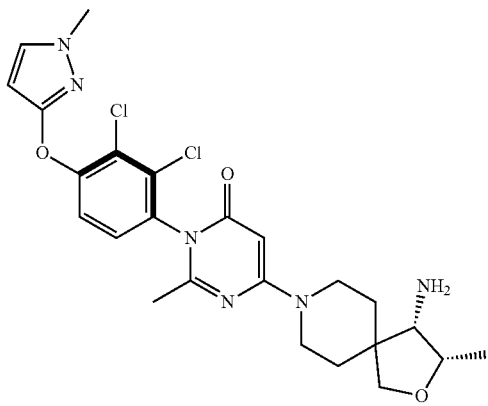

Examples 16a and 16b were synthesized with synthetic methods that were similar to that used for Examples 15a and 15b, and can generally be made by methods disclosed herein. The Examples may be made as free bases or as TFA salts.

Example 16a 6-((3S,4S)-4-Amino-3-methyl-2-oxa-8-azaspiro[4.5]decan-8-yl)-3-($S_a$)-(2,3-dichloro-4-((1-methyl-1H-pyrazol-3-yl)oxy)phenyl)-2-methylpyrimidin-4(3H)-one TFA salt: MS (ES+) $C_{24}H_{28}Cl_2N_6O_3$ requires: 518, found: 519 [M+H]$^+$.

Example 16b 6-((3S,4S)-4-amino-3-methyl-2-oxa-8-azaspiro[4.5]decan-8-yl)-3-($R_a$)-(2,3-dichloro-4-((1-methyl-1H-pyrazol-3-yl)oxy)phenyl)-2-methylpyrimidin-4(3H)-one TFA salt: MS (ES+) $C_{24}H_{28}Cl_2N_6O_3$ requires: 518, found: 519 [M+H]$^+$.

Example 17

6-((3S,4S)-4-Amino-3-methyl-2-oxa-8-azaspiro[4.5]decan-8-yl)-5-chloro-3-(2,3-dichloropyridin-4-yl)-2-methylpyrimidin-4(3H)-one

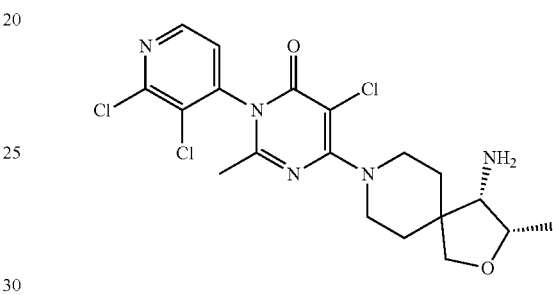

Step 1: N-(2,3-Dichloropyridin-4-yl)acetimidamide

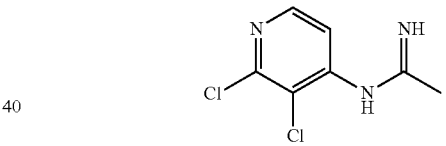

To a solution of 2,3-dichloro-4-iodopyridine (Ig mg, 3.6 mmol) in DMF (5 ml) were added acetimidamide hydrochloride (345 mg, 3.65 mmol), $Cs_2CO_3$ (2.4 g, 7.4 mmol) and Cu(I)I (70 mg, 0.36 mmol) and the resulting mixture was stirred at 90° C. for 12 h. The reaction mixture was diluted with MeCN (20 ml), filtered through Celite, and the filtrate was concentrated under reduced pressure to provide the title compound as a gray solid (0.83 g, 100%).

Step 2: 3-(2,3-Dichloropyridin-4-yl)-6-hydroxy-2-methylpyrimidin-4(3H)-one

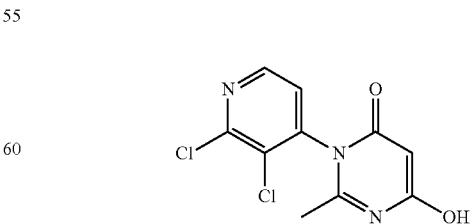

To a suspension of N-(2,3-dichloropyridin-4-yl)acetimidamide(1) (500 mg, 2.45 mmol) in THF (5 ml) was added bis(2,4,6-trichlorophenyl) malonate (1.2 g mg, 2.6 mmol)

and the resulting mixture was stirred at 90° C. for 2 h. The volatiles were removed under reduced pressure. The reaction mixture was diluted with EtOAc (20 mL) and washed with water (5 mL). The layers were separated, and the organic layer was washed with brine (5 mL), dried over MgSO$_4$, filtered and concentrated under reduced pressure. The residue was purified via silica gel chromatography (0-20% MeOH in DCM to provide the title compound (280 mg, 42% yield) as a light orange solid. MS (ES+) C$_{10}$H$_7$Cl$_2$N$_3$O$_2$ requires: 271, found: 272 [M+H]$^+$.

The compound of Step 2 can exist as a mixture of 3-(R$_a$)-(2,3-Dichloropyridin-4-yl)-6-hydroxy-2-methylpyrimidin-4(3H)-one and 3-(S$_a$)-(2,3-dichloropyridin-4-yl)-6-hydroxy-2-methylpyrimidin-4(3H)-one.

Step 3: 6-((3S,4S)-4-Amino-3-methyl-2-oxa-8-azaspiro[4.5]decan-8-yl)-3-(2,3-dichloropyridin-4-yl)-2-methylpyrimidin-4(3H)-one

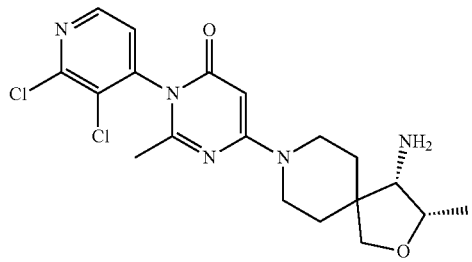 [SMILES: Cc1nc(N2CCC3(CC2)CO[C@@H](C)[C@H]3N)cc(=O)n1-c1ccnc(Cl)c1Cl]

To 3-(2,3-dichloropyridin-4-yl)-6-hydroxy-2-methylpyrimidin-4(3H)-one (100 mg, 0.37 mol), (3S,4S)-3-methyl-2-oxa-8-azaspiro[4.5]decan-4-amine dihydrochloride (89 mg, 0.37 mmol), BOP (244 mg, 0.551 mmol) in DMF (2 ml) was added DBU (0.11 ml, 0.73 mmol) and the resulting mixture was stirred at rt for 1 h. The residue was purified by mass-triggered preparative HPLC (Mobile phase: A=0.1% TFA/H$_2$O, B=0.1% TFA/MeCN; Gradient: B=10-50%; 20 min; Column: C18) to provide the title compound (92 mg, 0.22 mmol, 59% yield) as a white solid. MS (ES+) C$_{19}$H$_{23}$Cl$_2$N$_5$O$_2$ requires: 423, found: 424 [M+H]$^+$.

The compound of Step 3 can exist as a mixture of 6-((3S,4S)-4-amino-3-methyl-2-oxa-8-azaspiro[4.5]decan-8-yl)-3-(R)-(2,3-dichloropyridin-4-yl)-2-methylpyrimidin-4(3H)-one and 6-((3S,4S)-4-amino-3-methyl-2-oxa-8-azaspiro[4.5]decan-8-yl)-3-(S$_a$)-(2,3-dichloropyridin-4-yl)-2-methylpyrimidin-4(3H)-one.

Step 4: 6-((3S,4S)-4-Amino-3-methyl-2-oxa-8-azaspiro[4.5]decan-8-yl)-5-chloro-3-(2,3-dichloropyridin-4-yl)-2-methylpyrimidin-4(3H)-one A vial was charged with 6-((3S,4S)-4-amino-3-methyl-2-oxa-8-azaspiro[4.5]decan-8-yl)-3-(2,3-dichloropyridin-4-yl)-2-methylpyrimidin-4(3H)-one (40 mg, 0.047 mmol), NCS (15 mg, 0.11 mmol) and DCM (1.0 ml). The mixture was stirred at rt for 5 min. The volatiles were removed under reduced pressure. The residue was purified by mass-triggered preparative HPLC (Mobile phase: A=0.1% TFA/H$_2$O, B=0.1% TFA/MeCN; Gradient: B=10-40%; 20 min; Column: C18) to provide the title compound (12 mg, 0.026 mmol, 11% yield) as a white powder. MS (ES+) C$_{19}$H$_{22}$Cl$_3$N$_5$O$_2$ requires: 457, found: 458 [M+H]$^+$; $^1$H NMR (500 MHz, DMSO-d$_6$) δ 8.64 (d, J=5.0 Hz, 1H); 7.94 (m, 2H); 7.82 (m. 1H); 4.16-4.26 (m, 2H); 3.86 (m, 1H); 3.71 (d, J=10 Hz, 1H); 3.17-3.26 (m, 3H); 2.81 (d, J=10.68 Hz, 1H), 2.06 (s, 3H), 1.73-1.81 (m, 3H), 1.62 (m, 1H), 1.22 (d, J=5.0 Hz, 3H).

The compound of Example 17 can exist as a mixture of 6-((3S,4S)-4-amino-3-methyl-2-oxa-8-azaspiro[4.5]decan-8-yl)-5-chloro-3-(S$_a$)-(2,3-dichloropyridin-4-yl)-2-methylpyrimidin-4(3H)-one and 6-((3S,4S)-4-amino-3-methyl-2-oxa-8-azaspiro[4.5]decan-8-yl)-5-chloro-3-(R$_a$)-(2,3-dichloropyridin-4-yl)-2-methylpyrimidin-4(3H)-one.

Example 18a and 18b 6-((3S,4S)-4-Amino-3-methyl-2-oxa-8-azaspiro[4.5]decan-8-yl)-3-(S$_a$)-(2,3-dichloro-4-((1-methyl-1H-pyrazol-3-yl)oxy)phenyl)-2,5-dimethylpyrimidin-4(3H)-one (Example 18a)

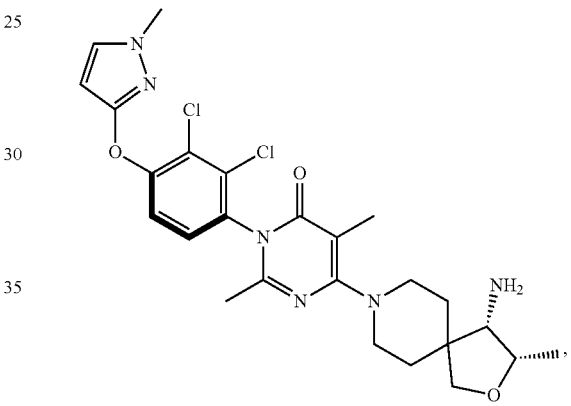

and 6-((3S,4S)-4-amino-3-methyl-2-oxa-8-azaspiro[4.5]decan-8-yl)-3-(R$_a$)-(2,3-dichloro-4-((1-methyl-1H-pyrazol-3-yl)oxy)phenyl)-2,5-dimethylpyrimidin-4(3H)-one (Example 18b)

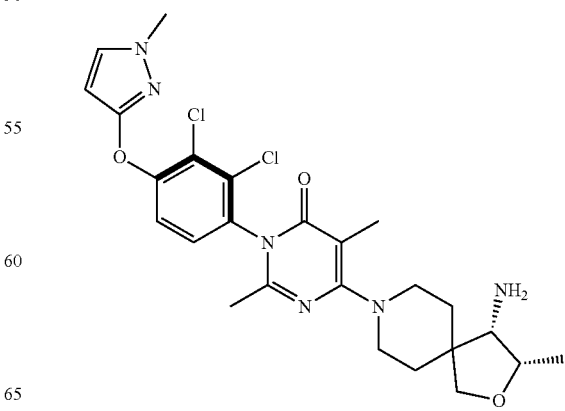

Step 1: 3-(2,3-Dichloro-4-nitrophenoxy)-1-methyl-1H-pyrazole

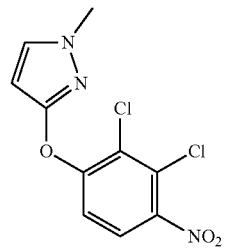 [SMILES: Cn1ccc(Oc2ccc([N+](=O)[O-])c(Cl)c2Cl)n1]

A mixture of 2,3-dichloro-1-fluoro-4-nitrobenzene (1.3 g, 6.2 mmol), 1-methyl-1,2-dihydro-3H-pyrazol-3-one (729 mg, 7.4 mmol), $K_2CO_3$ (1.7 g, 12.4 mmol) in MeCN (30 mL) was stirred at rt for 3 h. The reaction mixture was poured into water (50 ml) and extracted with EtOAc (100 mL×3). The combined organic phases were dried ($Na_2SO_4$), filtered, and concentrated and the residue was purified by silica gel chromatography (EtOAc in PE, 10%) to provide the title compound (1.5 g, 84%) as a white solid. MS (ES$^+$) $C_{10}H_7Cl_2N_3O_3$ requires: 287; found: 288 [M+H]$^+$.

Step 2: 2,3-Dichloro-4-((1-methyl-1H-pyrazol-3-yl)oxy)aniline

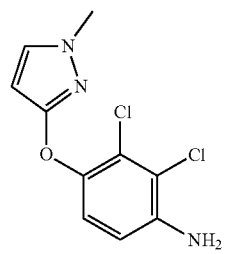

To a solution of 3-(2,3-dichloro-4-nitrophenoxy)-1-methyl-1H-pyrazole (1.5 g, 5.2 mmol) in AcOH (10 mL) was added Fe (1.4 g, 26 mmol). The resulting mixture was stirred at 60° C. for 2 h. The reaction mixture was poured into ice water (60 ml) and extracted with EtOAc (100 mL×3). The combined organic phases were dried ($Na_2SO_4$), filtered and concentrated. The residue was purified by silica gel chromatography (EtOAc in PE, 50%) to provide the title compound (1.2 g, 90%) as a yellow solid. MS (ES+) $C_{10}H_9Cl_2N_3O$ requires: 257, found: 258[M+H]$^+$.

Step 3: N-(2,3-Dichloro-4-((1-methyl-1H-pyrazol-3-yl)oxy)phenyl) acetimidamide

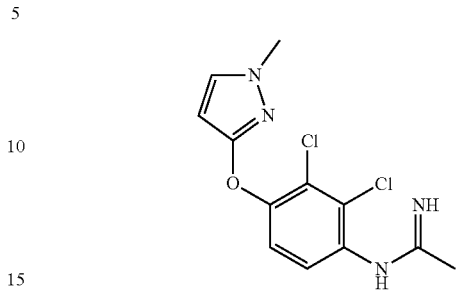

A mixture of 2,3-dichloro-4-((1-methyl-1H-pyrazol-3-yl)oxy)aniline (1.2 g, 4.7 mmol) in HCl/$CH_3CN$ (1 M, 10 mL) was stirred in a seal tube at 120° C. for 24 h. The mixture was concentrated and the residue was washed with $Et_2O$ (10 mL). The precipitate was filtered to provide the title compound (1.2 g, 86%) as a white solid. MS (ES+) $C_{12}H_{12}Cl_2N_4O$ requires: 298, found: 299[M+H]$^+$.

Step 4: 3-(2,3-Dichloro-4-((1-methyl-1H-pyrazol-3-yl)oxy)phenyl)-6-hydroxy-2,5-dimethylpyrimidin-4(3H)-one

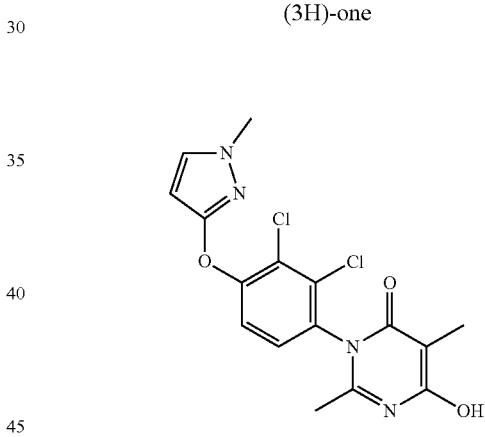

To a solution of diethyl 2-methylmalonate (1.4 g, 8.0 mmol) in EtOH (6 mL) was added $CH_3ONa$/$CH_3OH$ (4 M, 2 mL). The mixture was stirred at rt for 10 min. N-(2,3-Dichloro-4-((1-methyl-1H-pyrazol-3-yl)oxy)phenyl)acetimidamide (600 mg, 2 mmol) was added and the mixture was stirred at 120° C. for 4 h. The mixture was poured into water (30 mL) and extracted with $Et_2O$ (30 mL×2). The pH of the aqueous layer was adjusted pH 5 by AcOH and extracted with EtOAc (80 mL×3). The combined organic phases were dried ($Na_2SO_4$), filtered and concentrated. The crude product was washed with $Et_2O$ (10 mL) to provide the title compound (320 mg, 42%) as a white solid. MS (ES+) $C_{16}H_{14}Cl_2N_4O_3$ requires: 380, found: 381 [M+H]$^+$.

The compound of Step 4 can exist as a mixture of 3-($S_a$)-(2,3-dichloro-4-((1-methyl-1H-pyrazol-3-yl)oxy)phenyl)-6-hydroxy-2,5-dimethylpyrimidin-4(3H)-one and 3-(R)-(2,3-dichloro-4-((1-methyl-1H-pyrazol-3-yl)oxy)phenyl)-6-hydroxy-2,5-dimethylpyrimidin-4(3H)-one.

Step 5: 6-((3S,4S)-4-Amino-3-methyl-2-oxa-8-azaspiro[4.5]decan-8-yl)-3-(S$_a$)-(2,3-dichloro-4-((1-methyl-1H-pyrazol-3-yl)oxy)phenyl)-2,5-dimethylpyrimidin-4(3H)-one (Example 18a) and 6-((3S,4S)-4-Amino-3-methyl-2-oxa-8-azaspiro[4.5]decan-8-yl)-3-(R$_a$)-(2,3-dichloro-4-((1-methyl-1H-pyrazol-3-yl)oxy)phenyl)-2,5-dimethylpyrimidin-4(3H)-one (Example 18b)

To a suspension of 3-(2,3-dichloro-4-((1-methyl-1H-pyrazol-3-yl)oxy)phenyl)-6-hydroxy-2,5-dimethylpyrimidin-4(3H)-one (100 mg, 0.26 mmol) and (3S,4S)-3-methyl-2-oxa-8-azaspiro[4.5]decan-4-amine dihydrochloride (126 mg, 0.52 mmol) in MeCN (8 ml) was added DBU (395 mg, 2.6 mmol) and BOP (230 mg, 0.52 mmol) and the resulting mixture was stirred at rt for 48 h. The mixture was concentrated under reduced pressure and the residue was purified by preparative HPLC (Mobile phase: A=0.05% TFA/H$_2$O, B=MeCN; Gradient: B=21-31%; 10 min; Column: C18) and the diastereomers were separated using a Chiralpak OZ Column (20×250 mm) with CO$_2$ and 0.2% methanol ammonia (45:55) as an eluent, a flow rate of 80 g/min and UV detection (214 nm) to provide Example 18a (7 mg, 5%) and Example 18b (9 mg, 7%) as a white solid.

Example 18a 6-((3S,4S)-4-Amino-3-methyl-2-oxa-8-azaspiro[4.5]decan-8-yl)-3-(S$_a$)-(2,3-dichloro-4-((1-methyl-1H-pyrazol-3-yl)oxy)phenyl)-2,5-dimethylpyrimidin-4 (3H)-one: MS (ES+) C$_{25}$H$_{30}$Cl$_2$N$_6$O$_3$ requires: 532 found: 533 [M+H]$^+$; $^1$H NMR (500 MHz, MeOD) δ 7.46 (d, J=2.5 Hz, 1H), 7.14-7.23 (m, 2H), 5.84 (d, J=2.5 Hz, 1H), 4.12-4.15 (m, 1H), 3.71-3.78 (m, 1H), 3.62-3.68 (m, 6H), 3.17-3.20 (m, 3H), 2.95-2.96 (m, 1H), 1.99 (s, 3H), 1.90 (s, 3H), 1.57-1.78 (m, 4H), 1.18 (s, 1H), 1.12 (d, J=6 Hz, 3H).

Example 18b 6-((3S,4S)-4-Amino-3-methyl-2-oxa-8-azaspiro[4.5]decan-8-yl)-3-(R$_a$)-(2,3-dichloro-4-((1-methyl-1H-pyrazol-3-yl)oxy)phenyl)-2,5-dimethylpyrimidin-4(3H)-one: MS (ES+) C$_{25}$H$_{30}$Cl$_2$N$_6$O$_3$ requires: 532 found: 533 [M+H]$^+$; $^1$H NMR (500 MHz, MeOD) δ 7.58 (d, J=2.5 Hz, 1H), 7.26-7.36 (m, 2H), 5.96 (d, J=3 Hz, 1H), 4.24-4.26 (m, 1H), 3.83-3.89 (m, 1H), 3.74-3.80 (m, 6H), 3.18-3.29 (m, 3H), 3.05-3.06 (m, 1H), 2.69 (s, 1H), 2.11 (s, 3H), 2.02 (s, 3H), 1.66-1.88 (m, 4H), 1.23 (d, J=7 Hz, 3H).

Example 19a and 19b 4-(4-(4-((3S,4S)-4-Amino-3-methyl-2-oxa-8-azaspiro[4.5]decan-8-yl)-2,5-dimethyl-6-oxopyrimidin-1(6H)-yl)-(S$_a$)-(2,3-dichlorophenoxy)-N-methylbenzamide (Example 19a)

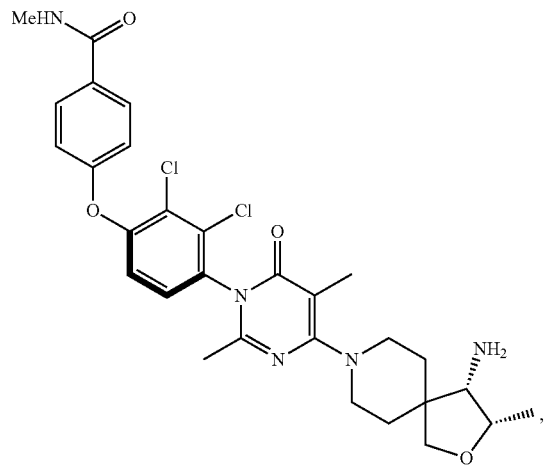

and 4-(4-(4-((3S,4S)-4-Amino-3-methyl-2-oxa-8-azaspiro[4.5]decan-8-yl)-2,5-dimethyl-6-oxopyrimidin-1(6H)-yl)-(R)-(2,3-dichlorophenoxy)-N-methylbenzamide (Example 19b)

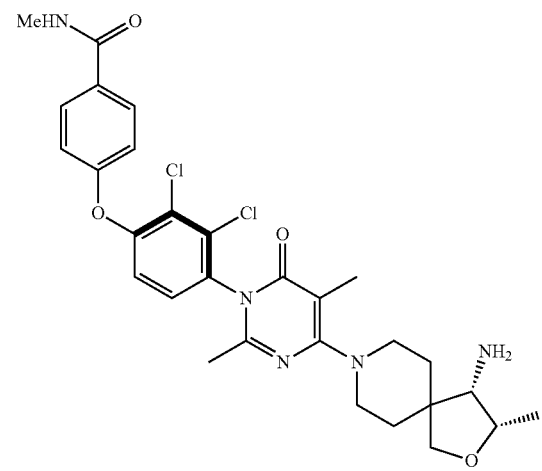

Examples 19a and 19b were synthesized with synthetic methods that were similar to that used for Examples 15a and 15b, and can generally be made by methods disclosed herein. The Examples may be made as free bases or as TFA salts.

Example 19a 4-(4-(4-((3S,4S)-4-Amino-3-methyl-2-oxa-8-azaspiro[4.5]decan-8-yl)-2,5-dimethyl-6-oxopyrimidin-1(6H)-yl)-(S$_a$)-(2,3-dichlorophenoxy)-N-methylbenzamide: MS (ES+) C$_{29}$H$_{33}$Cl$_2$N$_5$O$_4$ requires: 585, found: 586 [M+H]$^+$.

Example 19b 4-(4-(4-((3S,4S)-4-Amino-3-methyl-2-oxa-8-azaspiro[4.5]decan-8-yl)-2,5-dimethyl-6-oxopyrimidin-1

(6H)-yl)-($R_a$)-(2,3-dichlorophenoxy)-N-methylbenzamide: MS (ES+) $C_{29}H_{33}Cl_2N_5O_4$ requires: 585, found: 586 [M+H]$^+$.

Example 20a and 20b 3-(4-((1H-Pyrazol-3-yl)oxy)-($S_a$)-2,3-dichlorophenyl)$_6$-((3S,4S)-4-amino-3-methyl-2-oxa-8-azaspiro[4.5]decan-8-yl)-2,5-dimethylpyrimidin-4(3H)-one (Example 20a)

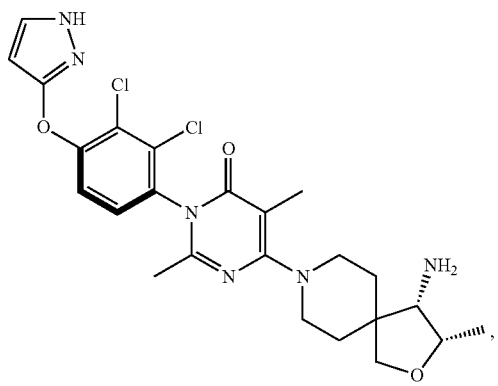

and 3-(4-((1H-pyrazol-3-yl)oxy)-($R_a$)-2,3-dichlorophenyl)-6-((3S,4S)-4-amino-3-methyl-2-oxa-8-azaspiro[4.5]decan-8-yl)-2,5-dimethylpyrimidin-4(3H)-one (Example 20b)

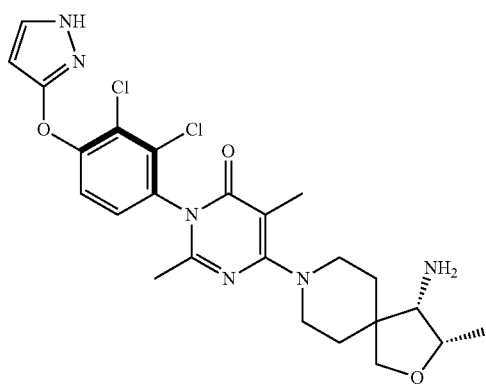

Step 1: tert-Butyl 3-(2,3-dichloro-4-nitrophenoxy)-1H-pyrazole-1-carboxylate

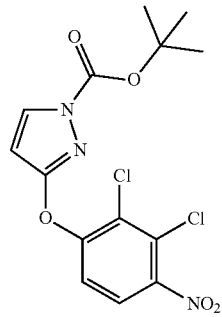 [SMILES: CC(C)(C)OC(=O)n1ccc(Oc2ccc([N+](=O)[O-])c(Cl)c2Cl)n1]

A mixture of tert-butyl 3-oxo-2,3-dihydro-1H-pyrazole-1-carboxylate (687 mg, 3.73 mmol), 2,3-dichloro-1-fluoro-4-nitrobenzene (650 mg, 3.11 mmol) and $K_2CO_3$ (858 mg, 6.22 mmol) in DMSO (10 mL) was stirred at rt for 4 h. Water (20 mL) was added and the mixture was extracted with EtOAc. The combined organic phases were dried over $Na_2SO_4$, filtered and purified by column chromatography (EtOAc in PE; 20 to 50%) to afford the title compound (800 mg, 67%) as a yellow solid. MS (ES+) $C_{14}H_{13}Cl_2N_3O_5$ requires: 373, found: 318 [M−56+H]$^+$.

Step 2: tert-Butyl 3-(4-amino-2,3-dichlorophenoxy)-1H-pyrazole-1-carboxylate

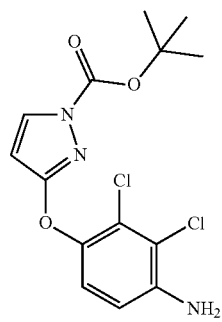

A suspension of tert-butyl 3-(2,3-dichloro-4-nitrophenoxy)-1H-pyrazole-1-carboxylate (1.2 g 3.2 mmol), Pt/C (200 mg) in EtOH (100 mL) was stirred under Hz atmosphere at rt for 16 h. The mixture was filtered and the filtrate was concentrated to afford the title compound (1.1 g, 100%) as a beige solid. MS (ESI+) $C_{14}H_{15}Cl_2N_3O_3$ requires: 343, found: 288 [M−56+H]+.

Step 3: N-(4-((1H-Pyrazol-3-yl)oxy)-2,3-dichlorophenyl)acetimidamide

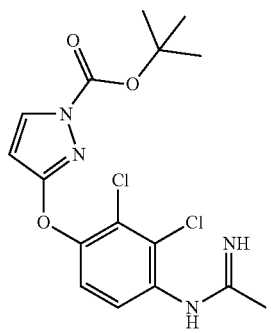 [SMILES: CC(=N)Nc1ccc(Oc2ccn(C(=O)OC(C)(C)C)n2)c(Cl)c1Cl]

A mixture of tert-butyl 3-(4-amino-2,3-dichlorophenoxy)-1H-pyrazole-1-carboxylate (1.1 g, 3.2 mmol) in HCl/CH$_3$CN (1 M, 20 mL) was stirred in a sealed tube at 110° C. for 4 h. The mixture was concentrated to give N-(4-((1H-pyrazol-3-yl)oxy)-2,3-dichlorophenyl)acetimidamide as a crude product. MS (ESI+) C$_{11}$H$_{10}$Cl$_2$N$_4$O requires: 284, found: 285 [M+H]+.

Step 4: 3-(4-((1H-Pyrazol-3-yl)oxy)-2,3-dichlorophenyl)-6-hydroxy-2,5-dimethylpyrimidin-4(3H)-one

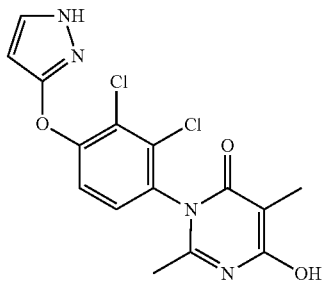 [SMILES: Cc1c(O)nc(C)n(-c2ccc(Oc3cc[nH]n3)c(Cl)c2Cl)c1=O]

A mixture of N-(4-((1H-pyrazol-3-yl)oxy)-2,3-dichlorophenyl)acetimidamide (600 mg, 2.11 mmol) diethyl 2-methylmalonate (1.84 g, 10.6 mmol) in EtOH (10 mL) was added CH$_3$ONa/CH$_3$OH (4 M, 2.64 mL). The mixture was stirred at 110° C. for 5 h. The mixture was concentrated and dissolved in water (20 mL). The aqueous layer was extracted with EtOAc (20 mL) and adjusted pH to 5 with 6 N HCl. Solid was precipitated out, it was collected by filtration to give the title compound (300 mg, 38.7%) as a beige solid. MS (ESI+) C$_{15}$H$_{12}$Cl$_2$N$_4$O$_3$ requires: 366, found: 367 [M+H]$^+$.

The compound of Step 4 can exist as a mixture of 3-(4-((1H-pyrazol-3-yl)oxy)-(S)-2,3-dichlorophenyl)-6-hydroxy-2,5-dimethylpyrimidin-4(3H)-one and 3-(4-((1H-pyrazol-3-yl)oxy)-(R)-2,3-dichlorophenyl)-6-hydroxy-2,5-dimethylpyrimidin-4(3H)-one.

Step 5: 3-(4-((1H-Pyrazol-3-yl)oxy)-(S)-2,3-dichlorophenyl)-6-((3S,4S)-4-amino-3-methyl-2-oxa-8-azaspiro[4.5]decan-8-yl)-2,5-dimethylpyrimidin-4(3H)-one (Example 20a) and 3-(4-((1H-pyrazol-3-yl)oxy)-(R$_a$)-2,3-dichlorophenyl)-6-((3S,4S)-4-amino-3-methyl-2-oxa-8-azaspiro[4.5]decan-8-yl)-2,5-dimethylpyrimidin-4(3H)-one (Example 20b)

The experiment was performed as described for Examples 18a and 18b, step 5. The mixture was separated using a Chiralpak OZ Column (20×250 mm) with CO$_2$ and 0.2% methanol ammonia (50:50) as an eluent, a flow rate of 80 g/min and UV detection (214 nm) to provide Example 20a (15 mg, 11%) and Example 20b (13 mg, 11%) as a white solid.

Example 20a 3-(4-((1H-Pyrazol-3-yl)oxy)-(S$_a$)-2,3-dichlorophenyl)-6-((3S,4S)-4-amino-3-methyl-2-oxa-8-azaspiro[4.5]decan-8-yl)-2,5-dimethylpyrimidin-4(3H)-one: MS (ES+) C$_{24}$H$_{28}$Cl$_2$N$_6$O$_3$ requires: 518, found: 519 [M+H]$^+$; 1H NMR (500 MHz, DMSO) δ 12.57 (d, J=0.4 Hz, 1H), 7.78 (s, 1H), 7.48 (d, J=8.9 Hz, 1H), 7.18 (d, J=8.9 Hz, 1H), 6.05 (s, 1H), 4.12-3.99 (m, 1H), 3.67 (d, J=8.4 Hz, 1H), 3.60-3.52 (m, 2H), 3.50 (d, J=8.4 Hz, 1H), 3.23-3.07 (m, 2H), 2.93 (d, J=4.9 Hz, 1H), 2.00 (s, 3H), 1.89 (s, 3H), 1.81-1.74 (m, 1H), 1.70-1.63 (m, 1H), 1.59-1.47 (m, 2H), 1.23 (s, 1H), 1.09 (d, J=6.3 Hz, 3H).

Example 20b 3-(4-((1H-Pyrazol-3-yl)oxy)-(R$_a$)-2,3-dichlorophenyl)-6-((3S,4S)-4-amino-3-methyl-2-oxa-8-azaspiro[4.5]decan-8-yl)-2,5-dimethylpyrimidin-4(3H)-one: MS (ES+) C$_{24}$H$_{28}$Cl$_2$N$_6$O$_3$ requires: 518, found: 519 [M+H]$^+$; 1H NMR (500 MHz, DMSO) δ 12.57 (s, 1H), 7.81-7.75 (m, 1H), 7.48 (d, J=8.9 Hz, 1H), 7.18 (d, J=9.0 Hz, 1H), 6.05 (t, J=2.1 Hz, 1H), 4.10-4.01 (m, 1H), 3.67 (d, J=8.5 Hz, 1H), 3.61-3.51 (m, 2H), 3.50 (d, J=8.5 Hz, 1H), 3.23-3.18 (m, 1H), 3.15-3.06 (m, 1H), 2.93 (d, J=4.9 Hz, 1H), 2.00 (s, 3H), 1.89 (s, 3H), 1.80-1.75 (m, 1H), 1.70-1.63 (m, 1H), 1.58-1.48 (m, 2H), 1.32-1.19 (m, 2H), 1.09 (d, J=6.4 Hz, 3H).

Example 21: Biological Activity Assay

The activity of the compounds in the Examples disclosed herein as PTPN11 inhibitors is illustrated in the following assays.
PTPN11 Enzymatic Assay Recombinant full-length wild-type and E76K mutant human PTPN11 proteins were cloned, expressed (E. coli system), and isolated via a two-step purification of Ni affinity followed by S75 size exclusion chromatography.

Phosphatase activity of full length wild-type PTPN11 (PTPN11-WT) or PTPN11-E76K mutant enzyme was measured using the fluorogenic 6,8-difluoro-4-methylumbelliferyl phosphate (DiFMUP; Molecular Probes) as the substrate. Enzyme (250 pM) was incubated with or without increasing concentrations of compounds in assay buffer (62.5 mM HEPES, 125 mM NaCl, 1 mM EDTA, 1.25 mM TECP, 0.1% BSA) for 30 min at room temperature. Reaction was initiated by addition of DiFMUP (50 μM) at room temperature in 384-well black plate with a final reaction volume of 20 uL in assay buffer. After 1 hour, DiFMUP fluorescence signal was measured (Ex: 340/Em: 460) using Envision plate reader. Dose-response curves were analyzed using IC$_{50}$ regression curve fitting (GeneData Screener). Curves were normalized to a high controls without inhibitor, and low controls without substrate. Results are provided below in Table 2.

TABLE 2

Biological Activity for inhibition of PTPN11-E76K mutant enzyme

| Example # | IC$_{50}$, nM |
|---|---|
| 1 | 510 |
| 2a | 7047 |
| 2b | 122 |
| 3 | 310 |
| 4 | 480 |
| 5 | 1172 |
| 6 | 203 |
| 7a | >10000 |
| 7b | 153 |
| 8 | 360 |
| 9 | 45 |
| 10a | 2583 |
| 10b | 28 |
| 11 | 366 |
| 12a | 3457 |
| 12b | 20 |
| 13a | 7500 |
| 13b | 186 |
| 14a | >1000 |
| 14b | 703 |
| 15a | >1000 |
| 15b | 148 |
| 16a | 9552 |
| 16b | 92 |
| 17 | 618 |
| 18a | 511 |
| 18b | 3 |
| 19b | 12 |
| 20b | 5 |

ERK Phosphorylation (Phospho-ERK) Target Engagement Assay

KYSE-520 cells (10 k cells/well) are plated onto 384-well plate in 20 uL of medium (RPMI-1640, without phenol red, containing 10/a FBS) and incubated at 37° C., 5% $CO_2$ 16 h. DMSO (control) or increasing concentrations of compounds are diluted in medium, added to the 384-well plate (10 uL/well, final DMSO concentration of 1%), and cells are then incubated with compounds for 2 hr. Phospho-ERK levels are measured using a TR-FRET based phospho-ERK1/2 HTRF kit (CisBio, 64ERKPEH) following manufacturer's recommendations, and fluorescence signal was measured at 665 nm and 620 nm using Synergy Neo plate reader. Dose-response curves were analyzed using IC$_{50}$ regression curve fitting (GeneData Screener). Curves were normalized to a high controls without inhibitor, and low controls with 1 μM of selumetinib. Some compounds of this invention showed IC$_{50}$<1 μM.

Colony Formation Assay

KYSE-520 cells (2000 cells/well) are plated in 6-well plate containing 2 mL of medium (RPMI-1640, containing 10% FBS), in presence of DMSO (control; 1% final concentration) or increasing compound concentration. After 14 days of culture at 37° C. in a humidified 5% $CO_2$ incubator, colonies are fixed and stained with 0.1% crystal violet and 15% ethanol solution. Plates are imaged and colony area quantified and normalized to DMSO with ImageJ, Colony Area plugin. (Guzmán, Camilo, PloS one 2014). Some compounds of this invention displayed IC$_{50}$<1 μM).

Example 22: In Vivo Studies

The in vivo anti-tumor efficacy of Example 2b was evaluated in NSG (NOD scid gamma) mice with subcutaneously implanted KYSE520 xenografts. Example 2b was administered by oral gavage once a day for 21 days at dosing levels of 300 mg/kg, 50 mg/kg, 15 mg/kg and 5 mg/kg. Example 2b exhibited a dose-dependent tumor growth inhibition in the KYSE520 xenograft model at tolerated dose, as shown in FIG. 1.

Figure 2:
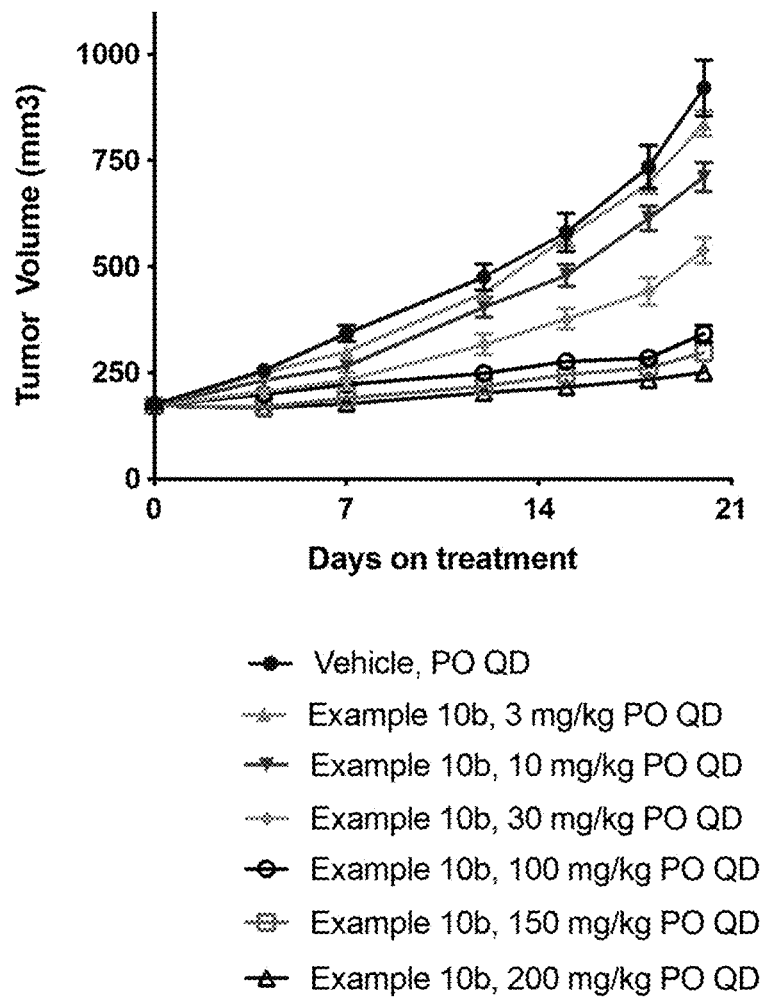
FIG. 2 shows a dose-dependent tumor growth inhibition by 6-((3S,4S)-4-amino-3-methyl-2-oxa-8-azaspiro[4.5]decan-8-yl)-3-($R_a$)-(2,3-dichlorophenyl)-2,5-dimethylpyrimidin-4(3H)-one (Example 10b) in the KYSE520 xenograft model.

The in vivo anti-tumor efficacy of Example 10b was evaluated in NSG mice with subcutaneously implanted KYSE520 xenografts. Example 10b was administered by oral gavage once a day for 21 days at 200 mg/kg, 150 mg/kg, 100 mg/kg, 30 mg/kg, 10 mg/kg and 3 mg/kg. Example 10b exhibited a dose-dependent tumor growth inhibition in the KYSE520 xenograft model at tolerated dose, as shown in FIG. 2.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

VIII. Embodiments

For further illustration, additional non-limiting embodiments of the present invention are set forth below.

Embodiment 1 is a compound represented by Formula I

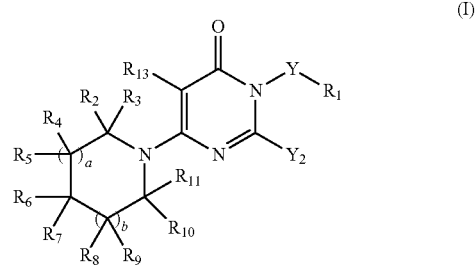

or a salt, ester, or prodrug thereof, wherein:
subscript a is 0 or 1;
subscript b is 0 or 1;
$Y_1$ is a direct bond or $CR_{17}R_{18}$;
$Y_2$ is selected from the group consisting of $C_{1-4}$alkyl, amino, $C_{1-4}$alkylC(O)O—, $C_{1-4}$alkylamino and $C_{1-4}$aminoalkyl;
$R_1$ is selected from the group consisting of $C_{6-10}$aryl, $C_{3-8}$cycloalkyl, $C_{3-8}$cycloalkenyl, and a 5-10 membered heteroaryl group having 1 to 4 heteroatoms or groups as ring vertices independently selected from N, C(O), O, and S; said aryl or heteroaryl of $R_1$ is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, $NR_{15}C(O)R_{14}$, $NR_{15}C(O)OR_{14}$, $NR_{14}C(O)NR_{15}R_{16}$, $NR_{15}S(O)R_{14}$, $NR_{15}S(O)_2R_{14}$, $C(O)NR_{15}R_{16}$, $S(O)NR_{15}R_{16}$, $S(O)_2NR_{15}R_{16}$, $C(O)R_{14}$, $C(O)OR_{14}$, $OR_{14}$, $SR_{14}$, $S(O)R_{14}$, and $S(O)_2R_{14}$;
$R_2$, $R_3$, $R_{10}$, and $R_{11}$ are each independently selected from the group consisting of hydrogen, $C_{1-4}$alkyl, and $C_{3-8}$cycloalkyl;
$R_4$, $R_5$, $R_8$, and $R_9$ are each independently selected from the group consisting of hydrogen, cyano, $C_{1-4}$alkyl, $C_{1-4}$alkoxy, amino, hydroxy, $C_{3-8}$cycloalkyl, halo, and $C_{1-4}$alkylamino;

$R_6$ is selected from the group consisting of amino, $C_{1-4}$aminoalkyl, and $C_{1-4}$alkylamino;

$R_7$ is selected from the group consisting of hydrogen, amido, cyano, halo, and hydroxy, or is selected from the group consisting of $C_{1-4}$alkyl, $C_{1-4}$hydroxyalkyl, $C_{3-6}$cycloalkyl, phenyl, and 5- or 6-membered heteroaryl, any of which is optionally substituted with one to five groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino, and $C_{1-4}$aminoalkyl;

or $R_6$ and $R_7$ together with the carbon atom to which they are both attached form a 3- to 7-membered saturated or unsaturated ring, having 0 to 3 heteroatoms or groups as ring vertices independently selected from N, C(O), O, and $S(O)_m$;

subscript m is 0, 1, or 2;

said saturated or unsaturated ring formed by $R_6$ and $R_7$ is unsubstituted or substituted with 1 to 3 groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl;

any two groups of $R_2$, $R_3$, $R_4$, $R_5$, $R_7$, $R_8$, $R_9$, $R_{10}$ and $R_{11}$ can form a 5 to 6 membered ring, having 0 to 2 heteroatoms as ring verticess elected from N, O and S;

any two groups of $R_2$, $R_4$, $R_6$, $R_5$ and $R_{10}$ can form a direct bond, or a 1 or 2 atom carbon bridge;

$R_{13}$ is selected from the group consisting of hydrogen, halo, cyano, $C_{1-6}$alkyl, $C_{1-6}$haloalkyl, $C_{1-6}$hydroxyalkyl, $C_{1-6}$ dihydroxyalkyl, —NH—NHR$_{19}$, —NHR$_{19}$, —OR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}$R$_{20}$, —C(O)NH(CH$_2$)$_q$OH, —C(O)NH(CH$_2$)$_q$R$_{21}$, —C(O)R$_{21}$, —NH$_2$, —OH, —S(O)$_2$NR$_{19}$R$_{20}$, $C_{3-8}$cycloalkyl, aryl, heterocyclyl having 1-5 heteroatoms as ring vertices selected from N, O, S and P, heteroaryl having 1-5 heteroatoms as ring vertices selected from N, O, S and P; wherein the subscript q is an integer of from 0 to 6; and wherein aryl, heteroaryl, heterocyclyl and cycloalkyl are substituted with 0 to 3 groups independently selected from the group consisting of $C_{1-4}$alkyl, —OH, —NH$_2$, —OR$_{21}$, halo, cyano, and oxo;

$R_{14}$, $R_{18}$ and $R_{16}$ are each independently selected from the group consisting of hydrogen, $C_{1-4}$alkyl, $C_{3-8}$cycloalkyl, $C_{6-10}$aryl and 5-10 membered heteroaryl, each of which is optionally substituted by one or more groups independently selected from the group consisting of amido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl;

$R_{17}$ and $R_{18}$ are each independently selected from the group consisting of hydrogen, $C_{1-4}$alkyl, and $CF_3$;

$R_{19}$ and $R_{20}$ are each independently selected from the group consisting of hydrogen, $C_{1-4}$alkyl, $C_{1-6}$haloalkyl, $C_{1-6}$hydroxyalkyl, $C_{2-6}$alkenyl, $C_{2-6}$alkynyl and $C_{3-6}$cycloalkyl; and each $R_{21}$ is independently selected from the group consisting of hydrogen, —OH, $C_{1-6}$ alkyl, $C_{1-6}$haloalkyl, $C_{1-6}$hydroxyalkyl, $C_{2-6}$alkenyl, $C_{2-6}$alkynyl and $C_{3-6}$cycloalkyl.

Embodiment 2 is the compound of embodiment 1, wherein:

subscript a is 0 or 1;

subscript b is 0 or 1;

$Y_1$ is a direct bond or $CR_{17}R_{18}$;

$Y_2$ is selected from the group consisting of $C_{1-4}$alkyl, amino, $C_{1-4}$alkylC(O)O—, $C_{1-4}$alkylamino and $C_{1-4}$aminoalkyl;

$R_1$ is selected from the group consisting of $C_{6-10}$aryl, $C_{3-8}$cycloalkyl, $C_{3-8}$cycloalkenyl, and a 5-10 membered heteroaryl group having 1 to 4 heteroatoms or groups as ring vertices independently selected from N, C(O), O, and S; said aryl or heteroaryl of $R_1$ is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, NR$_{15}$C(O)R$_{14}$, NR$_{15}$C(O)OR$_{14}$, NR$_{14}$C(O)NR$_{15}$R$_{16}$, NR$_{15}$S(O)R$_{14}$, NR$_{15}$S(O)$_2$R$_{14}$, C(O)NR$_{15}$R$_{16}$, S(O)NR$_{15}$R$_{16}$, S(O)$_2$NR$_{15}$R$_{16}$, C(O)R$_{14}$, C(O)OR$_{14}$, OR$_{14}$, SR$_{14}$, S(O)R$_{14}$, and S(O)$_2$R$_{14}$;

$R_2$, $R_3$, $R_{10}$, and $R_{11}$ are each independently selected from the group consisting of hydrogen, $C_{1-4}$alkyl, and $C_{3-8}$cycloalkyl;

$R_4$, $R_5$, $R_8$, and $R_9$ are each independently selected from the group consisting of hydrogen, cyano, $C_{1-4}$alkyl, $C_{1-4}$alkoxy, amino, hydroxy, $C_{3-8}$cycloalkyl, halo, and $C_{1-4}$alkylamino;

$R_6$ is selected from the group consisting of amino, $C_{1-4}$aminoalkyl, and $C_{1-4}$alkylamino;

$R_7$ is selected from the group consisting of hydrogen, halo, and hydroxy, or is selected from the group consisting of amido, $C_{1-4}$alkyl, $C_{1-4}$hydroxyalkyl, $C_{3-6}$cycloalkyl, phenyl, and 5- or 6-membered heteroaryl, any of which is optionally substituted with one to five groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino, and $C_{1-4}$aminoalkyl;

or $R_6$ and $R_7$ together with the carbon atom to which they are both attached form a 3- to 7-membered saturated or unsaturated ring, having 0 to 3 heteroatoms or groups as ring vertices independently selected from N, C(O), O, and $S(O)_m$;

subscript m is 0, 1, or 2;

said saturated ring formed by $R_6$ and $R_7$ is unsubstituted or substituted with 1 to 3 groups independently selected from the group consisting of amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl;

any two groups of $R_2$, $R_3$, $R_4$, $R_5$, $R_7$, $R_8$, $R_9$, $R_{10}$ and $R_{11}$ can form a 5 to 6 membered ring, having 0 to 2 heteroatoms as ring vertices selected from N, O and S;

any two groups of $R_2$, $R_4$, $R_6$, $R_8$ and $R_{10}$ can form a direct bond, or a 1 or 2 atom carbon bridge;

$R_{13}$ is selected from the group consisting of hydrogen, halo, cyano, $C_{1-6}$ alkyl, $C_{1-6}$haloalkyl, $C_{1-6}$hydroxyalkyl, $C_{1-6}$dihydroxyalkyl, —NH—NHR$_{19}$, —NHR$_{19}$, —OR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}$R$_{20}$, —C(O)NH(CH$_2$)$_q$OH, —C(O)NH(CH$_2$)$_q$R$_{21}$, —C(O)R$_{21}$, —NH$_2$, —OH, —S(O)$_2$NR$_{19}$R$_{20}$, $C_{3-8}$cycloalkyl, aryl, heterocyclyl having 1-5 heteroatoms as ring vertices selected from N, O, S and P, heteroaryl having 1-5 heteroatoms as ring vertices selected from N, O, S and P; wherein the subscript q is an integer of from 0 to 6; and wherein aryl, heteroaryl, heterocyclyl and cycloalkyl are substituted with 0 to 3 groups independently selected from the group consisting of $C_{1-4}$alkyl, —OH, —NH$_2$, —OR$_{21}$, halo, cyano, and oxo;

$R_{14}$, $R_{18}$ and $R_{16}$ are each independently selected from the group consisting of hydrogen, $C_{1-4}$alkyl, $C_{3-8}$cycloalkyl, $C_{6-10}$aryl and 5-10 membered heteroaryl, each of which is optionally substituted by one or more groups independently selected from the group consisting of halo, hydroxy, cyano, and $C_{1-4}$alkyl;

$R_{17}$ and $R_{18}$ are each independently selected from the group consisting of hydrogen, $C_{1-4}$alkyl, and $CF_3$;

$R_{19}$ and $R_{20}$ are each independently selected from the group consisting of hydrogen, $C_{1-6}$alkyl, $C_{1-6}$haloalkyl, $C_{1-6}$hydroxyalkyl, $C_{2-6}$alkenyl, $C_{2-4}$alkynyl and $C_{3-6}$cycloalkyl; and each $R_{21}$ is independently selected from the group consisting of hydrogen, —OH, $C_{1-6}$ alkyl, $C_{1-6}$haloalkyl, $C_{1-6}$hydroxyalkyl, $C_{2-6}$alkenyl, $C_{2-6}$alkynyl and $C_{3-6}$cycloalkyl.

Embodiment 3 is the compound of embodiment 1 or 2, wherein subscripts a and b are each 1.

Embodiment 4 is the compound of any one of embodiments 1 to 3, wherein $Y_1$ is a direct bond.

Embodiment 5 is the compound of any one of embodiments 1 to 4, wherein $Y_2$ is $C_{1-4}$alkyl.

Embodiment 6 is the compound of embodiment 5, wherein $Y_2$ is methyl.

Embodiment 7 is the compound of any one of embodiments 1 to 6, wherein $R_{13}$ is selected from the group consisting of hydrogen, halo, $C_{1-4}$alkyl, $C_{1-6}$haloalkyl, $C_{1-6}$hydroxyalkyl, $C_{1-6}$dihydroxyalkyl, $C_{3-8}$cycloalkyl, a 3- or 6-membered heterocyclyl having 1-3 heteroatoms as ring vertices selected from N, O and S; wherein heterocyclyl and cycloalkyl are substituted with 0 to 3 groups independently selected from the group consisting of $C_{1-4}$alkyl, —OH, —NH$_2$, —OR$_{21}$, halo, cyano and oxo.

Embodiment 8 is the compound of embodiment 7, wherein $R_{13}$ is selected from the group consisting of hydrogen, halo, $C_{1-4}$alkyl, and $C_{1-6}$haloalkyl.

Embodiment 9 is the compound of embodiment 8, wherein $R_{13}$ is hydrogen, Cl, Br, methyl, or $CF_3$.

Embodiment 10 is the compound of any one of embodiments 1 to 9, wherein $R_1$ is selected from the group consisting of $C_{6-10}$aryl and a 5- to 9-membered heteroaryl group having 1 to 4 heteroatoms groups as ring vertices independently selected from N, C(O), O, and S; and is optionally substituted with 1 to 5 $R_{12}$ groups independently selected from the group consisting of halo, hydroxy, amino, $C_{1-4}$alkylamino, di($C_{1-4}$alkyl)amino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, NR$_{15}$C(O)R$_{14}$, NR$_{15}$C(O)OR$_{14}$, NR$_{14}$C(O)NR$_{15}$R$_{16}$, NR$_{15}$S(O)R$_{14}$, NR$_{15}$S(O)$_2$R$_{14}$, C(O)NR$_{15}$R$_{16}$, S(O) NR$_{15}$R$_{16}$, S(O)$_2$NR$_{15}$R$_{16}$, C(O)R$_{14}$, C(O)OR$_{14}$, OR$_{14}$, SR$_{14}$, S(O)R$_{14}$, and S(O)$_2$R$_{14}$.

Embodiment 11 is the compound of embodiment 10, wherein $R_1$ is phenyl or a 5- to 6-member heteroaryl group having 1 to 4 heteroatoms as ring vertices independently selected from N, O, and S; and is optionally substituted with 1, 2 or 3 $R_{12}$ groups independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and OR$_{14}$.

Embodiment 12 is the compound of any one of embodiments 1 to 11, wherein $R_2$, $R_3$, $R_4$, $R_5$, $R_8$, $R_9$, $R_{10}$ and $R_{11}$ are hydrogen.

Embodiment 13 is the compound of any one of embodiments 1 to 12, wherein:

$R_6$ is selected from the group consisting of amino, $C_{1-4}$aminoalkyl, and $C_{1-4}$alkylamino; and $R_7$ is selected from the group consisting of hydrogen, amido, cyano, halo, and hydroxy, or is selected from the group consisting of $C_{1-4}$alkyl, $C_{1-4}$hydroxyalkyl, $C_{3-6}$cycloalkyl, phenyl, and 5- or 6-membered heteroaryl, any of which is optionally substituted with one or two groups selected from the group consisting of amino, halo, hydroxy, cyano, trifluoromethyl, trifluoromethoxy, $C_{1-4}$alkyl, and $C_{1-4}$alkoxy.

Embodiment 14 is the compound of embodiment 13, wherein $R_6$ is amino or aminomethyl; and $R_7$ is selected from the group consisting of hydroxy, $C_{1-4}$alkyl, and $C_{1-4}$hydroxyalkyl.

Embodiment 15 is the compound of any one of embodiments 1 to 12, wherein $R_6$ and $R_7$ together with the carbon atom to which they are both attached form a 3- to 7-membered saturated or unsaturated ring having 1 to 3 heteroatoms or groups as ring vertices independently selected from N, C(O), O, and S(O)$_m$, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

Embodiment 16 is the compound of embodiment 15, wherein $R_6$ and $R_7$ together with the carbon atom to which they are both attached form a 4- to 6-membered saturated ring having 1 to 3 heteroatoms as ring vertices independently selected from N and O, and that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

Embodiment 17 is the compound of any one of embodiments 1 to 12, wherein $R_6$ and $R_7$ together with the carbon atom to which they are both attached form a 3- to 7-membered cycloalkyl ring that is optionally substituted with one or two groups independently selected from the group consisting of amino, halo, hydroxy, $C_{1-4}$alkyl, $C_{1-4}$alkoxy, $C_{1-4}$alkylamino and $C_{1-4}$aminoalkyl.

Embodiment 18 is the compound of any one of embodiments 1 to 17, wherein $R_1$ is selected from the group consisting of phenyl, pyridyl, pyrimidinyl, pyrazinyl, pyridazinyl, and 1,2,4-triazinyl; and is optionally substituted with 1, 2, or 3 $R_{12}$ independently selected from the group consisting of halo, hydroxy, amino, $C_{1-4}$alkylamino, di($C_{1-4}$alkyl) amino, $C_{1-4}$alkyl, $C_{1-4}$alkoxy, $C_{1-4}$haloalkyl, $C_{1-4}$aminoalkyl, and OR$_{14}$.

Embodiment 19 is the compound of embodiment 18, wherein $R_1$ is phenyl or pyridyl, each of which is substituted with 1 to 3 $R_{12}$.

Embodiment 20 is the compound of any one of embodiments 1 to 18, wherein $R_1$ is selected from the group consisting of:

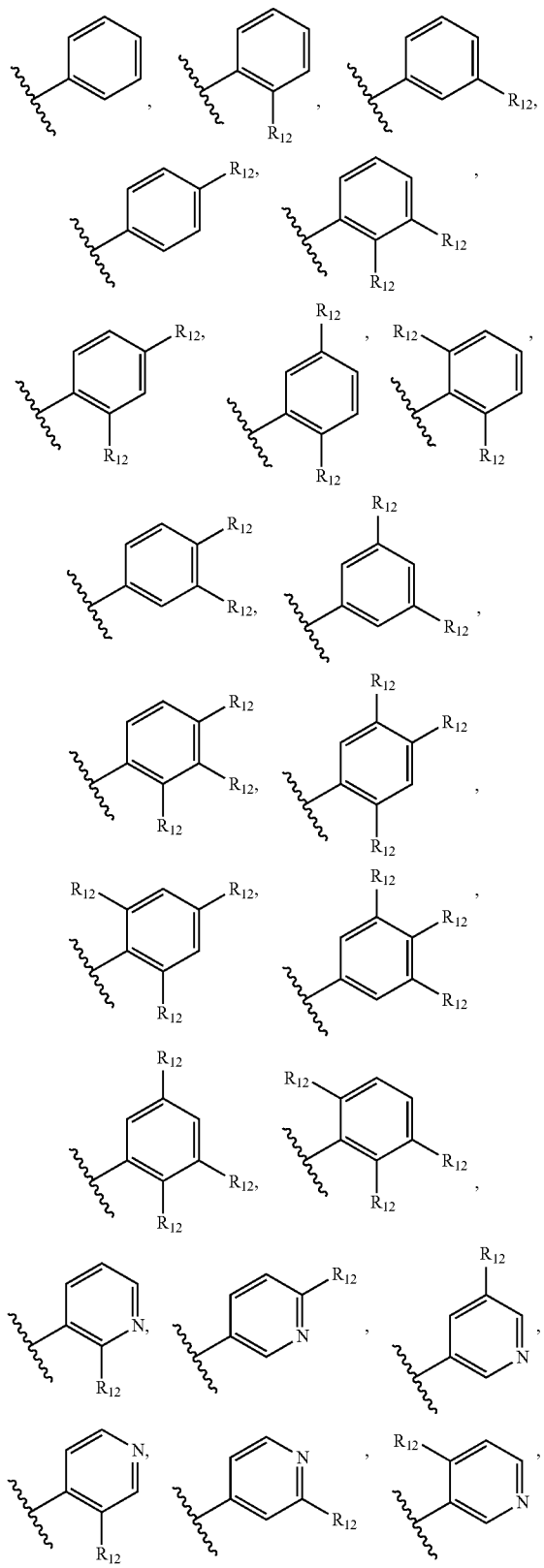

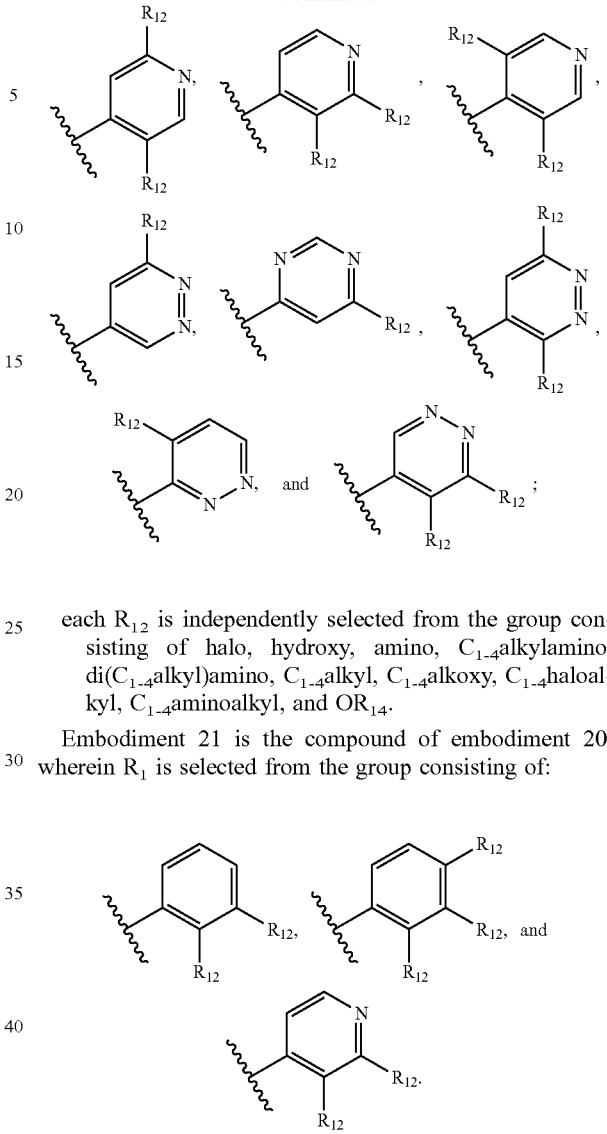

each $R_{12}$ is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, $C_{1-4}$aminoalkyl, and $OR_{14}$.

Embodiment 21 is the compound of embodiment 20, wherein $R_1$ is selected from the group consisting of:

Embodiment 22 is the compound of any one of embodiments 1 to 21, wherein $R_{14}$ is selected from the group consisting of $C_{6-10}$aryl and a 5-10 membered heteroaryl, each of which is optionally substituted by one or more groups independently selected from the group consisting of halo, hydroxy, cyano, and $C_{1-4}$alkyl.

Embodiment 23 is the compound of embodiment 22, wherein $R_{14}$ is phenyl or a 5-6 membered heteroaryl having 1 to 4 heteroatoms as ring vertices independently selected from N, O, and S, each of which is optionally substituted by one or two groups independently selected from the group consisting of halo, hydroxy, cyano, and $C_{1-4}$alkyl.

Embodiment 24 is the compound of embodiment 1, wherein $R_{14}$ is selected from the group consisting of $C_{6-10}$aryl and a 5-10 membered heteroaryl, each of which is optionally substituted by one or more groups independently selected from the group consisting of $C_{1-4}$alkylamido, amino, halo, hydroxy, cyano, $C_{1-4}$alkyl, $C_{1-4}$alkoxy, $C_{1-4}$haloalkyl, $C_{1-4}$haloalkoxy, $C_{1-4}$alkylamino and $C_{1-4}$aminoalkyl.

Embodiment 25 is the compound of embodiment 1, wherein $R_1$ is

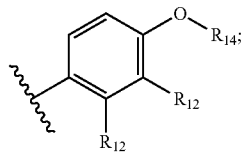

each $R_{12}$ is independently selected from the group consisting of halo, hydroxy, amino, $C_{1-4}$alkylamino, di($C_{1-4}$alkyl)amino, $C_{1-4}$alkyl, $C_{1-4}$alkoxy, $C_{1-4}$haloalkyl, and $C_{1-4}$aminoalkyl; and $R_{14}$ is phenyl or a 5-6 membered heteroaryl having 1 to 4 heteroatoms as ring vertices independently selected from N, O, and S, each of which is optionally substituted by one or two groups independently selected from the group consisting of $C_{1-4}$alkylamido, halo, hydroxy, cyano, and $C_{1-4}$alkyl.

Embodiment 26 is the compound of embodiment 1, wherein each $R_{12}$ is independently selected from the group consisting of F, Cl, Br, $CH_3$, $OCH_3$, $CF_3$,

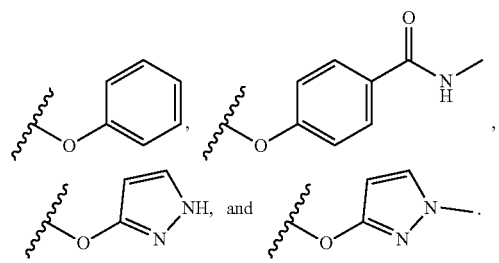

Embodiment 28 is a compound of embodiment 1 or 2, for use as a medicament.

Embodiment 29 is a compound of embodiment 1 or 2, for use in the treatment of a disease driven by one or more PTPN11 mutations.

Embodiment 30 is a compound of embodiment 1 or 2, for use in the treatment of cancer.

Embodiment 31 is the compound of embodiment 30, wherein the cancer is selected from the group consisting of leukemia, melanoma, breast cancer, and colon cancer.

Embodiment 32 is a compound of embodiment 1 or 2, for use in the manufacture of a medicament for the prevention or treatment of a disease or condition ameliorated by the inhibition of PTPN11.

Embodiment 33 is a pharmaceutical composition comprising a compound of embodiment 1 or 2, together with a pharmaceutically acceptable carrier.

Embodiment 34 is a method of inhibition of PTPN11 comprising contacting PTPN11 with a compound of embodiment 1 or 2.

Embodiment 35 is a method of treatment of a PTPN11-mediated disease comprising the administration of a therapeutically effective amount of a compound of embodiment 1 or 2, to a patient in need thereof.

Embodiment 36 is the method of embodiment 35, wherein the disease is cancer.

Embodiment 37 is the method of embodiment 36, wherein the cancer is selected from the group consisting of breast cancer, colon cancer, leukemia, and melanoma.

Embodiment 38 is a method of treatment of a PTPN11-mediated disease comprising the administration of:
a. a therapeutically effective amount of a compound of embodiment 1 or 2; and
b. another therapeutic agent.

Embodiment 39 is the method of embodiment 38, wherein the disease is cancer.

Embodiment 40 is the method of embodiment 39, wherein the cancer is selected from the group consisting of breast cancer, colon cancer, leukemia, and melanoma.

What is claimed is:

1. A compound, represented by the formula:

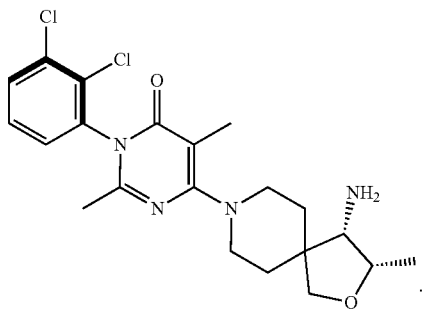

(10b)

2. A pharmaceutically acceptable salt of a compound, wherein the compound is represented by the formula:

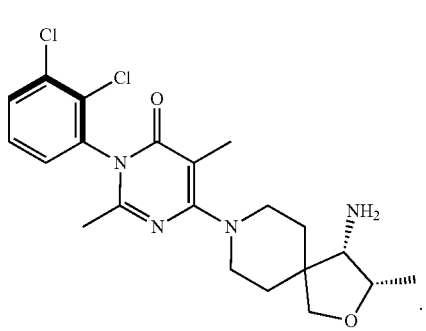

(10b)

3. A pharmaceutical composition comprising the compound of claim 1, together with a pharmaceutically acceptable carrier.

4. A pharmaceutical composition comprising a pharmaceutically acceptable salt of the compound of claim 2, together with a pharmaceutically acceptable carrier.

5. A method of treatment of a PTPN11-mediated disease comprising administering a therapeutically effective amount of the compound of claim 1, to a patient in need thereof, wherein the PTPN11-mediated disease is cancer selected from the group consisting of breast cancer, colon cancer, lung cancer, esophageal cancer, gastric cancer, leukemia, and melanoma.

6. A method of treatment of a PTPN11-mediated disease comprising administering a therapeutically effective amount of a pharmaceutically acceptable salt of the compound of claim 1, to a patient in need thereof, wherein the PTPN11-mediated disease is cancer selected from the group consisting of breast cancer, colon cancer, lung cancer, esophageal cancer, gastric cancer, leukemia, and melanoma.

7. A compound, represented by the formula:

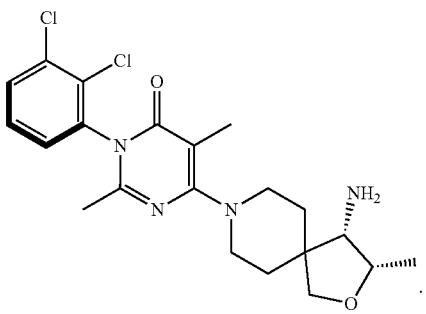

(10a)

8. A pharmaceutically acceptable salt of a compound, wherein the compound is represented by the formula:

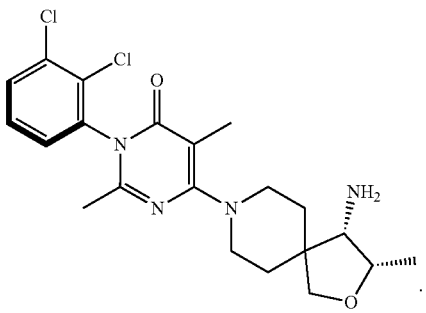

(10a)

9. A pharmaceutical composition comprising the compound of claim 7, together with a pharmaceutically acceptable carrier.

10. A pharmaceutical composition comprising a pharmaceutically acceptable salt of the compound of claim 8, together with a pharmaceutically acceptable carrier.

11. A method of treatment of a PTPN11-mediated disease comprising administering a therapeutically effective amount of the compound of claim 7, to a patient in need thereof, wherein the PTPN11-mediated disease is cancer selected from the group consisting of breast cancer, colon cancer, lung cancer, esophageal cancer, gastric cancer, leukemia, and melanoma.

12. A method of treatment of a PTPN11-mediated disease comprising administering a therapeutically effective amount of a pharmaceutically acceptable salt of the compound of claim 8, to a patient in need thereof, wherein the PTPN11-mediated disease is cancer selected from the group consisting of breast cancer, colon cancer, lung cancer, esophageal cancer, gastric cancer, leukemia, and melanoma.

13. A method of treatment of lung cancer comprising administering to a patient in need thereof a therapeutically effective amount of the compound represented by the formula:

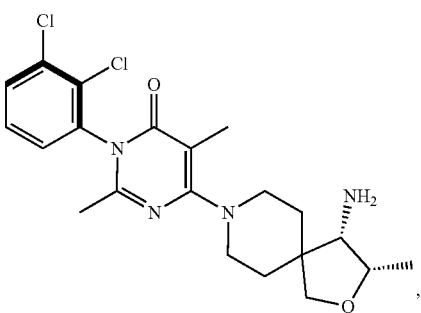

(10b)

or a pharmaceutically acceptable salt thereof.

14. The method of claim 13, wherein the lung cancer is non-small cell lung cancer.

15. A method of treatment of colon cancer comprising administering to a patient in need thereof a therapeutically effective amount of the compound represented by the formula:

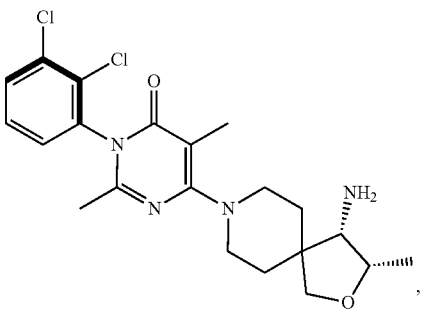

(10b)

or a pharmaceutically acceptable salt thereof.

16. The method of claim 15, wherein the colon cancer is colorectal cancer.

* * * * *